(12) United States Patent
Takita et al.

(10) Patent No.: US 10,930,855 B2
(45) Date of Patent: Feb. 23, 2021

(54) LIGHT-EMITTING ELEMENT, LIGHT-EMITTING DEVICE, ELECTRONIC DEVICE, LIGHTING DEVICE, LIGHTING SYSTEM, AND GUIDANCE SYSTEM

(71) Applicant: SEMICONDUCTOR ENERGY LABORATORY CO., LTD., Atsugi (JP)

(72) Inventors: Yusuke Takita, Kanagawa (JP); Satoshi Seo, Kanagawa (JP); Tsunenori Suzuki, Kanagawa (JP); Harue Osaka, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 0 days.

(21) Appl. No.: 15/779,661

(22) PCT Filed: Dec. 6, 2016

(86) PCT No.: PCT/IB2016/057370
§ 371 (c)(1),
(2) Date: May 29, 2018

(87) PCT Pub. No.: WO2017/103732
PCT Pub. Date: Jun. 22, 2017

(65) Prior Publication Data
US 2018/0358562 A1 Dec. 13, 2018

(30) Foreign Application Priority Data

Dec. 17, 2015 (JP) .............................. JP2015-246311
Jan. 22, 2016 (JP) .............................. JP2016-010274

(51) Int. Cl.
| | | |
|---|---|---|
| *C07D 333/50* | (2006.01) | |
| *H01L 51/00* | (2006.01) | |
| *C07D 333/76* | (2006.01) | |
| *C09K 11/06* | (2006.01) | |
| *H05B 45/00* | (2020.01) | |
| *H05B 47/11* | (2020.01) | |
| *H01L 51/50* | (2006.01) | |

(52) U.S. Cl.
CPC ........ *H01L 51/0061* (2013.01); *C07D 333/76* (2013.01); *C09K 11/06* (2013.01); *H01L 51/0059* (2013.01); *H01L 51/0074* (2013.01); *H05B 45/60* (2020.01); *H05B 47/11* (2020.01); *H01L 51/5064* (2013.01); *H01L 2251/552* (2013.01)

(58) Field of Classification Search
CPC .................................................. C07D 333/50
See application file for complete search history.

(56) References Cited

U.S. PATENT DOCUMENTS

| | | |
|---|---|---|
| 8,115,383 B2 | 2/2012 | Cok et al. |
| 8,203,262 B2 | 6/2012 | Seo et al. |
| 8,486,543 B2 | 7/2013 | Seo et al. |
| 8,703,304 B2 | 4/2014 | Yabunouchi |
| 8,841,655 B2 | 9/2014 | Okamoto |
| 9,087,997 B2 | 7/2015 | Yabunouchi |
| 9,209,426 B2 | 12/2015 | Suzuki et al. |
| 9,257,663 B2 | 2/2016 | Nakamura et al. |
| 9,278,926 B2 | 3/2016 | Kato |
| 9,343,681 B2 | 5/2016 | Suzuki et al. |
| 9,401,483 B2 | 7/2016 | Suzuki et al. |
| 9,496,505 B2 | 11/2016 | Nowatari et al. |
| 9,698,354 B2 | 7/2017 | Seo et al. |
| 9,831,441 B2 | 11/2017 | Parham et al. |
| 10,014,480 B2 | 7/2018 | Balaganesan et al. |
| 10,056,560 B2 | 8/2018 | Lee et al. |
| 10,319,916 B2 | 6/2019 | Lee et al. |
| 2002/0050786 A1 | 5/2002 | Yamazaki et al. |

(Continued)

FOREIGN PATENT DOCUMENTS

| | | |
|---|---|---|
| CN | 001586095 A | 2/2005 |
| CN | 101432272 A | 5/2009 |

(Continued)

OTHER PUBLICATIONS

International Search Report (Application No. PCT/IB2016/057370) dated Mar. 7, 2017.

(Continued)

*Primary Examiner* — John S Kenyon
(74) *Attorney, Agent, or Firm* — Fish & Richardson P.C.

(57) ABSTRACT

An object is to provide a light-emitting element with a favorable lifetime.
A light-emitting element which includes a first electrode, a second electrode, and an EL layer and in which the EL layer includes a hole-injection layer and first to fourth layers; the hole-injection layer includes an organic acceptor and is positioned between the first electrode and the first layer; the first layer includes a first hole-transport material; the second layer includes a second hole-transport material and is positioned between the first layer and the third layer; the third layer includes a third hole-transport material; the fourth layer includes a host material and a light-emitting material and is positioned between the third layer and the second electrode; the HOMO level of the second hole-transport material is deeper than the HOMO level of the first hole-transport material; the HOMO level of the host material is deeper than the second hole-transport material HOMO level; the HOMO level of the third hole-transport material is deeper than or equal to the HOMO level of the host material; a difference between the HOMO level of the second hole-transport material and the HOMO level of the third hole-transport material is less than or equal to 0.3 eV; and the second hole-transport material is a triarylamine compound having a structure where a dibenzofuran skeleton or a dibenzothiophene skeleton is bonded to nitrogen of an amine directly or via a divalent aromatic hydrocarbon group.

11 Claims, 30 Drawing Sheets

(56) References Cited

U.S. PATENT DOCUMENTS

| | | | |
|---|---|---|---|
| 2004/0245542 | A1 | 12/2004 | Kim |
| 2007/0278938 | A1 | 12/2007 | Yabunouchi et al. |
| 2010/0001636 | A1† | 1/2010 | Yabunouchi |
| 2011/0101870 | A1 | 5/2011 | Cok et al. |
| 2011/0127510 | A1 | 6/2011 | Seo et al. |
| 2012/0248426 | A1 | 10/2012 | Kato |
| 2014/0084273 | A1 | 3/2014 | Nakayama et al. |
| 2015/0008404 | A1 | 1/2015 | Oh et al. |
| 2015/0041795 | A1 | 2/2015 | Suzuki et al. |
| 2015/0171356 | A1 | 6/2015 | Nakamura et al. |
| 2015/0188057 | A1 | 7/2015 | Itoi et al. |
| 2015/0280133 | A1 | 10/2015 | Parham et al. |
| 2016/0099420 | A1 | 4/2016 | Itoi et al. |
| 2016/0133848 | A1* | 5/2016 | Huang et al. ........ C07D 333/76 257/40 |
| 2016/0141510 | A1 | 5/2016 | Sasaki et al. |
| 2016/0336519 | A1 | 11/2016 | Seo et al. |
| 2017/0054088 | A1 | 2/2017 | Nowatari et al. |
| 2017/0062734 | A1 | 3/2017 | Suzuki et al. |
| 2017/0294617 | A1 | 10/2017 | Seo et al. |
| 2017/0317289 | A1* | 11/2017 | Lee .................. C07D 333/76 |
| 2019/0006597 | A1 | 1/2019 | Lee et al. |

FOREIGN PATENT DOCUMENTS

| | | |
|---|---|---|
| CN | 102046613 A | 5/2011 |
| CN | 102142525 A | 8/2011 |
| CN | 102596907 A | 7/2012 |
| CN | 102598860 A | 7/2012 |
| CN | 104092211 A | 10/2014 |
| CN | 104509211 A | 4/2015 |
| CN | 104756275 A | 7/2015 |
| CN | 104934535 A | 9/2015 |
| CN | 105609649 A | 5/2016 |
| CN | 106232768 A | 12/2016 |
| EP | 1444869 A | 8/2004 |
| EP | 2295421 A | 3/2011 |
| EP | 2330652 A | 6/2011 |
| EP | 2494848 A | 9/2012 |
| EP | 2502908 A | 9/2012 |
| EP | 2861044 A | 4/2015 |
| EP | 2915199 A | 9/2015 |
| EP | 2639231 B1 † | 2/2019 |
| JP | 2002-151269 A | 5/2002 |
| JP | 2005-510025 | 4/2005 |
| JP | 2007-156651 A | 6/2007 |
| JP | 2009-177157 A | 8/2009 |
| JP | 2011-009498 A | 1/2011 |
| JP | 2011-139044 A | 7/2011 |
| JP | 2013-509712 | 3/2013 |
| JP | 2013-258022 A | 12/2013 |
| JP | 2014-167946 A | 9/2014 |
| JP | 5739815 | 6/2015 |
| JP | 2015-128113 A | 7/2015 |
| JP | 2015-128115 A | 7/2015 |
| JP | 2015-144233 A | 8/2015 |
| JP | 2015-536567 | 12/2015 |
| JP | 2016-076566 A | 5/2016 |
| JP | 2016-094408 A | 5/2016 |
| JP | 2016-100376 A | 5/2016 |
| KR | 2003-0039100 A | 5/2003 |
| KR | 2008-0112325 A | 12/2008 |
| KR | 2011-0011647 A | 2/2011 |
| KR | 2011-0061500 A | 6/2011 |
| KR | 2012-0066076 A | 6/2012 |
| KR | 2012-0098700 A | 9/2012 |
| KR | 10-1493482 | 2/2015 |
| KR | 2015-0018437 A | 2/2015 |
| KR | 2015-0030659 A | 3/2015 |
| KR | 2015-0077269 A | 7/2015 |
| KR | 2015-0079911 A | 7/2015 |
| KR | 2015-0138000 A | 12/2015 |
| KR | 2016-0041745 A | 4/2016 |
| KR | 2016-0060536 A | 5/2016 |
| TW | 201125118 | 7/2011 |
| TW | 201129546 | 9/2011 |
| TW | 201133976 | 10/2011 |
| TW | 201304232 | 1/2013 |
| TW | 201410843 | 3/2014 |
| TW | 201602060 | 1/2016 |
| WO | WO-2003/043383 | 5/2003 |
| WO | WO-2007/125714 | 11/2007 |
| WO | WO-2009/145016 | 12/2009 |
| WO | WO-2011/059099 | 5/2011 |
| WO | WO-2011/059664 | 5/2011 |
| WO | WO-2011/065136 | 6/2011 |
| WO | WO-2012/046560 | 4/2012 |
| WO | WO-2012/176674 | 12/2012 |
| WO | WO-2013/187007 | 12/2013 |
| WO | WO-2014/067614 | 5/2014 |
| WO | WO-2015/182887 | 12/2015 |

OTHER PUBLICATIONS

Written Opinion (Application No. PCT/IB2016/057370) dated Mar. 7, 2017.
Notification (Application No. 2017-555870) dated Apr. 9, 2019.
Information Offer Form (Application No. 2017-555870) dated Apr. 1, 2019.
Chinese Office Action (Application No. 201680074060.5) dated Aug. 4, 2020.

\* cited by examiner
† cited by third party

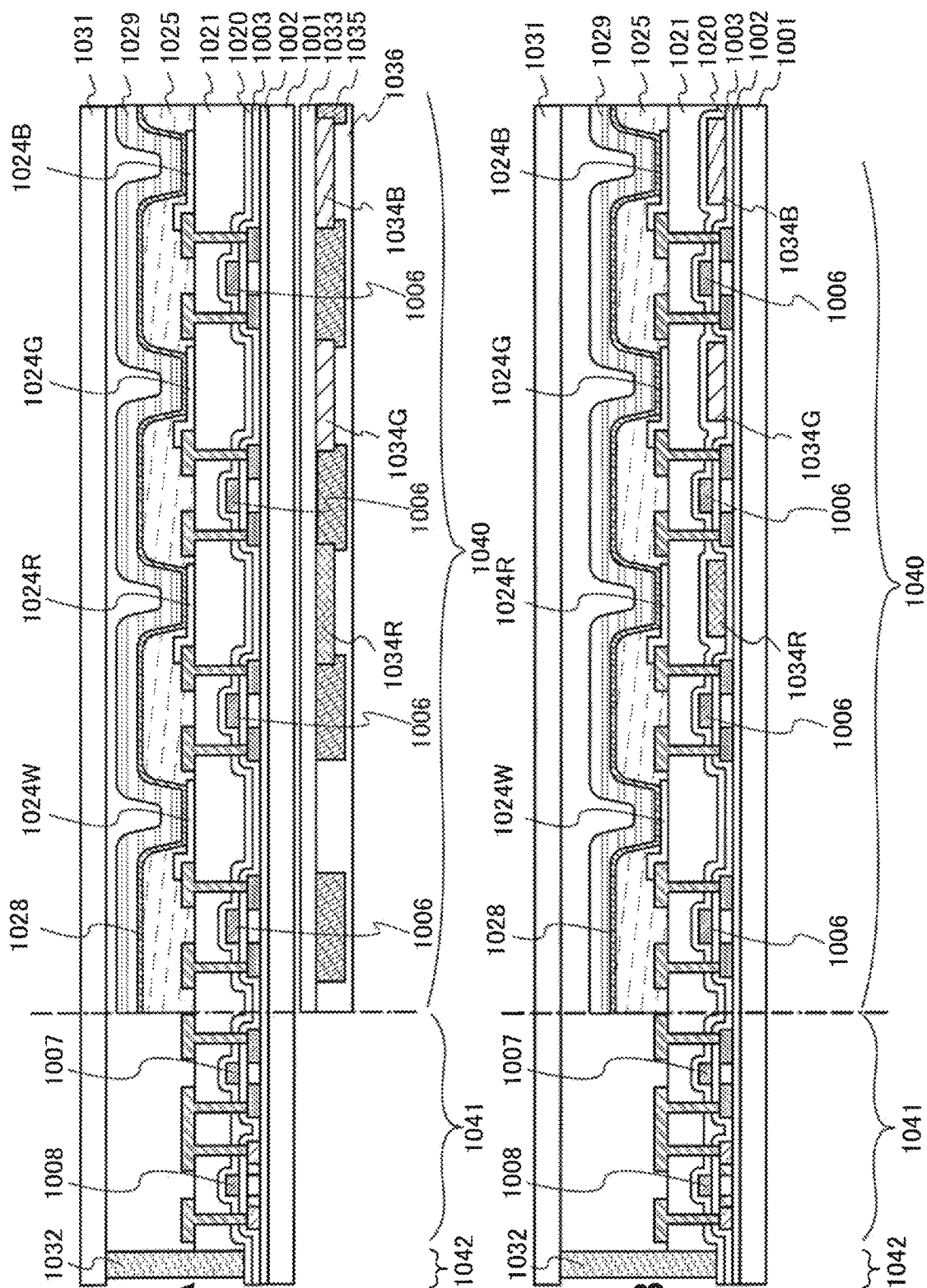

FIG. 7A
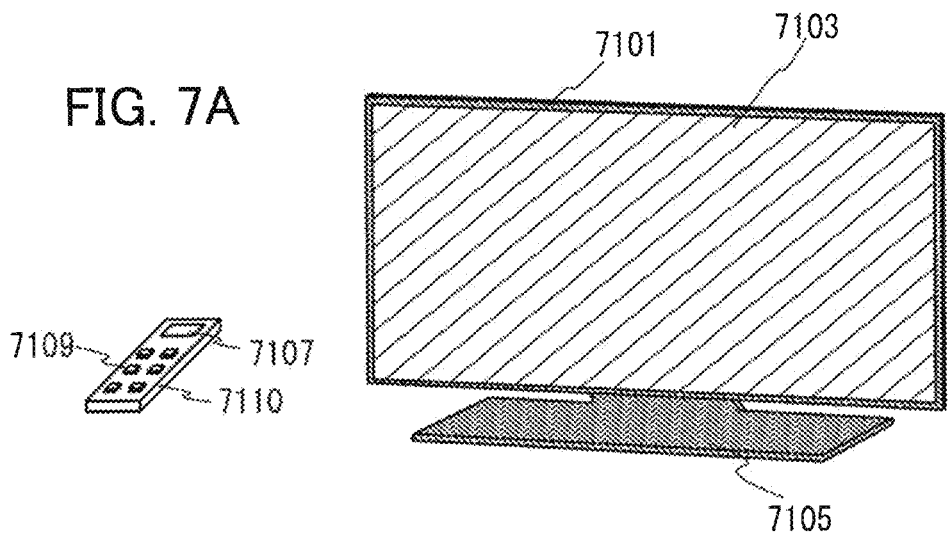
FIG. 7B1
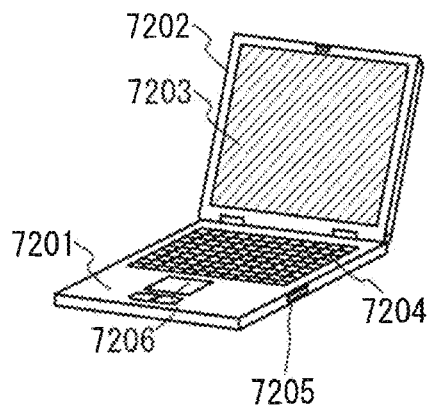
FIG. 7B2
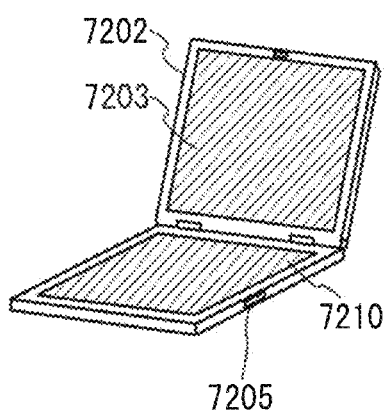
FIG. 7C
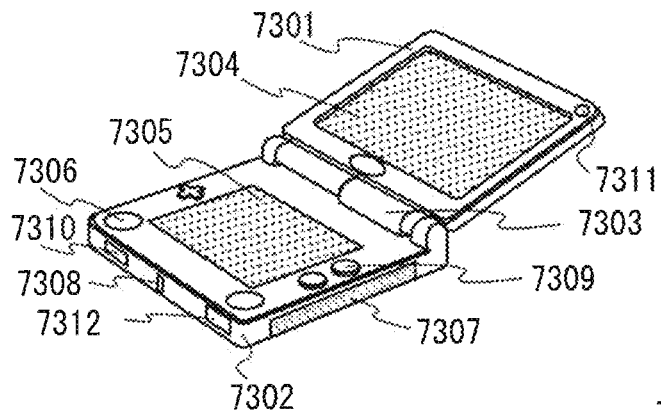
FIG. 7D
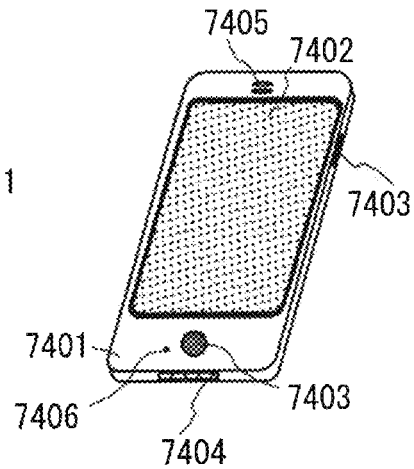

LIGHT-EMITTING ELEMENT, LIGHT-EMITTING DEVICE, ELECTRONIC DEVICE, LIGHTING DEVICE, LIGHTING SYSTEM, AND GUIDANCE SYSTEM

CROSS REFERENCE TO RELATED APPLICATIONS

This application is a U.S. National Phase Application under 35 U.S.C. § 371 of International Application PCT/IB2016/057370, filed on Dec. 6, 2016, which claims the benefit of foreign priority applications filed in Japan as Application No. 2015-246311 on Dec. 17, 2015, and Application No. 2016-010274 on Jan. 22, 2016, all of which are incorporated by reference.

TECHNICAL FIELD

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition (composition of matter). Thus, more specific examples of the technical field of one embodiment of the present invention disclosed in this specification include a semiconductor device, a display device, a liquid crystal display device, a light-emitting device, a lighting device, a power storage device, a storage device, an imaging device, a driving method thereof, and a manufacturing method thereof.

BACKGROUND ART

Light-emitting elements (organic EL elements) using organic compounds and utilizing electroluminescence (EL: electroluminescence) have been put to more practical use. In the basic structure of these light-emitting elements, an organic compound layer containing a light-emitting material (EL layer) is interposed between a pair of electrodes. Carriers are injected by application of voltage to the element, and recombination energy of the carriers is used, whereby light emission can be obtained from the light-emitting material.

Such light-emitting elements are self-luminous elements and thus have advantages over liquid crystal, such as high visibility and no need for backlight when used as pixels of a display, and are suitable as flat panel display elements. In addition, it is also a great advantage that a display using such light-emitting elements can be manufactured as a thin and lightweight display. Furthermore, extremely high response speed is also a feature thereof.

Furthermore, in such light-emitting elements, light-emitting layers can be successively formed two-dimensionally, so that planar light emission can be obtained. This feature is difficult to obtain with point light sources typified by incandescent lamps and LEDs or linear light sources typified by fluorescent lamps. Thus, light-emitting elements also have great potential as planar light sources applicable to lighting devices and the like.

Displays or lighting devices using light-emitting elements can be suitably used for a variety of electronic devices as described above, and research and development have progressed for light-emitting elements with favorable efficiency and lifetimes.

An organic acceptor is given as a material of a hole-injection layer that is used to facilitate injection of carriers, particularly holes, to an EL layer. An organic acceptor is suitable for mass production because it can be easily deposited by evaporation; therefore, the use of an organic acceptor spreads widely. However, when the LUMO level of an organic acceptor is distanced from the HOMO level of an organic compound included in a hole-transport layer, it is difficult to inject holes into an EL layer. Thus, in the case where the HOMO level of the organic compound included in the hole-transport layer is made to be shallow in order to make the LUMO level of the organic acceptor closer to the HOMO level of the organic compound included in the hole-transport layer, the difference between the HOMO level of the light-emitting layer and the HOMO level of the organic compound included in the hole-transport layer increases. This makes it difficult to inject holes from the hole-transport layer to the host material of the light-emitting layer even when holes can be injected into the EL layer, which has been a problem.

Patent document 1 discloses a structure in which a hole-transport material whose HOMO level is between the HOMO level of a first hole-injection layer and the HOMO level of a host material is provided between a light-emitting layer and a first hole-transport layer in contact with the hole-injection layer.

Although the characteristics of light-emitting elements have been markedly improved, we cannot help saying that advanced requirements for various characteristics including efficiency and durability are not yet satisfied.

PRIOR ART DOCUMENT

Patent Document

[Patent Document 1] PCT International Publication No. WO2011/065136 pamphlet

SUMMARY OF THE INVENTION

Problems to be Solved by the Invention

Thus, a problem of one embodiment of the present invention is to provide a novel light-emitting element. Another object is to provide a light-emitting element with a favorable lifetime. Another object is to provide a light-emitting element with high emission efficiency.

Another object of one embodiment of the present invention is to provide a light-emitting device, an electronic device, and a display device with highly reliability. Another object of one embodiment of the present invention is to provide a light-emitting device, an electronic device, and a display device with low power consumption.

Another object of one embodiment of the present invention is to provide a novel lighting system and a novel guidance system.

It is only necessary that the present invention solves any one of the above problems.

Means for Solving the Problems

One embodiment of the present invention is a light-emitting element which includes a first electrode, a second electrode, and an EL layer and in which the EL layer is positioned between the first electrode and the second electrode; the EL layer includes a hole-injection layer, a first layer, a second layer, a third layer, and a fourth layer; the hole-injection layer includes an organic acceptor; the hole-injection layer is positioned between the first electrode and the first layer; the second layer is positioned between the first layer and the third layer; the fourth layer is positioned between the third layer and the second electrode; the first layer includes a first hole-transport material; the second layer includes a second hole-transport material; the third layer includes a third hole-transport material; the fourth layer includes a host material and a light-emitting material; the HOMO level of the second hole-transport material is deeper than the HOMO level of the first hole-transport material; the HOMO level of the host material is deeper than the second hole-transport material HOMO level; the HOMO level of the third hole-transport material is deeper than or equal to the HOMO level of the host material; a difference between the HOMO level of the second hole-transport material and the HOMO level of the third hole-transport material is less than or equal to 0.3 eV; and the second hole-transport material is a triarylamine compound having a structure where a dibenzofuran skeleton or a dibenzothiophene skeleton is bonded to nitrogen of an amine directly or via a divalent aromatic hydrocarbon group.

Another embodiment of the present invention is a light-emitting element having the above structure in which the second hole-transport material is a substance having one or two structures in each of which the dibenzofuran skeleton or the dibenzothiophene skeleton is bonded to the nitrogen of the amine directly or via the divalent aromatic hydrocarbon group.

Another embodiment of the present invention is a light-emitting element having the above structure in which the 4-position of the dibenzofuran skeleton or the dibenzothiophene skeleton is bonded to the nitrogen of the amine directly or via the divalent aromatic hydrocarbon group.

Another embodiment of the present invention is a light-emitting element having the above structure in which the second hole-transport material is an organic compound having a partial structure represented by General Formula (g1-1) shown below.

[Chemical Formula 1]

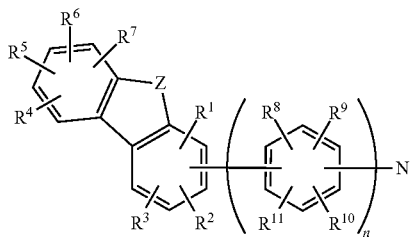

(g1-1)

Note that in General Formula (g1-1), Z represents an oxygen atom or a sulfur atom. Further, n represents an integer of 0 to 3. In addition, each of $R^1$ to $R^{11}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

Another embodiment of the present invention is a light-emitting element having the above structure in which the second hole-transport material is an organic compound having a partial structure represented by General Formula (g1-2) shown below.

[Chemical Formula 2]

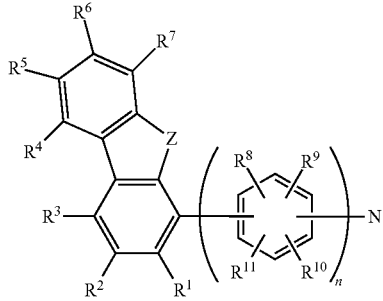

(g1-2)

Note that in General Formula (g1-2), Z represents an oxygen atom or a sulfur atom. Further, n represents an integer of 0 to 3. In addition, each of $R^1$ to $R^{11}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

Another embodiment of the present invention is a light-emitting element having the above structure in which the second hole-transport material is a monoamine compound.

Another embodiment of the present invention is a light-emitting element having the above structure in which the second hole-transport material is an organic compound represented by General Formula (G1-1) shown below.

[Chemical Formula 3]

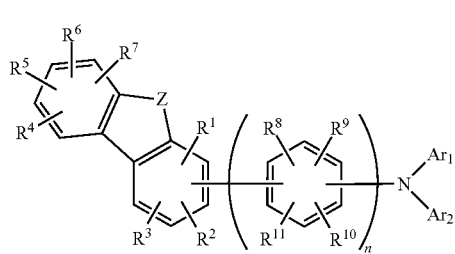

(G1-1)

Note that in General Formula (G1-1), X represents an oxygen atom or a sulfur atom, and n represents an integer of 0 to 3. In addition, $Ar^1$ represents any one of aromatic hydrocarbon groups having 6 to 18 nuclear atoms, and $Ar^2$ is any one of an aromatic hydrocarbon group having 6 to 18 nuclear atoms and a group represented by General Formula (g2-1) shown below. Further, each of $R^1$ to $R^{11}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

[Chemical Formula 4]

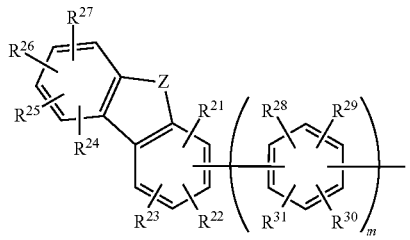

(g2-1)

In General Formula (g2-1), Z represents an oxygen atom or a sulfur atom, and m represents an integer of 0 to 3. In addition, each of $R^{21}$ to $R^{31}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

Another embodiment of the present invention is a light-emitting element having the above structure in which the second hole-transport material is an organic compound represented by General Formula (G1-2) shown below.

[Chemical Formula 5]

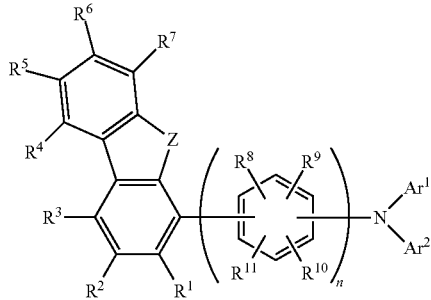

(G1-2)

Note that in General Formula (G1-2), Z represents an oxygen atom or a sulfur atom, and n represents an integer of 0 to 3. In addition, $Ar^1$ represents any one of aromatic hydrocarbon groups having 6 to 18 nuclear atoms, and $Ar^2$ is any one of an aromatic hydrocarbon group having 6 to 18 nuclear atoms and a group represented by General Formula (g2-2) shown below. Further, each of $R^1$ to $R^{11}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

[Chemical Formula 6]

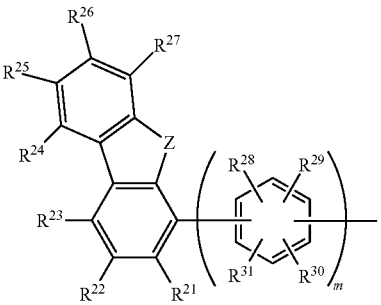

(g2-2)

In General Formula (g2-2), Z represents an oxygen atom or a sulfur atom, and m represents an integer of 0 to 3. In addition, each of $R^{11}$ to $R^{31}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

Another embodiment of the present invention is a light-emitting element having the above structure in which the organic acceptor is 2,3,6,7,10,11-hexacyano-1,4,5,8,9,12-hexaazatriphenylene.

Another embodiment of the present invention is a light-emitting element having the above structure in which the HOMO level of the second hole-transport material is greater than or equal to −5.7 eV and less than or equal to −5.4 eV.

Another embodiment of the present invention is a light-emitting element having the above structure in which the difference between the HOMO level of the first hole-transport material and the HOMO level of the second hole-transport material is less than or equal to 0.3 eV.

Another embodiment of the present invention is a light-emitting element having the above structure in which the difference between the HOMO level of the second hole-transport material and the HOMO level of the third hole-transport material is less than or equal to 0.2 eV.

Another embodiment of the present invention is a light-emitting element having the above structure in which the difference between the HOMO level of the first hole-transport material and the HOMO level of the second hole-transport material is less than or equal to 0.2 eV.

Another embodiment of the present invention is a light-emitting element having the above structure in which the HOMO level of the light-emitting material is higher than the HOMO level of the host material.

Another embodiment of the present invention is a light-emitting element having the above structure in which the first hole-transport material is a substance which is a tri-arylamine and has a fluorenylamine skeleton.

Another embodiment of the present invention is a light-emitting element having the above structure in which the third hole-transport material is a substance which does not include an amine.

Another embodiment of the present invention is a light-emitting element having the above structure in which the third hole-transport material includes a carbazole skeleton.

Another embodiment of the present invention is a light-emitting element having the above structure in which the carbazole skeleton is an N-phenylcarbazole skeleton.

Another embodiment of the present invention is a light-emitting element having the above structure in which the third hole-transport material includes a triphenylene skeleton.

Another embodiment of the present invention is a light-emitting element having the above structure in which the third hole-transport material includes a naphthalene skeleton.

Another embodiment of the present invention is a light-emitting element having the above structure in which the host material includes an anthracene skeleton.

Another embodiment of the present invention is a light-emitting element having the above structure in which the host material includes a diphenylanthracene skeleton.

Another embodiment of the present invention is a light-emitting element having the above structure in which the host material includes a carbazole skeleton.

Another embodiment of the present invention is a light-emitting element having the above structure in which the carbazole skeleton includes a benzocarbazole skeleton.

Another embodiment of the present invention is a light-emitting element having the above structure in which the carbazole skeleton is a dibenzocarbazole skeleton.

Another embodiment of the present invention is a light-emitting element having the above structure in which the light-emitting material is a fluorescent substance.

Another embodiment of the present invention is a light-emitting element having the above structure in which the light-emitting material emits blue fluorescence.

Another embodiment of the present invention is a light-emitting element having the above structure in which the light-emitting material is a condensed aromatic diamine compound.

Another embodiment of the present invention is a light-emitting element having the above structure in which the light-emitting material is a pyrenediamine compound.

Another embodiment of the present invention is a lighting system which includes a control portion, a sensor portion, and a lighting portion and in which the lighting portion includes a plurality of light-emitting device portions, the light-emitting device portion includes one or more light-emitting elements, and the light-emitting element is the light-emitting element described in any of the above.

Another embodiment of the present invention is a lighting system having the above structure in which the sensor portion senses presence information or positional information of a user and transmits the information to the control portion, whereby the control portion makes the light-emitting device portion emit light with appropriate emission intensity.

Another embodiment of the present invention is a lighting system having the above structure in which the emission intensity of the light-emitting device portion is sequentially changed with a change in the positional information of the user.

Another embodiment of the present invention is a guidance system in which a sensor portion has a function of detecting attribute information of a user and which guides the user in the appropriate direction by changing the emission intensity of the light-emitting device portion on the basis of the attribute information and the positional information of the user.

Another embodiment of the present invention is a light-emitting device including the light-emitting element described in any of the above and a transistor or a substrate.

Another embodiment of the present invention is an electronic device including the above light-emitting device and a sensor, an operation button, a speaker, or a microphone.

Another embodiment of the present invention is a lighting device including the above light-emitting device and a housing.

Another embodiment of the present invention is an organic compound represented by General Formula (G2) shown below.

[Chemical Formula 7]

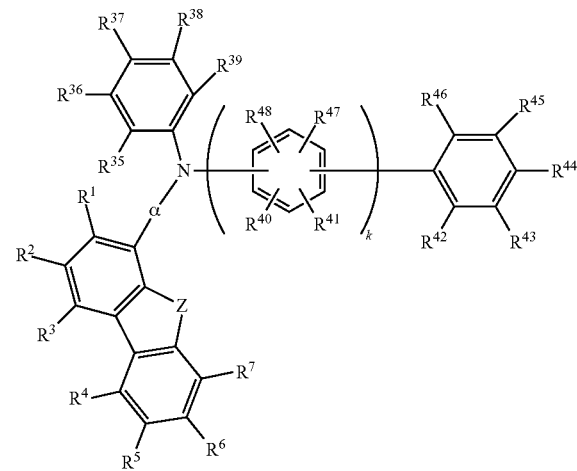

(G2)

Note that in General Formula (G2), each of $R^1$ to R7 and $R^{35}$ to $R^{48}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms. In addition, α represents a divalent aromatic hydrocarbon group having 6 nuclear atoms to 18 carbon atoms, and Z represents an oxygen atom or a sulfur atom. Further, k represents 1 or 2.

Another embodiment of the present invention is an organic compound represented by General Formula (G3) shown below.

[Chemical Formula 8]

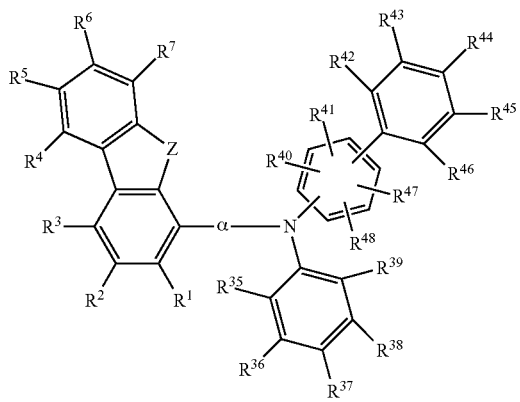

(G3)

Note that in General Formula (G3), each of $R^1$ to R7 and $R^{35}$ to $R^{48}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms. In addition, α represents a divalent aromatic hydrocarbon group having 6 nuclear atoms to 18 carbon atoms, and Z represents an oxygen atom or a sulfur atom. Further, k represents 1 or 2.

Another embodiment of the present invention is an organic compound represented by General Formula (G4) shown below.

[Chemical Formula 9]

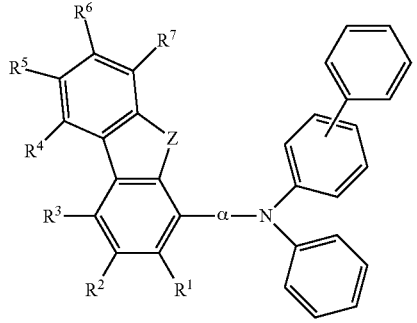
(G4)

Note that in General Formula (G4), each of $R^1$ to $R^7$ independently represents any one of hydrogen, a saturated hydrocarbon group having 1 to 6 carbon atoms, a cyclic saturated hydrocarbon group having 3 to 6 carbon atoms, and a substituted or unsubstituted aromatic hydrocarbon group having 6 to 18 carbon atoms. In addition, α represents a divalent aromatic hydrocarbon group having 6 nuclear atoms to 18 carbon atoms, and Z represents an oxygen atom or a sulfur atom.

Another embodiment of the present invention is an organic compound represented by General Formula (G5) shown below.

[Chemical Formula 10]

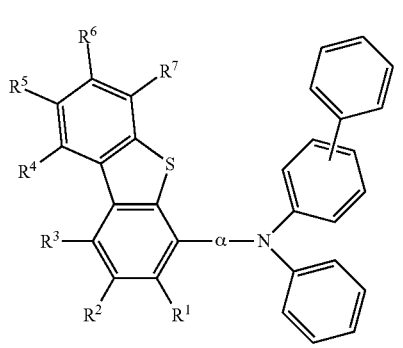
(G5)

Note that in General Formula (G5), each of $R^1$ to $R^7$ independently represents any one of hydrogen, a saturated hydrocarbon group having 1 to 6 carbon atoms, a cyclic saturated hydrocarbon group having 3 to 6 carbon atoms, and a substituted or unsubstituted aromatic hydrocarbon group having 6 to 18 carbon atoms. In addition, α represents a divalent aromatic hydrocarbon group having 6 nuclear atoms to 18 carbon atoms, and Z represents an oxygen atom or a sulfur atom.

Another embodiment of the present invention is an organic compound having the above structure in which α is any one of groups represented by Structural Formulae (α-1) to (α-5) shown below.

[Chemical Formula 11]

(α-1)

(α-2)

(α-3)

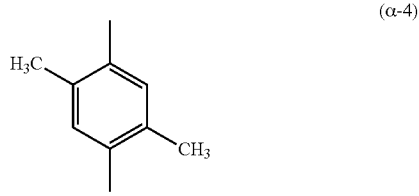
(α-4)

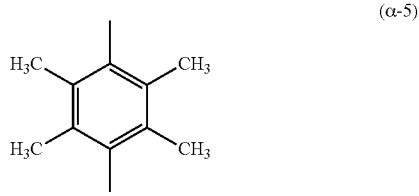
(α-5)

Another embodiment of the present invention is an organic compound represented by General Formula (G6) shown below.

[Chemical Formula 12]

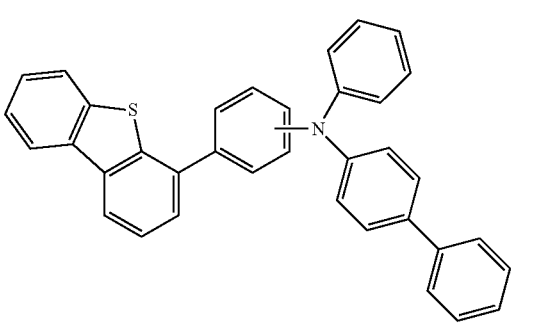
(G6)

Another embodiment of the present invention is an organic compound represented by Structural Formula (100) shown below.

[Chemical Formula 13]

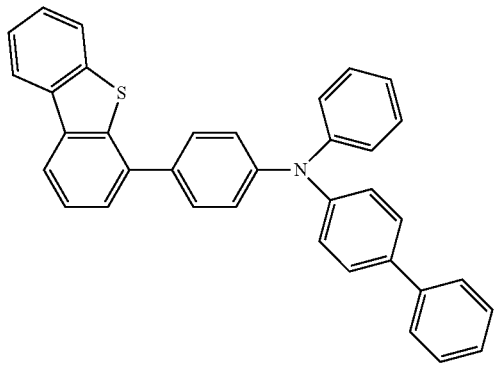

(100)

Another embodiment of the present invention is an organic compound represented by Structural Formula (101) shown below.

[Chemical Formula 14]

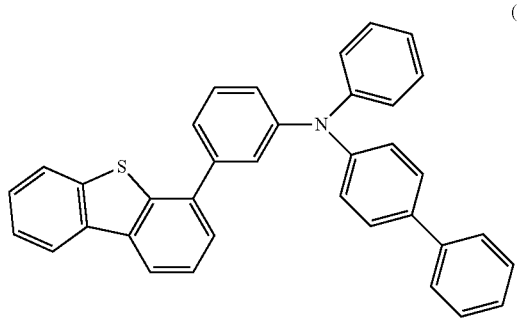

(101)

Note that the light-emitting device in this specification includes an image display device using a light-emitting element. The light-emitting device may be included in a module in which a light-emitting element is provided with a connector such as an anisotropic conductive film or a TCP (Tape Carrier Package), a module in which a printed wiring board is provided at the end of a TCP, and a module in which an IC (integrated circuit) is directly mounted on a light-emitting element by a COG (Chip On Glass) method. The light-emitting device may also be included in lighting equipment or the like.

Effect of the Invention

In one embodiment of the present invention, a novel light-emitting element can be provided. Alternatively, a light-emitting element with a long lifetime can be provided. Alternatively, a light-emitting element with high emission efficiency can be provided.

In another embodiment of the present invention, a light-emitting device, an electronic device, and a display device each with high reliability can be provided. In another embodiment of the present invention, a light-emitting device, an electronic device, and a display device each with low power consumption can be provided.

In another embodiment of the present invention, a novel lighting system and a novel guidance system can be provided.

Note that the description of these effects does not disturb the existence of other effects. Note that one embodiment of the present invention does not necessarily achieve all of these effects. Note that effects other than these will be apparent from and can be derived from the description of the specification, the drawings, the claims, and the like.

BRIEF DESCRIPTION OF THE DRAWINGS

FIGS. 3A and 3B are conceptual diagrams of an active matrix light-emitting device.

FIGS. 7A-7D are diagrams illustrating an electronic device.

Embodiments of the present invention are described below using the drawings. Note that the present invention is not limited to the following description, and it is readily appreciated by those skilled in the art that modes and details of the present invention can be modified in various ways without departing from the spirit and scope of the present invention. Thus, the present invention should not be construed as being limited to the description in the following embodiments.

EMBODIMENT 1

Figure 1A:
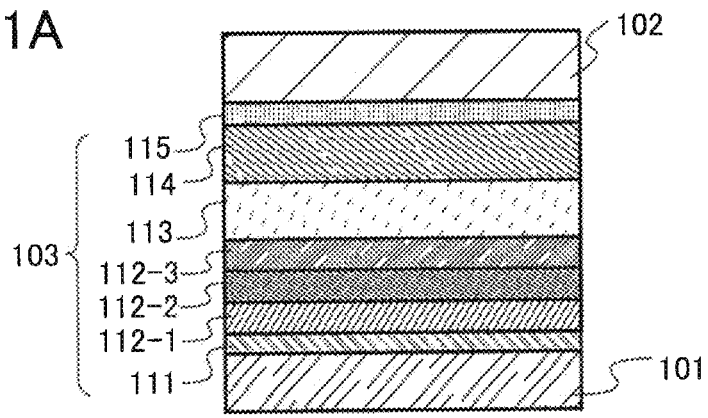
FIGS. 1A-1C are conceptual diagrams of a light-emitting element.

FIG. 1(A) is a diagram illustrating a light-emitting element of one embodiment of the present invention. The light-emitting element of one embodiment of the present invention includes a first electrode 101, a second electrode 102, and an EL layer 103, and the EL layer 103 includes a hole-injection layer 111, a first hole-transport layer 112-1, a second hole-transport layer 112-2, a third hole-transport layer 112-3, and a light-emitting layer 113 from the first electrode 101 side. The EL layer 103 may further include an electron-transport layer 114 and an electron-injection layer 115.

In the light-emitting element of one embodiment of the present invention, the light-emitting layer 113 includes a host material and a light-emitting material; the hole-injection layer 111 includes an organic acceptor; and the first hole-transport layer 112-1, the second hole-transport layer 112-2, and the third hole-transport layer 112-3 include a first hole-transport material, a second hole-transport material, and a third hole-transport material, respectively.

The HOMO level of the above host material is located at the level deeper than the HOMO level of the second hole-transport material, and the HOMO level of the second hole-transport material is located at the level deeper than the HOMO level of the first hole-transport material. The HOMO level of the third hole-transport material is located at the level deeper than or equal to the HOMO level of the host material. Note that the difference between the HOMO level of the second hole-transport material and the HOMO level of the third hole-transport material is less than or equal to 0.3 eV.

The organic acceptor is an organic compound with a deep LUMO level. When charge separation is caused between the organic acceptor and an organic compound whose HOMO level is close to the LUMO level of the organic acceptor, holes can be generated in the organic compound. That is, in the light-emitting element of this embodiment, holes are generated in the first hole-transport material in contact with the organic acceptor. As the organic acceptor, a compound including an electron-withdrawing group (a halogen group or a cyano group), e.g., 7,7,8,8-tetracyano-2,3,5,6-tetrafluoroquinodimethane (abbreviation: F$_4$-TCNQ), 3,6-difluoro-2,5,7,7,8,8-hexacyanoquinodimethane, chloranil, or 2,3,6,7,10,11-hexacyano-1,4,5,8,9,12-hexaazatriphenylene (HAT-CN), is preferably used. HAT-CN is particularly preferable because it has a high acceptor property and stable film quality.

Although the difference between the LUMO level of the organic acceptor and the HOMO level of the first hole-transport material is not particularly limited because it depends on the acceptor property of the organic acceptor, holes can be injected when the difference between the levels is approximately less than or equal to 1 eV. Since the LUMO level of HAT-CN is estimated to be −4.41 eV by cyclic voltammetry measurement, in the case where HAT-CN is used as the organic acceptor, the HOMO level of the first hole-transport material is preferably greater than or equal to −5.4 eV. Note that if the HOMO level of the first hole-transport material is too high, the hole-injection property for the second hole-transport material is poor. In addition, since the work function of an anode such as ITO is approximately −5 eV, the use of the first hole-transport material whose HOMO level is higher than −5 eV brings a disadvantage. Therefore, the HOMO level of the first hole-transport material is preferably less than or equal to −5.0 eV.

Holes generated in the first hole-transport material are moved toward the second electrode 102 by an electric field and injected into the second hole-transport layer 112-2. The second hole-transport material included in the second hole-transport layer 112-2 is preferably a triarylamine compound having a structure where a dibenzofuran skeleton or a dibenzothiophene skeleton is bonded to nitrogen of an amine directly or via a divalent aromatic hydrocarbon group, because the reliability of the light-emitting element becomes favorable.

The triarylamine compound that is the second hole-transport material is preferably a substance in which a dibenzofuran skeleton or a dibenzothiophene skeleton is bonded to nitrogen of an amine directly or via a divalent aromatic hydrocarbon group, because an optical band gap is wide and the triarylamine compound does not easily have absorption in the visible region. Furthermore, such a substance has a relatively deep HOMO level of approximately −5.4 eV to −5.7 eV and thus is suitable as the second hole-transport material. Note that in this specification, aryls of the triarylamine include heteroaryls.

Furthermore, the triarylamine compound that is the second hole-transport material is preferably a substance in which the 4-position of a dibenzofuran skeleton or the 4-position of a dibenzothiophene skeleton is bonded to nitrogen of an amine directly or via a divalent aromatic hydrocarbon group, because the synthesis is easy. In addition, the HOMO level tends to be lower (deeper) than that of a 2-position substituted compound, which is preferable.

Note that the divalent aromatic hydrocarbon group in the triarylamine compound is preferably a divalent aromatic hydrocarbon group having 6 nuclear atoms to 18 carbon atoms.

The triarylamine compound that is the second hole-transport material can also be represented as an organic compound having a partial structure represented by General Formula (g1-1) shown below.

[Chemical Formula 15]

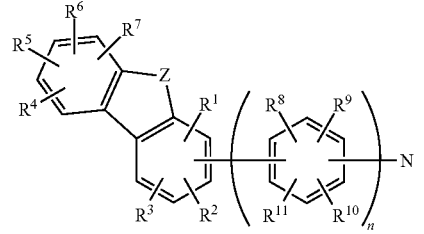

(g1-1)

Note that in General Formula (g1-1), Z represents an oxygen atom or a sulfur atom. Further, n represents an integer of 0 to 3. In addition, each of $R^1$ to $R^{11}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

As described above, in the organic compound that is the second hole-transport material, it is preferable that the dibenzofuran skeleton or the dibenzothiophene skeleton be bonded to nitrogen of an amine at the 4-position directly or via a divalent aromatic hydrocarbon group.

That is, an organic compound having a partial structure represented by General Formula (g1-2) shown below is preferable.

[Chemical Formula 16]

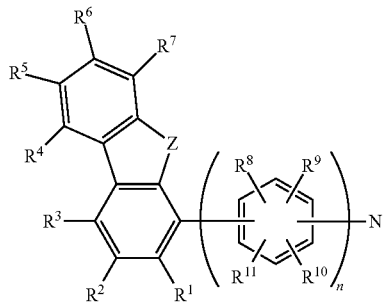

(g1-2)

Note that Z, n, and $R^1$ to $R^{11}$ in General Formula (g1-2) are the same as those in General Formula (g1-1).

Note that when the second hole-transport material is a monoamine instead of a diamine, the HOMO level is moderately deep, and thus, the second hole-transport material can be more suitably used as the light-emitting element of this embodiment.

Note that more specifically, the second hole-transport material is preferably an organic compound represented by General Formula (G1-1) shown below.

[Chemical Formula 17]

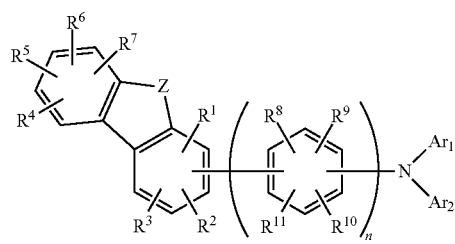

(G1-1)

Note that Z, n, and $R^1$ to $R^{11}$ in General Formula (G1-1) are the same as those in General Formula (g1-1). In addition, $Ar^1$ represents any one of aromatic hydrocarbon groups having 6 to 18 nuclear atoms, and $Ar^2$ is any one of an aromatic hydrocarbon group having 6 to 18 nuclear atoms and a group represented by General Formula (g2-1) shown below.

[Chemical Formula 18]

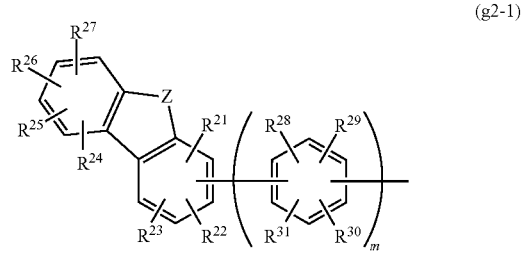

(g2-1)

Note that in General Formula (g2-1), Z represents an oxygen atom or a sulfur atom, and m represents an integer of 0 to 3. In addition, each of $R^{21}$ to $R^{31}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms.

As described above, in the second hole-transport material, the dibenzofuran skeleton or the dibenzothiophene skeleton is preferably bonded to nitrogen of an amine at the 4-position directly or via a divalent aromatic hydrocarbon group.

That is, another embodiment of the present invention is preferably an organic compound represented by General Formula (G1-2) shown below.

[Chemical Formula 19]

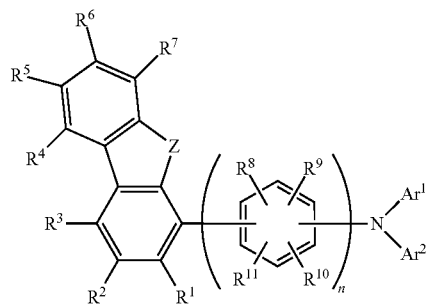

(G1-2)

Note that Z, n, $R^1$ to $R^{10}$, and $Ar^1$ in General Formula (G1-2) are the same as those in General Formula (G1-1) shown above. In addition, $Ar^2$ is any one of an aromatic hydrocarbon group having 6 to 18 nuclear atoms and a group represented by General Formula (g2-2) shown below.

[Chemical Formula 20]

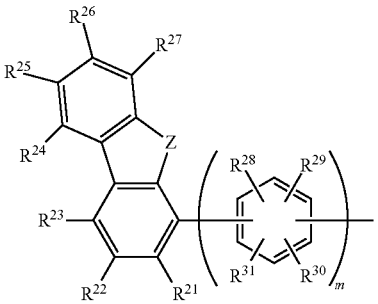

(g2-2)

In General Formula (g2-2), Z, m, and $R^{21}$ to $R^{31}$ are the same as those in General Formula (g2-1) shown above.

In this specification, as a saturated hydrocarbon group having 1 to 6 carbon atoms, specifically, a methyl group, an ethyl group, a propyl group, an isopropyl group, an n-butyl group, a sec-butyl group, an isobutyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a branched or non-branched hexyl group, and the like can be given.

As a cyclic saturated hydrocarbon group having 3 to 6 carbon atoms, a cyclopropyl group, a cyclobutyl group, a cyclopentyl group, a cyclohexyl group, and the like can be given.

As an aromatic hydrocarbon group having 1 to 18 carbon atoms, a phenyl group, a biphenyl group, a terphenyl group, a naphthyl group, a fluorenyl group, and the like can be given. When the group is a fluorenyl group, the fluorenyl group preferably includes a substituent and is more preferably a 9,9-dialkylfluorenyl group, a 9,9-dialkylfluorenyl group, or a diphenylfluorenyl group. Note that as an alkyl group of a 9,9-dialkylfluorenyl group, an alkyl group having 1 to 6 carbon atoms is preferable. As the 9,9-diarylfluorenyl group, a phenyl group is preferable, and it may be a diphenylfluorenyl group or a 9,9'-spirobifluorenyl group formed by bonding of phenyl groups.

As a divalent aromatic hydrocarbon group having 6 to 18 carbon atoms, a phenylene group, a biphenyl-diyl group, a naphthylene group, a fluorene-diyl group, and the like can be given. Note that when the group is a fluorene-diyl group, the fluorene-diyl group preferably includes a substituent, and the fluorene-diyl group is more preferably a 9,9-dialkylfluorene-diyl group or a 9,9-diphenylfluorene-diyl group. Note that as an alkyl group of the 9,9-dialkylfluorenyl group, an alkyl group having 1 to 6 carbon atoms is preferable. The 9,9-diphenylfluorene-diyl group may be a 9,9'-spirobifluorene-diyl group in which phenyl groups are bonded.

Note that in this specification, when the number of nuclear atoms in a substituent is specified, the number of atoms of a skeleton in the substituent is specified, and the substituent may further include a substituent. As the substituent in that case, a saturated hydrocarbon group having 1 to 6 carbon atoms, a cyclic saturated hydrocarbon group having 3 to 6 carbon atoms, a phenyl group, or the like can be used.

The HOMO level of the second hole-transport material included in the second hole-transport layer 112-2 is positioned between the HOMO level of the first hole-transport material and the HOMO level of the host material when the triarylamine compound or the organic compound is used as the second hole-transport material, which allows the holes to be easily injected from the first hole-transport layer 112-1 into the second hole-transport layer 112-2. Note that to smoothly inject the holes, the difference in HOMO level between the hole-transport material and the second hole-transport material is preferably less than or equal to 0.3 eV; to inject the holes more easily, the difference is further preferably less than or equal to 0.2 eV.

The holes injected into the second hole-transport layer 112-2 are moved further toward the second electrode 102 by an electric field to be injected into the third hole-transport layer 112-3. The HOMO level of the third hole-transport material included in the third hole-transport layer 112-3 is deeper than or equal to the HOMO level of the host material, and the difference in HOMO level between the third hole-transport material and the second hole-transport material is less than or equal to 0.3 eV. Since the difference between the HOMO level of the second hole-transport material and the HOMO level of the third hole-transport material is less than or equal to 0.3 eV, holes are smoothly injected from the second hole-transport layer 112-2 to the third hole-transport layer 112-3. Note that for more smooth hole injection, the difference between the HOMO level of the third hole-transport material and the HOMO level of the second hole-transport material is preferably less than or equal to 0.2 eV. Note that a hole-transport material having the HOMO level equal to that of the host material refers to a material whose HOMO level is within the range of the HOMO level of the host material ±0.1 eV, preferably ±0.05 eV.

Since the HOMO level of the third hole-transport material is deeper than or equal to the HOMO level of the host material, no barrier exists when holes are injected from the hole-transport layer 112-3 to the light-emitting layer 113. Furthermore, holes are likely to be injected directly not only into the light-emitting material but also into the host material because the HOMO level of the third hole-transport material is deeper than or equal to the HOMO level of the host material. If holes enter the light-emitting material preferentially, movement of holes in the light-emitting layer becomes extremely difficult, and a light-emitting region is localized at the interface between the hole-transport layer and the light-emitting layer, which adversely affects the element lifetime. In contrast, when holes also enter the host material as in one embodiment of the present invention, the holes are moderately influenced by hole trapping in the light-emitting material while being transferred mainly in the host in the light-emitting layer; therefore, the light-emitting region can be expanded moderately, resulting in high efficiency and long lifetime. The moderate expansion of the light-emitting region means that holes are transferred in the light-emitting layer to some extent but do not penetrate the light-emitting layer. Accordingly, it is preferable that the host material have a hole-transport property, specifically, have an anthracene skeleton or a carbazole skeleton. An anthracene skeleton is particularly suitable because it is preferable that the host material have an electron-transport property. In other words, it is further preferable that the host material have both of an anthracene skeleton and a carbazole skeleton. The carbazole skeleton is preferably a benzocarbazole skeleton or dibenzocarbazole. This is because the HOMO of these structures is higher than that of carbazole by approximately 0.1 eV, which facilitates holes' entry into the host material (as a result, the moderate expansion of the light-emitting region described above is facilitated). In this manner, including the third hole-transport layer 112-3 is one of the features of the light-emitting element of one embodiment of the present invention.

Here, in the case where the HOMO level of the light-emitting material is shallower than the HOMO level of the host material, when holes are injected into the light-emitting layer from the hole-transport material whose HOMO level is shallower than that of the host material, the holes are injected preferentially into the light-emitting material over into the host material. When holes are injected into the light-emitting material with a shallow HOMO level, the holes are trapped. The trap of holes inhibits holes from flowing, which causes problems such as accumulation of charge, acceleration of deterioration of the light-emitting layer due to localization of a recombination region, and reduction in luminous efficiency.

In contrast, in a light-emitting element which includes the third hole-transport layer 112-3 and in which the HOMO level of the third hole-transport layer 112-3 is deeper than or equal to the HOMO level of the host material as in the light-emitting element of this embodiment, holes are preferentially injected into the host material, not into the light-emitting material. As a result, the flow of holes is not inhibited, holes are moderately trapped in the light-emitting material, and the recombination region is dispersed, which results in various effects such as improvements in the reliability and luminous efficiency.

Next, examples of detailed structures and materials of the above light-emitting element are described. As described above, the light-emitting element of one embodiment of the present invention includes the EL layer 103 composed of a plurality of layers, between the pair of electrodes, the first electrode 101 and the second electrode 102, and the EL layer 103 includes at least the hole-injection layer 111, the first hole-transport layer 112-1, the second hole-transport layer 112-2, the third hole-transport layer 112-3, and the light-emitting layer 113 from the first electrode 101 side.

There is no particular limitation on the other layers included in the EL layer 103, and various layer structures such as a hole-injection layer, a hole-transport layer, an electron-injection layer, a carrier-blocking layer, an exciton-blocking layer, and a charge generation layer can be employed.

Since the first electrode 101 is preferably formed using a metal, an alloy, a conductive compound with a high work function (specifically, 4.0 eV or more), a mixture thereof, and the like. Specific examples include indium oxide-tin oxide (ITO: Indium Tin Oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 to 20 wt % of zinc oxide to indium oxide. Furthermore, indium oxide containing tungsten oxide and zinc oxide (IWZO) can be deposited by a sputtering method using a target in which tungsten oxide and zinc oxide are added to indium oxide at 0.5 to 5 wt % and 0.1 to 1 wt %, respectively. In addition, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be given. Graphene can also be used. Note that when a composite material described later is used for a layer which is in contact with the first electrode 101 in the EL layer 103, an electrode material can be selected regardless of its work function.

Figure 1B:
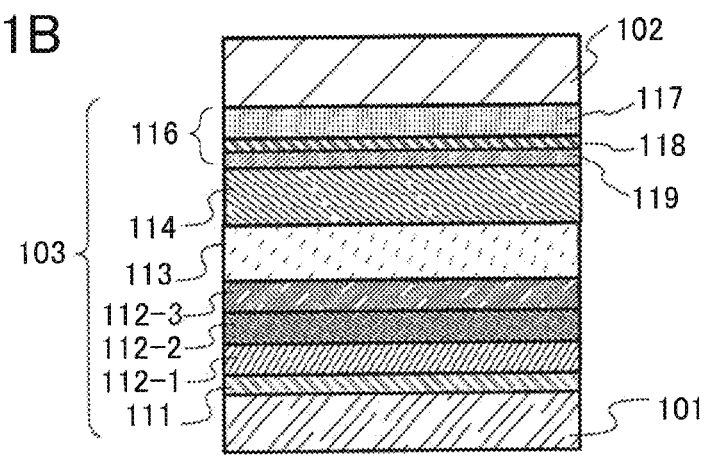

As two kinds of stacked-layer structures of the EL layer 103, a structure which includes the electron-transport layer 114 and the electron-injection layer 115 in addition to the hole-injection layer 111, the first hole-transport layer 112-1, the second hole-transport layer 112-2, the third hole-transport layer 112-3, and the light-emitting layer 113 as illustrated in FIG. 1(A), and a structure which includes the electron-transport layer 114 and a charge generation layer 116 in addition to the hole-injection layer 111, the first hole-transport layer 112-1, the second hole-transport layer 112-2, the third hole-transport layer 112-3, and the light-emitting layer 113 as illustrated in FIG. 1(B) are described in this embodiment. Materials for forming the layers are specifically described below.

The hole-injection layer 111 is a layer including an organic acceptor. As the organic acceptor, a compound including an electron-withdrawing group (a halogen group or a cyano group), e.g., 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, or 2,3,6,7,10,11-hexacyano-1,4,5,8,9,12-hexaazatriphenylene (HAT-CN), can be used. A compound in which electron-withdrawing groups are bonded to a condensed aromatic ring having a plurality of hetero atoms, like HAT-CN, is preferable as the organic acceptor because it is thermally stable. The organic acceptor can extract an electron from an adjacent hole-transport layer (or hole-transport material) by at least application of an electric field.

Forming the hole-injection layer 111 improves the hole-injection property, and thus, a light-emitting element that is driven at a low voltage can be obtained. In addition, the organic acceptor is a material that is easy to use because it is easily formed by evaporation.

The first hole-transport layer 112-1, the second hole-transport layer 112-2, and the third hole-transport layer 112-3 form a hole-transport layer. The first hole-transport layer 112-1 to the third hole-transport layer each include a hole-transport material with a hole-transport property; the first hole-transport layer 112-1 includes the first hole-transport material, the second hole-transport layer 112-2 includes the second hole-transport material, and the third hole-transport layer 112-3 includes the third hole-transport material. The hole-transport materials preferably have a hole mobility of higher than or equal to $1 \times 10^{-6}$ cm$^2$/Vs. The following relationships are satisfied between these materials: the HOMO level of the second hole-transport material is deeper than the HOMO level of the first hole-transport material, the HOMO level of the host material included in the light-emitting layer 113 is deeper than the HOMO level of the second hole-transport material, the HOMO level of the third hole-transport material is deeper than or equal to the HOMO level of the host material, and the difference between the HOMO level of the second hole-transport material and the HOMO level of the third hole-transport material is less than or equal to 0.3 eV. Note that the difference between the HOMO level of the second hole-transport material and the HOMO level of the third hole-transport material is preferably less than or equal to 0.2 eV.

As the first hole-transport material, a hole-transport material with a relatively shallow HOMO level is preferably used, and as such an organic compound, a substance which is a triarylamine and has a fluorenylamine skeleton is preferable.

As the third hole-transport material, a hole-transport material with a relatively deep HOMO level is preferably used. Since an organic compound including an amine tends to have a shallow HOMO level, a hole-transport material without an amine is preferable. Note that as such a hole-transport material, a hole-transport material having a carbazole skeleton is preferable. An organic compound having a carbazole skeleton and a triphenylene skeleton, an organic compound having a carbazole skeleton and a phenanthrene skeleton, an organic compound having a carbazole skeleton and a naphthalene skeleton, and the like can be suitably used.

The second hole-transport material is described above in detail and thus is not described repeatedly. Refer to the corresponding description above.

The light-emitting layer 113 is a layer including the host material and the light-emitting material. As the light-emitting material, any of fluorescent materials, phosphorescent materials, substances exhibiting thermally activated delayed fluorescence (TADF) may be used. Furthermore, the light-emitting layer 113 may be a single layer or formed of a plurality of layers containing different light-emitting materials. Note that in one embodiment of the present invention, the light-emitting layer 113 can be suitably used in the case where it is a layer that emits fluorescence, specifically, a layer that emits blue fluorescence.

Examples of a material which can be used as a fluorescent substance in the light-emitting layer 113 are as follows. Fluorescent substances other than those given below can also be used.

Examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), (N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-dia mine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-pheny lenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyidibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-pheylanthracen-2-amine (abbreviation: 2YGABPhA), N,N,9-triphenylanthracen-9-amine (abbreviation: DPhAPhA), coumarin 545T, N,N'-diphenylquinacridone, (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'=tetrakis(4-methylphenyl)tetracene-5,11-diamine (abbreviation: p-mPhTD), 7,14-diphenyl-N,N,N',N'-tetrakis(4-methylphenyl)acenaptho[1,2-a]fluoranthene-3,10-d iamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinoli zin-9-yl)ethenyl]-4H-pyran-4-ylidene}propanedinitrile (abbreviation: BisDCJTM). Condensed aromatic diamine compounds typified by pyrenediamine compounds such as 1,6FLPAPrn and 1,6mMemFLPAPrn are particularly preferable because of their high hole-trapping properties, high emission efficiency, and high reliability.

Examples of a material which can be used as a phosphorescent substance in the light-emitting layer 113 are as follows.

Organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]), organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]), organometallic iridium complexes having imidazole skeletons, such as fac-tris[(1-2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]), and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIracac) can be given. These are compounds emitting blue phosphorescence and have an emission peak at 440 nm to 520 nm.

In addition, organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]), organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]), organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)

$_3$]), and bis(2-phenylquinolinato-N,C$^{2'}$)iridium(III) acetylacetonate (abbreviation: [Ir(pq)$_2$(acac)]), and rare earth metal complexes such as tris(acetylacetonato)(monophenanthroline)terbium(III) (abbreviation: [Tb(acac)$_3$ (Phen)]) can be given. These are mainly compounds emitting green phosphorescence and have an emission peak at 500 nm to 600 nm. Note that organometallic iridium complexes having pyrimidine skeletons have distinctively high reliability and emission efficiency and thus are especially preferable.

In addition, organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]), organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$ (dpm])]), and (acetylacetonato)bis[2,3-bis(4-fluorophenyl)quinoxalinato]iridium(III) (abbreviation: [Ir(Fdpq)$_2$(acac)]), organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N, C$^{2'}$)iridium(III) acetylacetonate (abbreviation: [Ir(piq)$_2$ (acac)]), platinum complexes such as 2,3,7,8,12,13,17,18-octaethyl-21H,23H-porphyrin platinum(II) (abbreviation: PtOEP), and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline) europium(III) (abbreviation: [Eu(TTA)$_3$(Phen)]) can be given. These are compounds emitting red phosphorescence and have an emission peak at 600 nm to 700 nm. Furthermore, organometallic iridium complexes having pyrazine skeletons can provide red light emission with favorable chromaticity.

As well as the above phosphorescent compounds, known phosphorescent materials may be selected and used.

As the TADF material, a fullerene, a derivative thereof, an acridine derivative such as proflavine, eosin, or the like can be used. In addition, a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$ (Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are shown in the following structural formulae.

[Chemical Formulae 21]

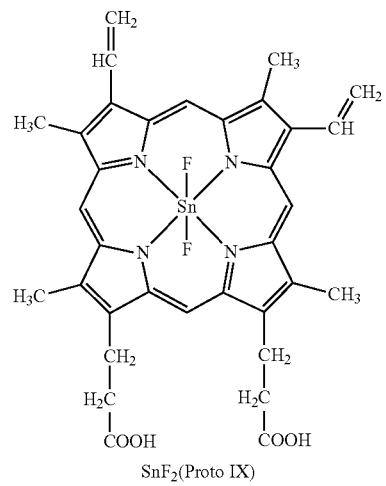

SnF$_2$(Proto IX)

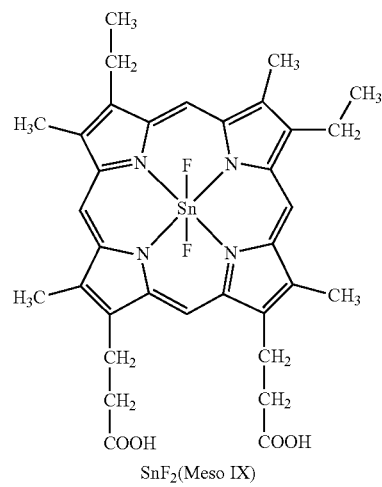

SnF$_2$(Meso IX)

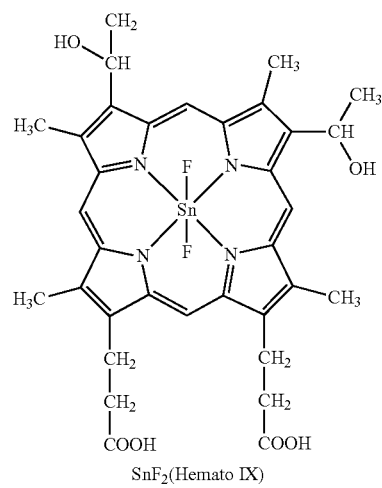

SnF$_2$(Hemato IX)

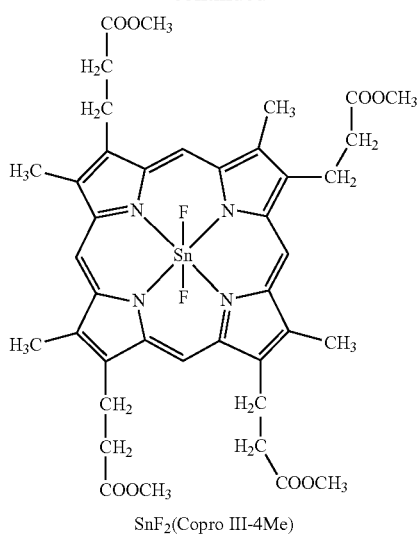

SnF₂(Copro III-4Me)

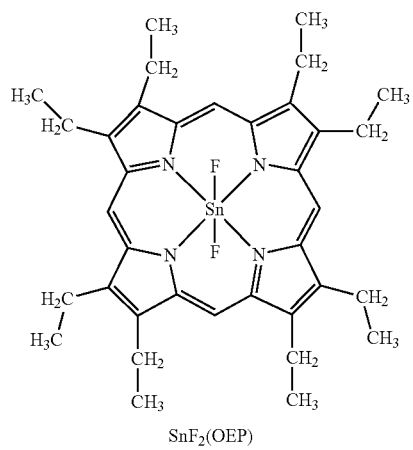

SnF₂(OEP)

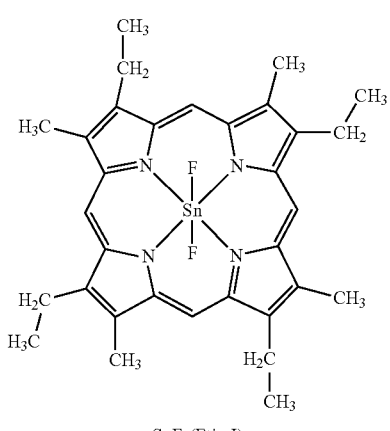

SnF₂(Etio I)

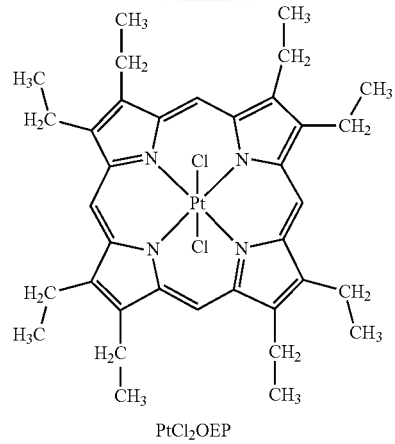

PtCl₂OEP

Alternatively, a heterocyclic compound having both of a π-electron rich heteroaromatic ring and a π-electron deficient heteroaromatic ring, such as 2-biphenyl-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 9-[4-(4,6-diphenyl-1,3,5-triazin-2-yl)phenyl]-9'-phenyl-9H, 9'H-3,3'-bicarbazole (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H, 10'H-spiro[acridin-9,9'-anthracen]-10'-one (abbreviation: ACRSA) shown in the following structural formulae, can be used. The heterocyclic compound, which has the π-electron rich heteroaromatic ring and the π-electron deficient heteroaromatic ring, is preferable because the electron-transport property and the hole-transport property are high. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both increased, the energy difference between the $S_1$ level and the $T_1$ level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring.

[Chemical Formulae 22]
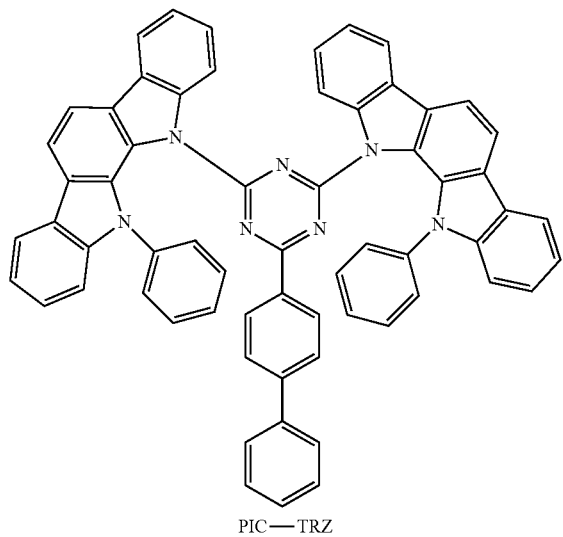
PIC—TRZ
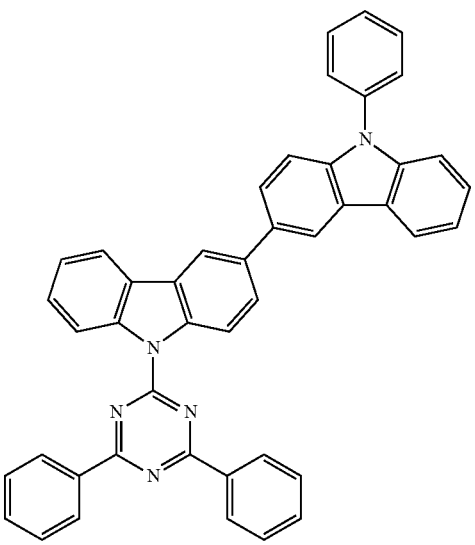
PCCzTzn
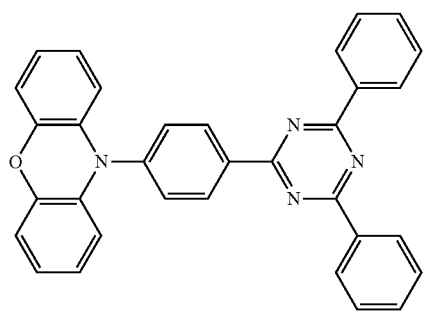
PXZ—TRZ
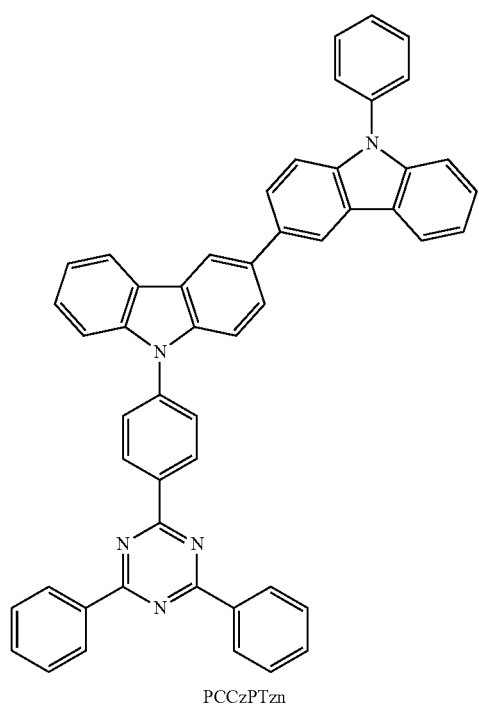
PCCzPTzn
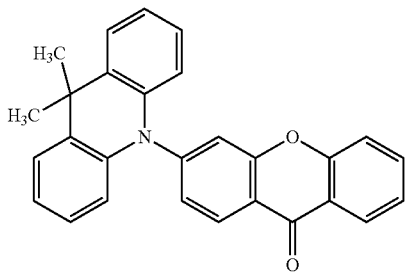
ACRXTN
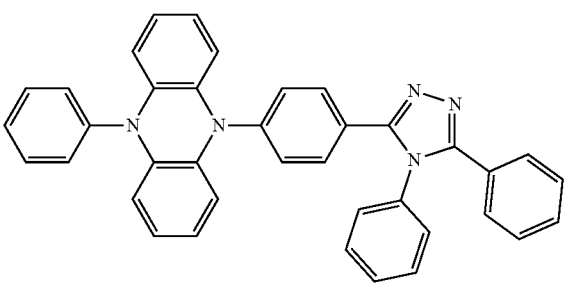
PPZ—3TPT

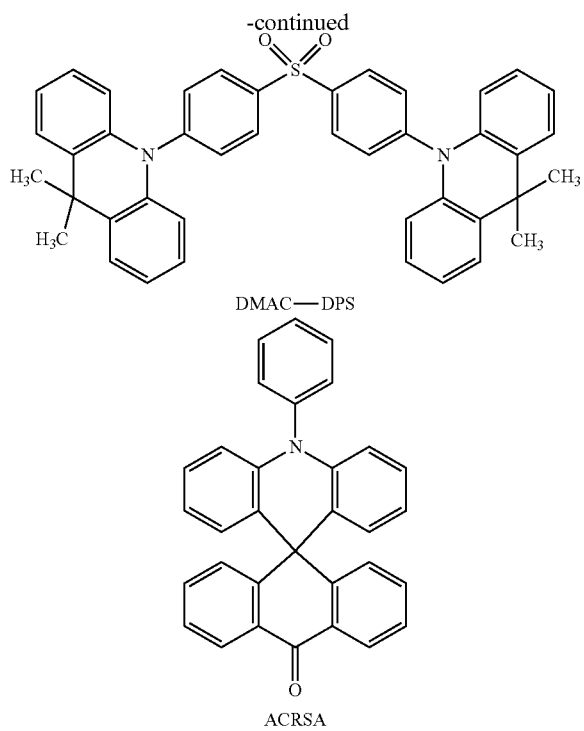

DMAC—DPS

ACRSA

As the host material of the light-emitting layer, various carrier-transport materials such as materials with an electron-transport property and materials with a hole-transport property can be used.

As materials having a hole-transport property, compounds having aromatic amine skeletons, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9-H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2-amine (abbreviation: PCBAF), and N-phenyl-N-[4-(9-phenyl-9H-carbazol-3-yl)phenyl]-spiro-9,9'-bifluoren-2-amine (abbreviation: PCBASF), compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP), compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II) can be given. Among the above, the compounds having aromatic amine skeletons and the compounds having carbazole skeletons are preferred because these compounds are highly reliable, have a high hole-transport property, and contribute to a reduction in drive voltage.

Examples of materials having an electron-transport property include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ), heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II), heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Prn), and 4,6-bis[3-(4-dibenzothienyl)phenyl]pyrimidine (abbreviation: 4,6mDBTP2Prn-II), and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)-phenyl]benzene (abbreviation: TmPyPB). Among the above, the heterocyclic compounds having diazine skeletons and the heterocyclic compounds having pyridine skeletons are highly reliable and preferred. In particular, the heterocyclic compounds having diazine (pyrimidine or pyrazine) skeletons have a high electron-transport property and contribute to a decrease in drive voltage.

In the case where a fluorescent substance is used as the light-emitting material, a material having an anthracene skeleton is suitable as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, one embodiment of the present invention can be suitably used. As the substance having an anthracene skeleton used as the host material, a substance with a diphenylanthracene skeleton, in particular, a 9,10-diphenylanthracene skeleton, is preferable because it is chemically stable. The host material preferably has a carbazole skeleton because the hole-injection and hole-transport properties are increased, and the host material further preferably has a benzocarbazole skeleton in which a benzene ring is further condensed to carbazole because the HOMO becomes higher than that of carbazole by approximately 0.1 eV and thus holes enter the host material easily. In particular, the host material suitably includes a dibenzocarbazole skeleton because the HOMO becomes higher than that of carbazole by approximately 0.1 eV, so that holes enter the host material easily, the hole-transport property is improved, and the heat resistance is increased. Accordingly, a substance which has both of a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN) 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}anthracene (abbreviation: FLPPA). In particular, CzPA, cgDBCzPA, 2mBnfPPA, and PCzPA are preferable choices because of their excellent characteristics.

Note that the light-emitting element of one embodiment of the present invention is preferably applied to, in particular, a light-emitting element that emits blue fluorescence.

Note that the host material may be a mixed material of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property is acceptable as long as the material having a hole-transport property: the material having an electron-transport property=1:9 to 9:1.

Furthermore, an exciplex may be formed by these mixed materials. It is preferable that the combination of these materials be selected to form an exciplex that exhibits light emission whose wavelength overlaps with the wavelength of a lowest-energy-side absorption band of the light-emitting material, in which case energy is transferred smoothly, light emission can be obtained efficiently, and the drive voltage is reduced.

The electron-transport layer 114 is a layer containing a substance with an electron-transport property. As the substance having an electron-transport property, it is possible to use the above-listed substances having electron-transport properties that can be used as the host material.

An alkali metal, an alkaline earth metal, or a compound thereof such as lithium fluoride (LiF), cesium fluoride (CsF), or calcium fluoride (CaF$_2$) may be provided as the electron-injection layer 115 between the electron-transport layer 114 and the second electrode 102. An electrode or a layer that is formed using a substance having an electron-transport property and that contains an alkali metal, an alkaline earth metal, or a compound thereof can be used. Examples of the electrode include a substance in which electrons are added at high concentration to a mixed oxide of calcium and aluminum.

Instead of the electron-injection layer 115, the charge generation layer 116 may be provided (FIG. 1(B)). The charge generation layer 116 refers to a layer capable of injecting holes into a layer in contact with the cathode side of the charge generation layer 116 and electrons into a layer in contact with the anode side thereof when a potential is applied. The charge generation layer 116 includes at least a P-type layer 117. The P-type layer 117 is preferably formed using the composite materials given above as materials that can be included in the hole-injection layer 111. The P-type layer 117 may be formed by stacking a film containing the above acceptor material as a material included in the composite material and a film containing a hole-transport material. When a potential is applied to the P-type layer 117, electrons are injected into the electron-transport layer 114 and holes are injected into the second electrode 102 serving as a cathode; thus, the light-emitting element operates.

Note that the charge generation layer 116 preferably includes either an electron-relay layer 118 or an electron-injection buffer layer 119 or both in addition to the P-type layer 117.

The electron-relay layer 118 contains at least the substance having an electron-transport property and has a function of preventing an interaction between the electron-injection buffer layer 119 and the P-type layer 117 and smoothly transferring electrons. The LUMO level of the substance having an electron-transport property contained in the electron-relay layer 118 is preferably between the LUMO level of the substance having an acceptor property in the P-type layer 117 and the LUMO level of a substance contained in a layer of the electron-transport layer 114 in contact with the charge generation layer 116. As a specific energy level, the LUMO level of the substance having an electron-transport property in the electron-relay layer 118 is higher than or equal to −5.0 eV, preferably higher than or equal to −5.0 eV and lower than or equal to −3.0 eV. Note that as the substance having an electron-transport property used in the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above material included in the electron-transport layer 114 can be used for formation.

As a substance included in the second electrode 102, a metal, an alloy, an electrically conductive compound, and a mixture thereof which have a low work function (specifically, 3.8 eV or less) or the like can be used. Specific examples of such a cathode material are elements belonging to Groups 1 and 2 of the periodic table, such as alkali metals, e.g., lithium (Li) and cesium (Cs), magnesium (Mg), calcium (Ca), and strontium (Sr), alloys thereof (MgAg and AlLi), rare earth metals such as europium (Eu) and ytterbium (Yb), alloys thereof, and the like. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function.

Films of these conductive materials can be formed by a dry method such as a vacuum evaporation method or a sputtering method, an inkjet method, a spin coating method, or the like. In addition, the conductive materials may be formed by a wet method using a sol-gel method, or by a wet method using paste of a metal material.

A variety of methods can be used to form the EL layer 103 regardless of whether the method is a dry method or a wet method. For example, a vacuum evaporation method, a gravure printing method, an offset printing method, a screen printing method, an inkjet method, a spin coating method, or the like may be used.

Different methods may be used to form the electrodes or the layers described above.

Note that the structure of the layers provided between the first electrode 101 and the second electrode 102 is not limited to the above structure. However, a light-emitting region where holes and electrons recombine is preferably positioned away from the first electrode 101 and the second electrode 102 so that quenching due to the proximity of the light-emitting region and a metal used for electrodes and carrier-injection layers can be prevented.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using the light-emitting material included in the light-emitting layer or a material having a wider band gap than the light-emitting material of the light-emitting layer.

Next, an embodiment of a light-emitting element with a structure in which a plurality of light-emitting units are stacked (also referred to as a stacked element or a tandem element) is described with reference to FIG. 1(C). This light-emitting element includes a plurality of light-emitting units between an anode and a cathode. One light-emitting unit has a structure similar to that of the EL layer 103 which is illustrated in FIG. 1(A). In other words, the light-emitting element illustrated in FIG. 1(C) is a light-emitting element including a plurality of light-emitting units; it can be said that the light-emitting element illustrated in FIG. 1(A) or FIG. 1(B) is a light-emitting element including a single light-emitting unit.

Figure 1C:
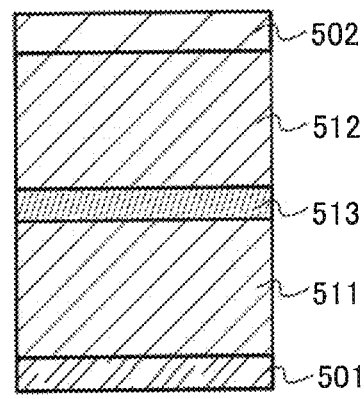

In FIG. 1(C), a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1(A), and the materials given in the description for FIG. 1(A) can be used. Furthermore, the first light-emitting unit 511 and the second light-emitting unit 512 may have the same structure or different structures.

The charge generation layer 513 has a function of injecting electrons into one of the light-emitting units and injecting holes into the other of the light-emitting units when a voltage is applied to the first electrode 501 and the second electrode 502. That is, in FIG. 1(C), the charge generation layer 513 is acceptable as long as it injects electrons into the first light-emitting unit 511 and holes into the second light-emitting unit 512 when a voltage is applied so that the potential of the first electrode becomes higher than the potential of the second electrode.

The charge generation layer 513 preferably has a structure similar to that of the charge generation layer 116 described in FIG. 1(B). Since the composite material of an organic compound and a metal oxide is superior in carrier-injection property and carrier-transport property, low-voltage driving or low-current driving can be achieved. Note that when a surface of a light-emitting unit on the anode side is in contact with the charge generation layer 513, the charge generation layer 513 can also serve as a hole-injection layer in the light-emitting unit and a hole-injection layer is not necessarily formed in the light-emitting unit.

In the case where the electron-injection buffer layer 119 is provided, the electron-injection buffer layer 119 serves as the electron-injection layer in the light-emitting unit on the anode side, and thus, an electron-injection layer is not necessarily formed in the light-emitting unit on the anode side.

The light-emitting element having two light-emitting units is described in FIG. 1(C); however, application to a light-emitting element in which three or more light-emitting units are stacked is similarly possible. With a plurality of light-emitting units partitioned by the charge generation layer 513 between a pair of electrodes as in the light-emitting element relating to this embodiment, it is possible to provide an element which can emit light with high luminance with the current density kept low and has a long lifetime. Moreover, a light-emitting device which can be driven at low voltage and has low power consumption can be manufactured.

Furthermore, when emission colors of light-emitting units are made different, light emission of a desired color can be provided from the light-emitting element as a whole. For example, in a light-emitting element having two light-emitting units, the emission colors of the first light-emitting unit may be red and green and the emission color of the second light-emitting unit may be blue, so that the light-emitting element can emit white light as the whole light-emitting element.

The above electrodes and layers such as the EL layer 103, the first light-emitting unit 511, the second light-emitting unit 512, and the charge generation layer can be formed by a method such as an evaporation method (including a vacuum evaporation method), a droplet discharge method (also referred to as an ink-jet method), a coating method, or a gravure printing method. They may further include a low molecular material, a middle molecular material (including an oligomer and a dendrimer), or a high molecular material.

Here, a method for forming an EL layer 786 by a droplet discharge method is described using FIG. 28. FIGS. 28(A) to 28(D) are cross-sectional views illustrating a method for forming the EL layer 786.

Figure 28A:
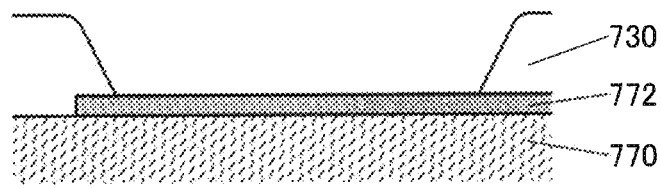
FIGS. 28A-28D are cross-sectional views illustrating a method for forming an EL layer.
Figure 28B:
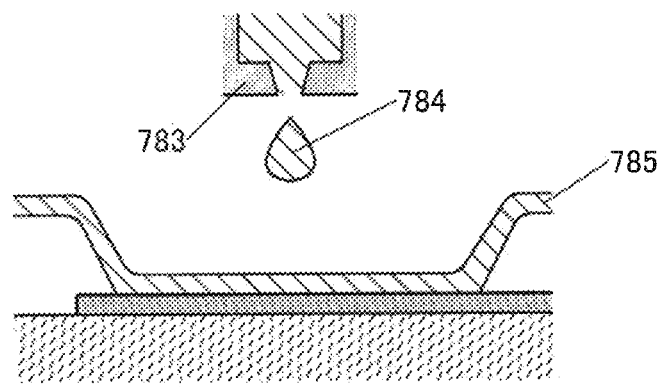

First, a conductive film 772 is formed over a planarization insulating film 770, and an insulating film 730 is formed to cover part of the conductive film 772 (see FIG. 28(A)).

Then, a droplet 784 is discharged from a droplet discharge apparatus 783 to an exposed portion of the conductive film 772 that is an opening of the insulating film 730, so that a layer 785 containing a composition is formed. The droplet 784 is a composition containing a solvent and is attached to the conductive film 772 (see FIG. 28(B)).

Note that the step of discharging the droplet 784 may be performed under reduced pressure.

Figure 28C:
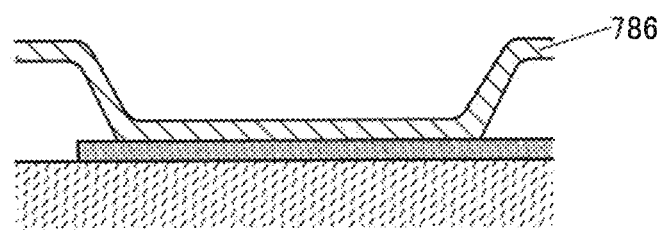

Next, the solvent is removed from the layer 785 containing a composition, and solidification is performed to form the EL layer 786 (see FIG. 28(C)).

Note that the solvent may be removed by a drying step or a heating step.

Figure 28D:
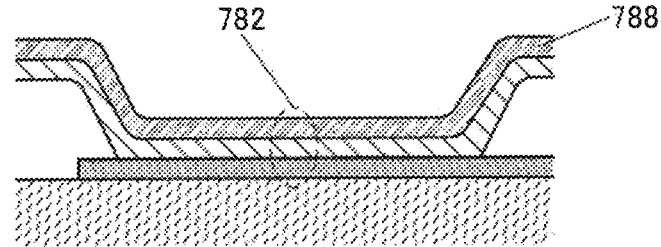

Next, a conductive film 788 is formed over the EL layer 786; thus, a light-emitting element 782 is formed (see FIG. 28(D)).

When the EL layer 786 is formed by a droplet discharge method in this manner, the composition can be selectively discharged; accordingly, waste of material can be reduced. Furthermore, a lithography process or the like for shaping is not needed, and thus, the process can be simplified and cost reduction can be achieved.

Note that the droplet discharge method mentioned above is a general term for a method with a droplet discharge means such as a nozzle having a composition discharge outlet or a head having one or a plurality of nozzles.

Figure 29:
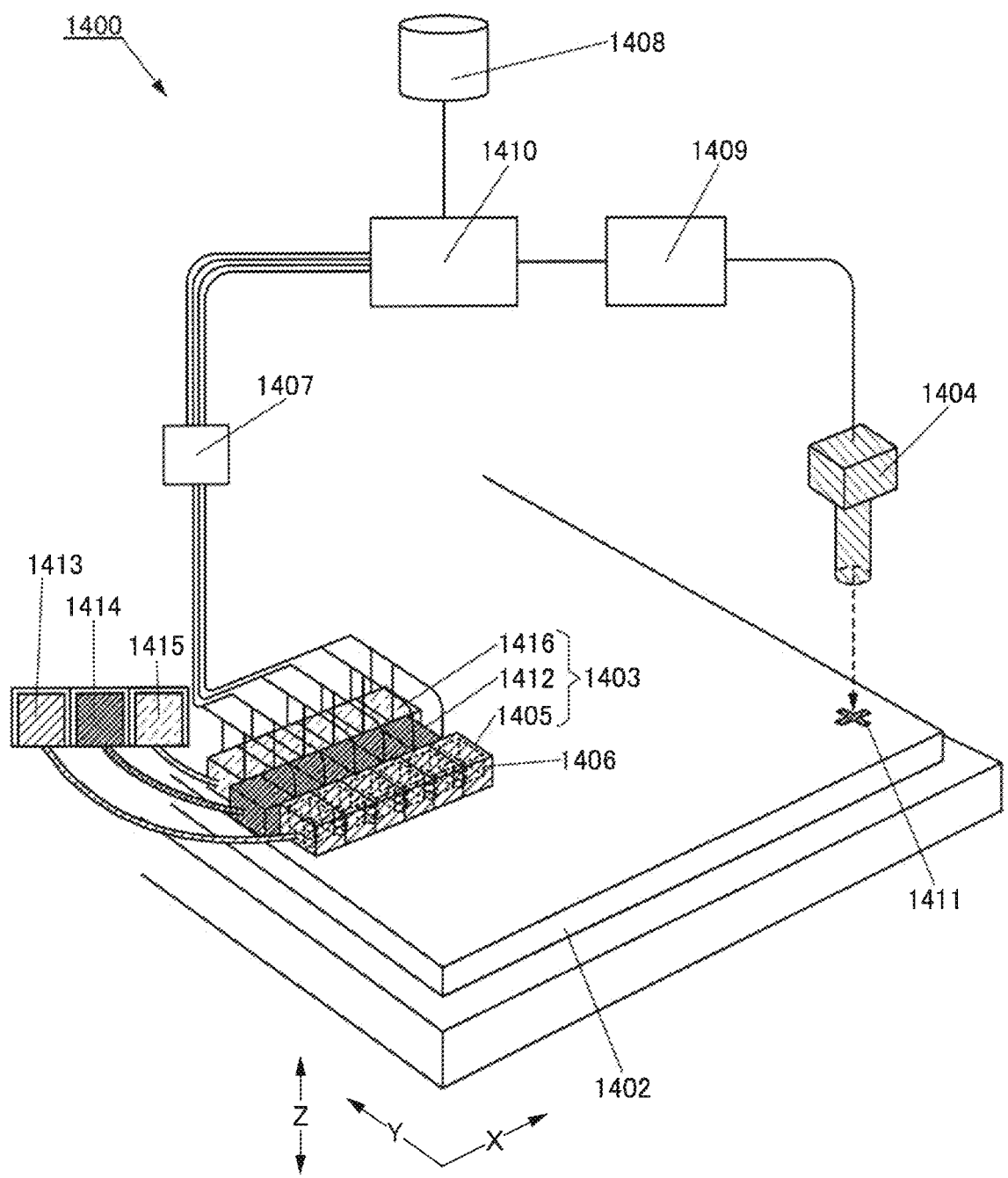
FIG. 29 is a conceptual diagram illustrating a droplet discharge apparatus.

Next, a droplet discharge apparatus used for the droplet discharge method is described using FIG. 29. FIG. 29 is a conceptual diagram illustrating a droplet discharge apparatus 1400.

The droplet discharge apparatus 1400 includes a droplet discharge means 1403. The droplet discharge means 1403 includes a head 1405, a head 1412, and a head 1416.

The heads 1405 and 1412 are connected to a control means 1407 which is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits it to the control means 1407.

An image sensor or the like using a charge coupled device (CCD) or a complementary metal oxide semiconductor (CMOS) can be used as the imaging means 1404. Note that information on a pattern to be formed on the substrate 1402 is stored in a storage medium 1408, and a control signal is transmitted to the control means 1407 on the basis of the information, so that the heads 1405, 1412, and 1416 of the droplet discharge means 1403 can be individually controlled. Materials to be discharged are supplied to the heads 1405, 1412, and 1416 from material supply sources 1413, 1414, and 1415, respectively, through pipes.

Inside each of the heads 1405, 1412, and 1416, a space indicated by a dotted line 1406 to be filled with a liquid material and a nozzle serving as a discharge outlet are provided. Although not illustrated, the inside structure of the head 1412 is similar to that of the head 1405. When the nozzle sizes of the heads 1405 and 1412 are different from each other, different materials with different widths can be drawn simultaneously. Each head can discharge a plurality of kinds of light-emitting materials or the like to draw a pattern. In the case of drawing a pattern over a large area, the same material can be simultaneously discharged from a plurality of nozzles in order to improve throughput. When a large substrate is used, the heads 1405, 1412, and 1416 can freely scan the substrate in the directions of arrows X, Y, and Z in FIG. 29, and a region in which drawing is performed can be freely set. Thus, the same patterns can be drawn on one substrate.

Furthermore, the step of discharging the composition may be performed under reduced pressure. The substrate may be heated when the composition is discharged. The discharge of the composition is followed by drying and/or baking. Both the steps of drying and baking are heat treatments but different in purpose, temperature, and time. The steps of drying and baking are performed under normal pressure or reduced pressure by laser irradiation or rapid thermal annealing, with a heating furnace, or the like. Note that there is no particular limitation on the timing of the heat treatment and the number of times of the heat treatment. The temperatures for favorably performing the steps of drying and baking depend on the material quality of the substrate and the properties of the composition.

In the above manner, the EL layer 786 can be formed with the droplet discharge apparatus.

Note that the above structure can be combined with the other embodiments and other structures in this embodiment, as appropriate.

EMBODIMENT 2

In this embodiment, an organic compound of one embodiment of the present invention is described.

Some of the organic compounds described in Embodiment 1, which can be used as the second hole-transport material, are novel compounds and therefore are embodiments of the present invention. The organic compound of one embodiment of the present invention is described below.

The organic compound of one embodiment of the present invention is represented by General Formula (G2) shown below.

[Chemical Formula 23]

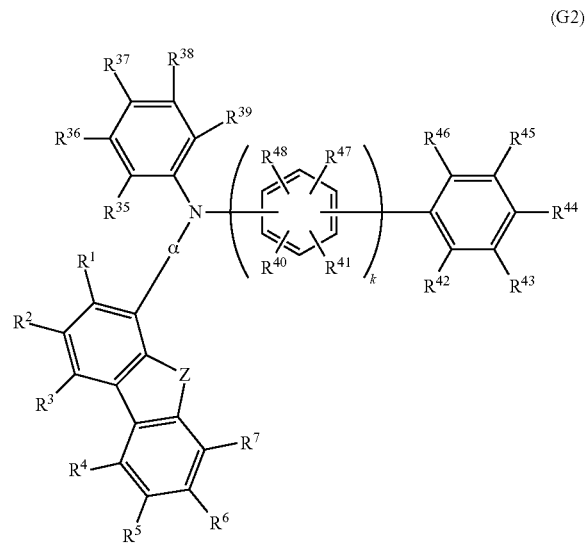

(G2)

Note that in General Formula (G2), each of $R^1$ to R7 and $R^{35}$ to $R^{48}$ independently represents any one of hydrogen, a saturated hydrocarbon group having 1 to 6 carbon atoms, a cyclic saturated hydrocarbon group having 3 to 6 carbon atoms, and an aromatic hydrocarbon group having 6 to 18 nuclear atoms. In addition, α represents a divalent aromatic hydrocarbon group having 6 nuclear atoms to 18 carbon atoms, and Z represents an oxygen atom or a sulfur atom. Further, k represents 1 or 2.

$R^{35}$ to $R^{48}$ are each preferably a saturated hydrocarbon group or a cyclic saturated hydrocarbon group, in which case they have increased solubility and are easily used for a wet method and the like. Furthermore, the substituent is preferably included because the molecular structure becomes three-dimensional, molecular interaction can be reduced, and thus, the film quality and sublimation property are improved, for example. As the substituent, a methyl group, a t-butyl group, a cyclohexyl group, a phenyl group, a tolyl group, and the like are preferable.

In the organic compound represented by (G2) shown above, k is preferably 1 because easy synthesis and low-cost manufacture are enabled. That is, an organic compound represented by General Formula (G3) shown below is preferable.

[Chemical Formula 24]

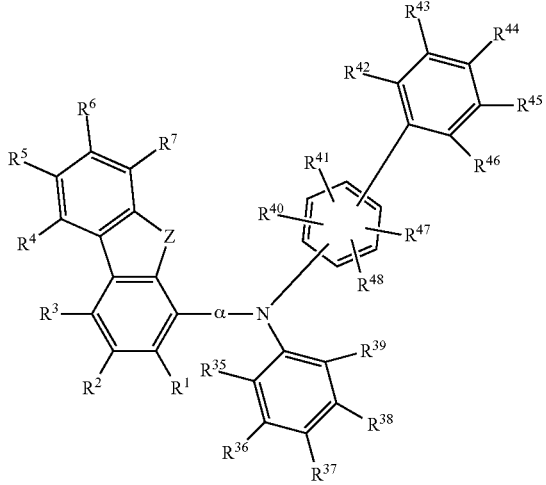

(G3)

Note that in the organic compound represented by General Formula (G3) shown above, $R^1$ to R7 and $R^{35}$ to $R^{48}$, Z, and α are similar to those in General Formula (G2) shown above.

In the organic compound represented by General Formula (G2) shown above, it is preferable that a biphenyl group and a phenyl group have no substituent because a raw material is inexpensive and the synthesis is easy, for example. That is, an organic compound represented by General Formula (G4) shown below is preferable.

[Chemical Formula 25]

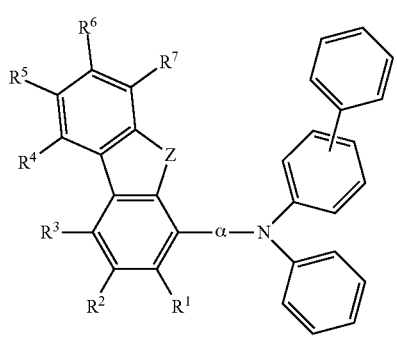

(G4)

Note that in the organic compound represented by General Formula (G4) shown above, Z, $R^1$ to $R^7$, and α are similar to those in General Formula (G2) shown above.

In General Formula (G4) shown above, Z is preferably a sulfur atom, in which case the glass transition point is higher and the heat resistance is increased. That is, an organic compound represented by General Formula (G5) shown below is preferable.

[Chemical Formula 26]

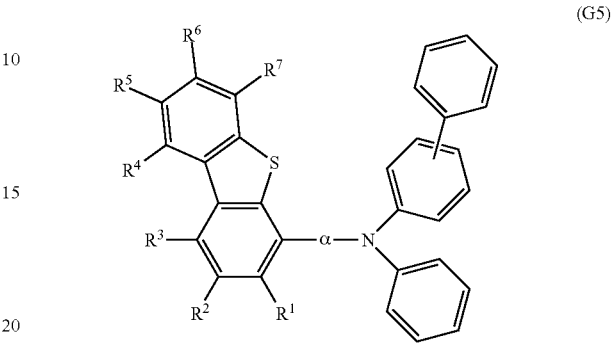

(G5)

Note that in the organic compound represented by General Formula (G5) shown above, $R^1$ to $R^7$ and α are similar to those in General Formula (G2) shown above.

Note that in the above organic compound, a is a phenylene group, a biphenylene group, a fluorenylene group, a naphthylene group, and the like. Furthermore, α may have, as substituents, a saturated hydrocarbon group having 1 to 6 carbon atoms, a cyclic saturated hydrocarbon group having 3 to 6 carbon atoms, and an aromatic hydrocarbon group having 6 to 18 nuclear atoms. The substituent is preferably a saturated hydrocarbon group or a cyclic saturated hydrocarbon group, in which case the organic compound has increased solubility and is easily used for a wet method and the like. Furthermore, the substituent is preferably included because the molecular structure becomes three-dimensional, molecular interaction can be reduced, and thus, the film quality and sublimation property are improved, for example. As the substituent, a methyl group, a t-butyl group, a cyclohexyl group, a phenyl group, a tolyl group, and the like are preferable. Note that no substituent is preferably included because low-cost and easy synthesis is enabled. It is preferable that α be the groups represented by Structural Formulae (α-1) to (α-5) shown below because an optical band gap can be kept high.

[Chemical Formulae 27]

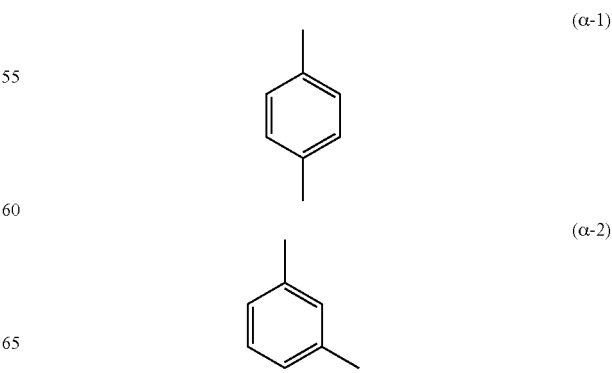

(α-3)

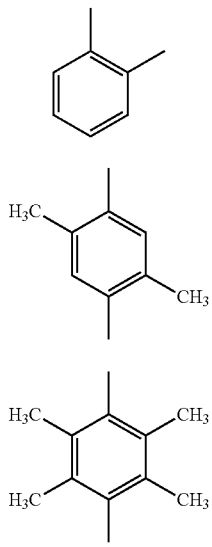

(α-4)

(α-5)

Note that the organic compounds using (α-1) and (α-2) have preferable structures because they can be easily synthesized at low cost. When (α-1) is used, the carrier-transport property is favorable, which is preferable. In addition, (α-2) to (α-5), with which the molecular structure becomes three-dimensional, are preferable because molecular interaction can be reduced and the film quality and sublimation property are improved. The organic compounds using (α-2) and (α-3) have preferable structures, in which case the triplet excitation level is higher than that of the organic compound using (α-1).

In the organic compound represented by General Formula (G5) shown above, it is preferable that α be a phenylene group without a substituent and the dibenzothiophene skeleton have no substituent, in which case a raw material is readily available or the synthesis is easy and thus the organic compound can be manufactured at low cost. That is, an organic compound represented by General Formula (G6) shown below is preferable.

[Chemical Formula 28]

(G6)

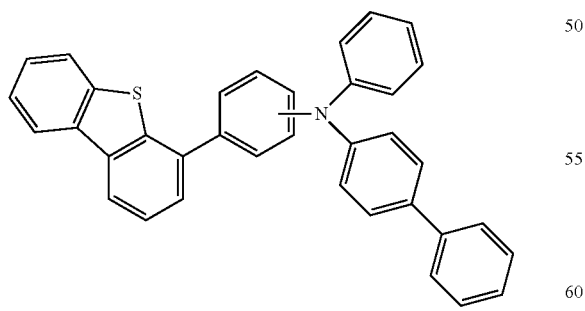

Examples of the organic compounds represented by General Formulae (G2) to (G6) shown above are as follows. Note that the following are only examples and the organic compound of the present invention is not limited to the organic compounds having the following structures.

[Chemical Formulae 29]

(100)

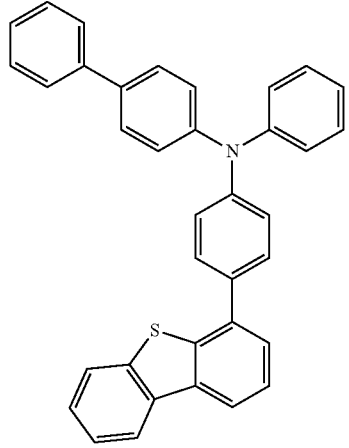

(101)

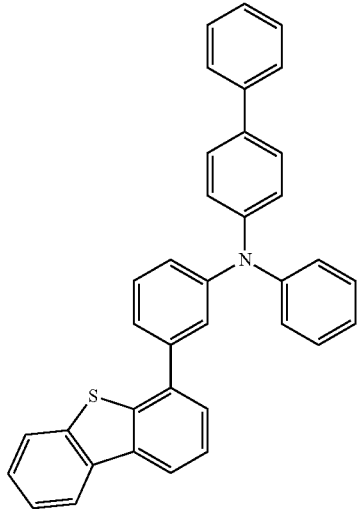

(102)

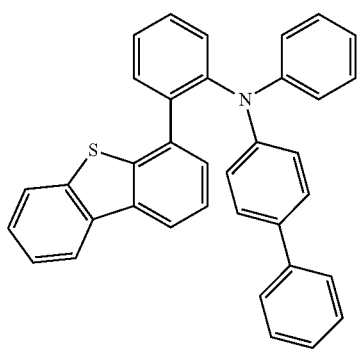

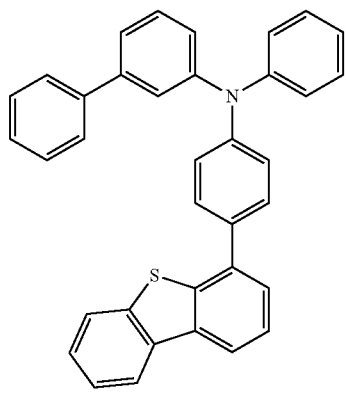 (103)
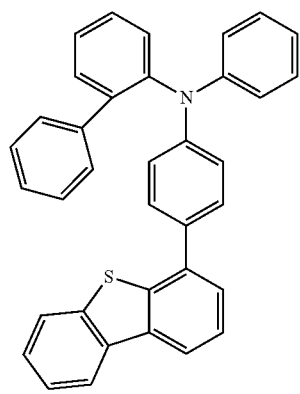 (106)
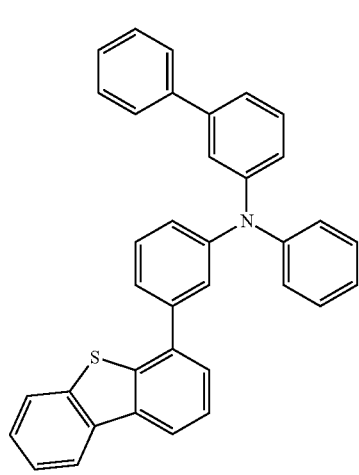 (104)
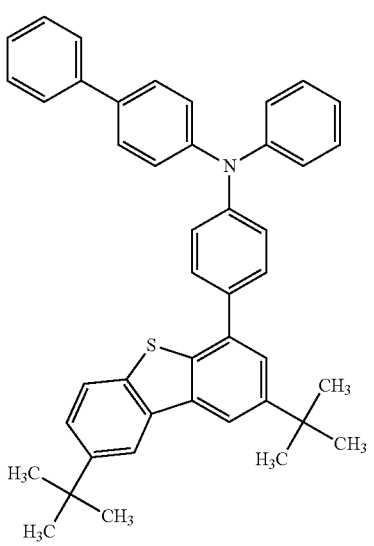 (107)
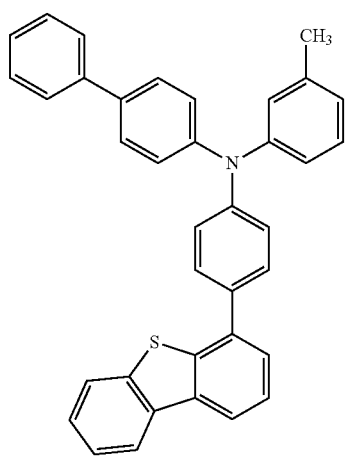 (105)
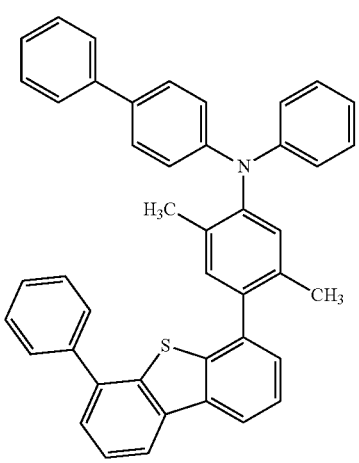 (108)

[Chemical Formulae 30]
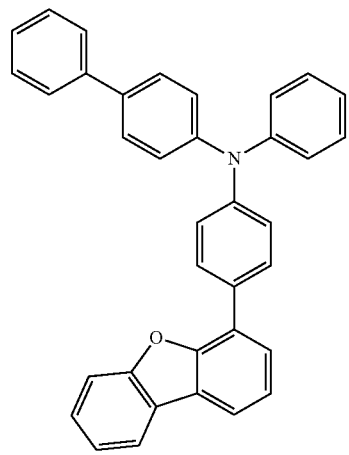 (110)
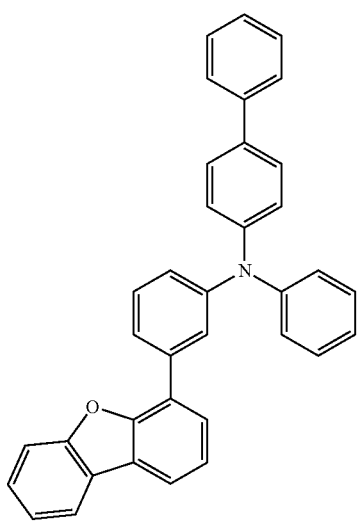 (111)
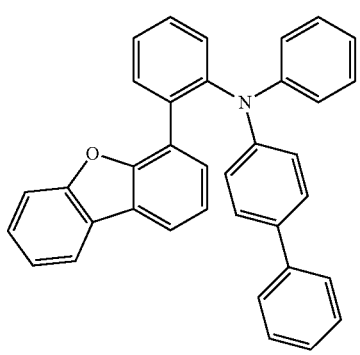 (112)
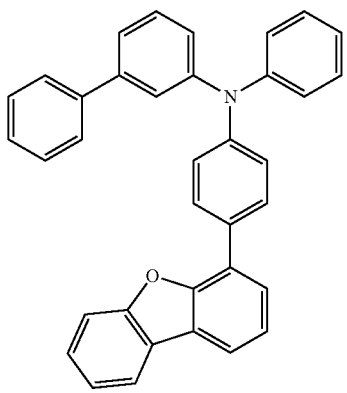 (113)
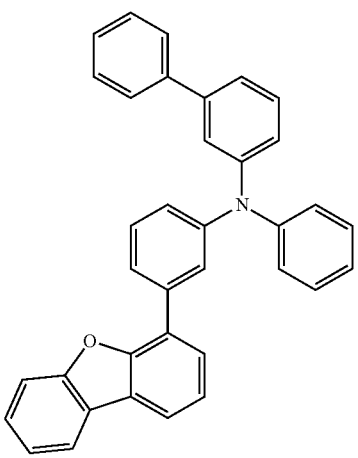 (114)
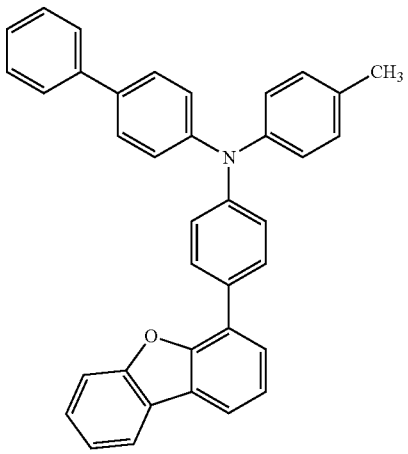 (115)

(116)

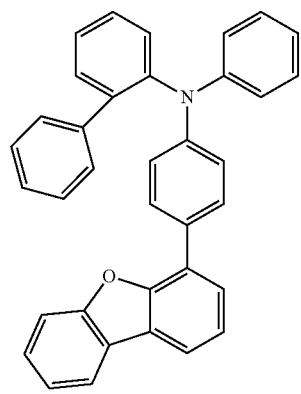

(117)

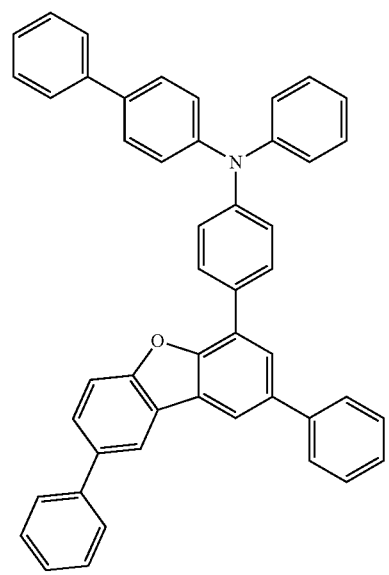

(118)

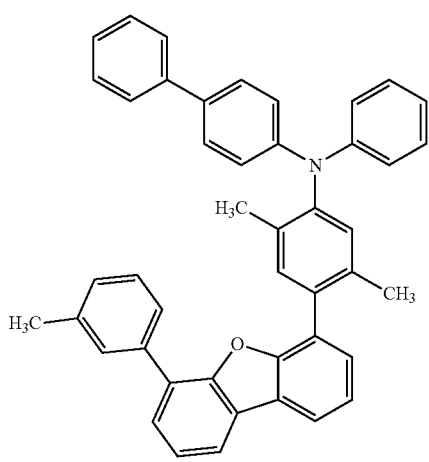

The organic compounds shown above can be synthesized by Synthesis Schemes (F-1) to (F-3) shown below.

[Chemical Formula 31]

(F-1)

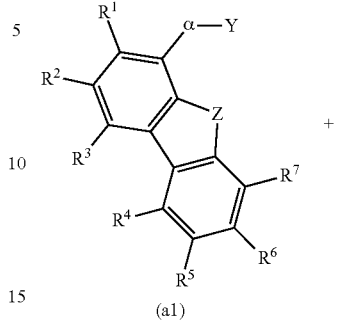

(a1)

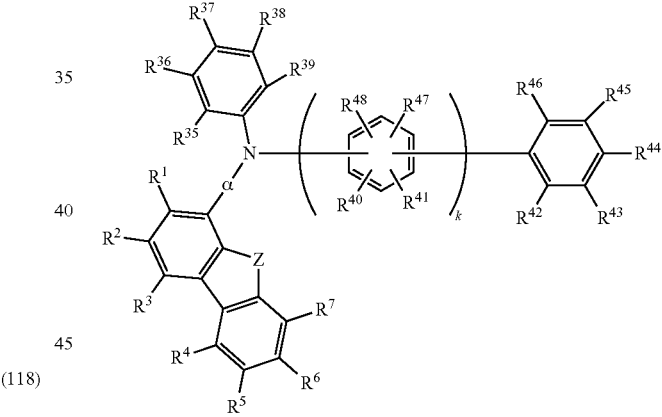

In Synthesis Scheme (F-1), Y represents a halogen atom and is preferably iodine, bromine, and chlorine in this order in terms of high reactivity. Alternatively, Y may be triflate.

In this synthesis scheme, a coupling reaction of a halide represented by (a1) and an amine compound represented by (a2) is caused, whereby the amine compound represented by (G2) can be synthesized.

A variety of reaction conditions can be used in performing the synthesis, and a synthesis method using a metal catalyst in the presence of a base can be used as an example. Specifically, the Buchwald-Hartwig reaction or the Ullmann reaction can be used.

This reaction is preferably performed under an inert atmosphere of nitrogen, argon, or the like. Further, heating may be performed using electromagnetic waves.

[Chemical Formula 32]

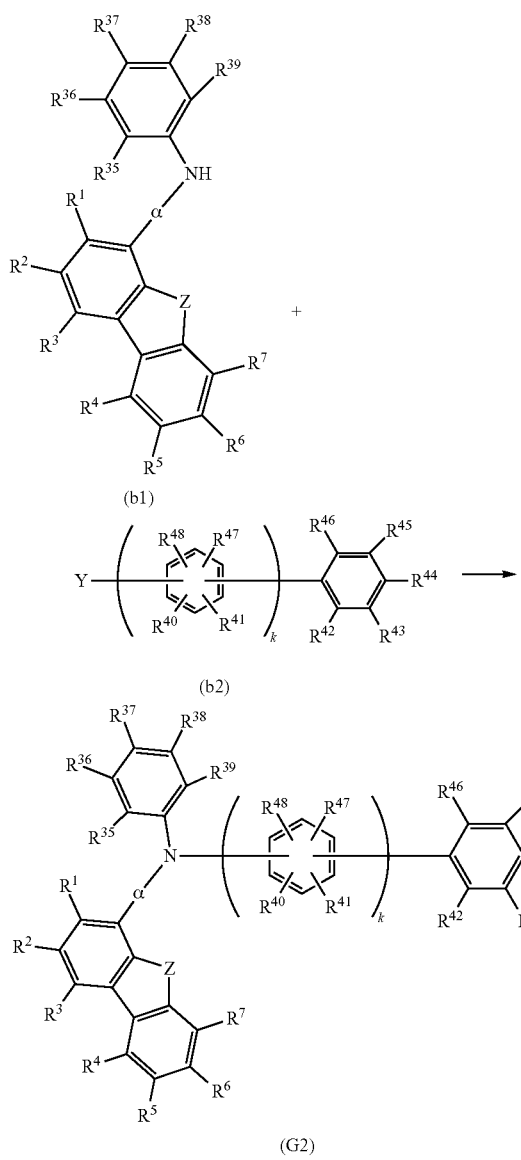

(F-2)

[Chemical Formula 33]

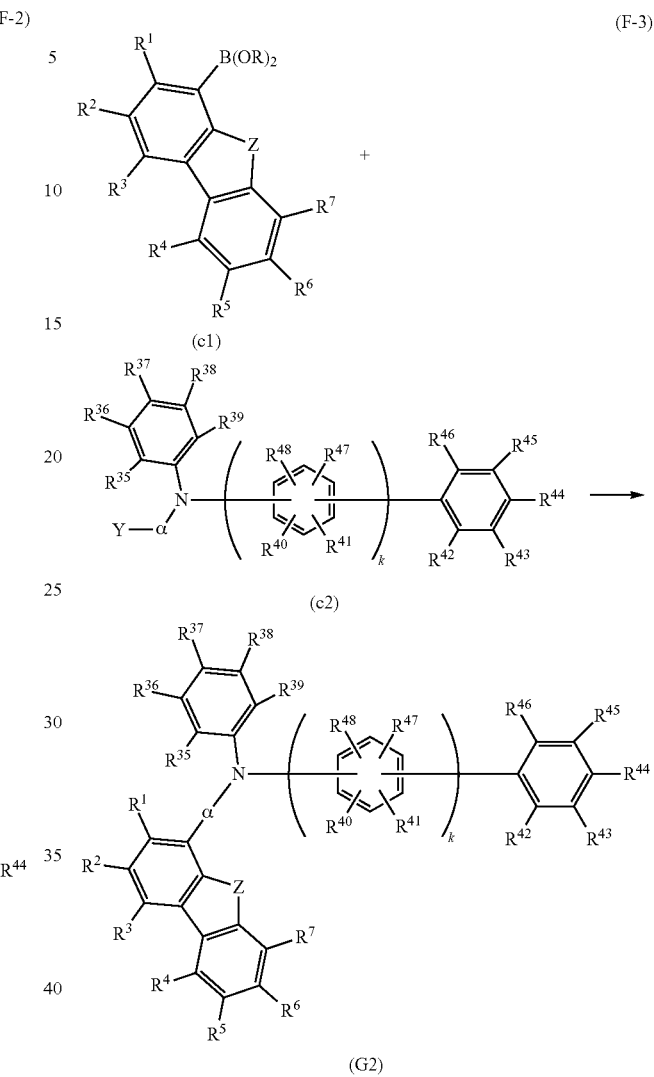

(F-3)

In Synthesis Scheme (F-2), Y represents a halogen atom and is preferably iodine, bromine, and chlorine in this order in terms of high reactivity. Alternatively, Y may be triflate.

In this synthesis scheme, a coupling reaction of an amine compound represented by (b1) and a halide represented by (b2) is caused, whereby the amine compound represented by (G2) can be synthesized.

A variety of reaction conditions can be used in performing the synthesis, and a synthesis method using a metal catalyst in the presence of a base can be used as an example. Specifically, the Buchwald-Hartwig reaction or the Ullmann reaction can be used.

This reaction is preferably performed under an inert atmosphere of nitrogen, argon, or the like. Further, heating may be performed using electromagnetic waves.

In Synthesis Scheme (F-3) shown above, B represents a boron atom, and R represents hydrogen or an alkyl group. Y represents a halogen atom and is preferably iodine, bromine, and chlorine in this order in terms of high reactivity. Alternatively, Y may be triflate.

In this synthesis scheme, a coupling reaction of a boride represented by (c1) and a halide represented by (c2) is caused, whereby the amine compound represented by (G2) can be synthesized.

A variety of reaction conditions can be used in the case of performing the synthesis, and a synthesis method using a metal catalyst in the presence of a base can be used as an example. Specifically, a Suzuki-Miyaura coupling reaction can be employed.

Note that instead of the aryl boron compound (c1), aryl aluminum, aryl zirconium, aryl zinc, aryl tin, or the like may be used for a leaving group $B(OR)_2$.

In addition, the reaction is preferably performed under an inert atmosphere of nitrogen, argon, or the like. Further, heating may be performed using electromagnetic waves.

EMBODIMENT 3

In this embodiment, a light-emitting device using the light-emitting element described in Embodiment 1 is described.

Figure 2A:
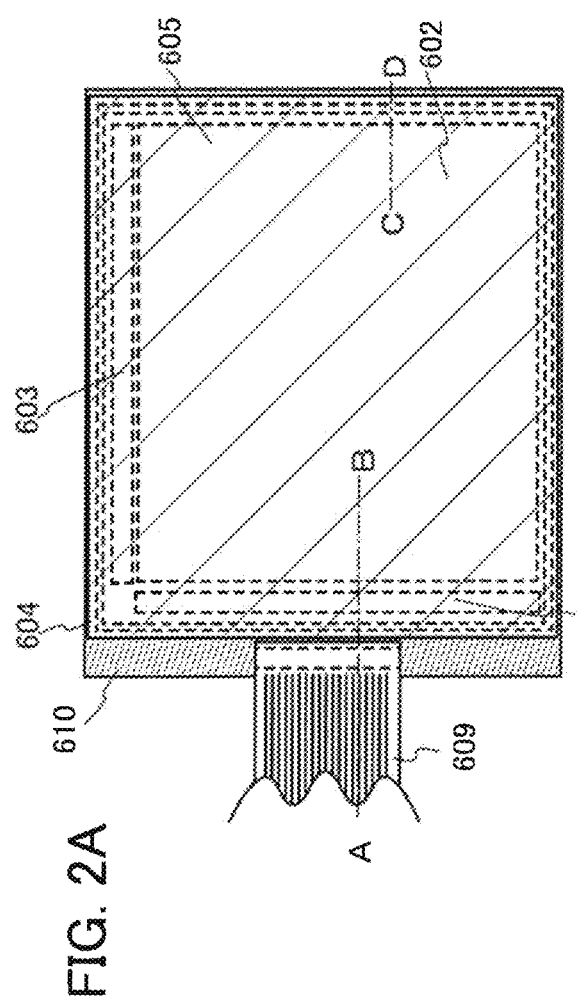
FIGS. 2A and 2B are conceptual diagrams of an active matrix light-emitting device.
Figure 2B:
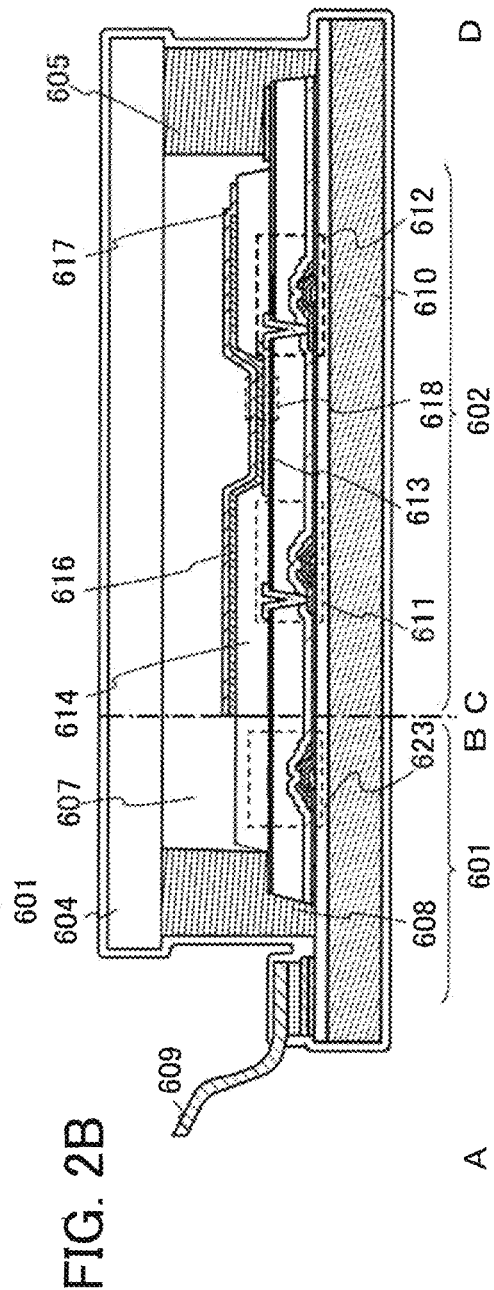

In this embodiment, the light-emitting device manufactured using the light-emitting element described in Embodiment 1 is described using FIG. 2. Note that FIG. 2(A) is a top view illustrating the light-emitting device, and FIG. 2(B) is a cross-sectional view taken along A-B and C-D in FIG. 2(A). This light-emitting device includes a driver circuit portion (source line driver circuit) 601, a pixel portion 602, and a driver circuit portion (gate line driver circuit) 603, which are to control light emission of a light-emitting element and illustrated with dotted lines. In addition, 604 is a sealing substrate, 605 is a sealing material, and the inside surrounded by the sealing material 605 is a space 607.

Note that a lead wiring 608 is a wiring for transmitting signals to be input to the source line driver circuit 601 and the gate line driver circuit 603 and receives signals such as a video signal, a clock signal, a start signal, and a reset signal from an FPC (flexible printed circuit) 609 serving as an external input terminal. Note that although only the FPC is illustrated here, a printed wiring board (PWB) may be attached to the FPC. The light-emitting device in this specification includes not only the main body of the light-emitting device but also the FPC or the PWB attached to the light-emitting device.

Next, a cross-sectional structure is described using FIG. 2(B). The driver circuit portions and the pixel portion are formed over an element substrate 610, and here, the source line driver circuit 601, which is a driver circuit portion, and one pixel in the pixel portion 602 are illustrated.

The element substrate 610 may be formed using a substrate made of glass, quartz, an organic resin, a metal, an alloy, or a semiconductor or a plastic substrate made of FRP (Fiber Reinforced Plastics), PVF (polyvinyl fluoride), polyester, acrylic, or the like.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and either an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, the off-state current of the transistor can be reduced.

The oxide semiconductor preferably contains at least indium (In) or zinc (Zn). Further preferably, the oxide semiconductor is an oxide semiconductor containing an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above semiconductor layer can be held for a long time because of the low off-state current of the transistor. When such a transistor is used in a pixel, a driver circuit can be stopped while a gray scale of an image displayed in each display region is maintained. As a result, an electronic device with noticeably reduced power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a CVD (Chemical Vapor Deposition) method (a plasma CVD method, a thermal CVD method, a MOCVD (Metal Organic CVD) method, or the like), an ALD (Atomic Layer Deposition) method, a coating method, a printing method, or the like. Note that the base film does not need to be provided if unnecessary.

Note that an FET 623 is illustrated as a transistor formed in the driver circuit portion 601. In addition, the driver circuit may be formed with a variety of CMOS circuits, PMOS circuits, or NMOS circuits. Although a driver integrated type in which the driver circuit is formed over the substrate is illustrated in this embodiment, the driver circuit is not necessarily formed over the substrate, and the driver circuit can be formed outside, not over the substrate.

The pixel portion 602 is formed of a plurality of pixels including a switching FET 611, a current controlling FET 612, and a first electrode 613 electrically connected to a drain of the current controlling FET 612; however, without limitation thereto, the pixel portion 602 may include three or more FETs and a capacitor in combination.

Note that an insulator 614 is formed to cover an end portion of the first electrode 613. Here, the insulator 614 can be formed using a positive photosensitive acrylic resin film.

In order to improve coverage with an EL layer or the like which is formed later, the insulator 614 is formed to have a curved surface with curvature at its upper or lower end portion. For example, in the case where positive photosensitive acrylic is used as a material of the insulator 614, only the upper end portion of the insulator 614 preferably has a curved surface with a curvature radius (0.2 µm to 3 µm). In addition, as the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is desirably used. For example, a single-layer film of an ITO film, an indium tin oxide film containing silicon, an indium oxide film containing zinc oxide at 2 to 20 wt %, a titanium nitride film, a chromium film, a tungsten film, a Zn film, a Pt film, or the like, a stack of a titanium nitride film and a film containing aluminum as its main component, a three-layer structure of a titanium nitride film, a film containing aluminum as its main component, and a titanium nitride film, or the like can be used. Note that the stacked-layer structure enables low wiring resistance, favorable ohmic contact, and a function as an anode.

In addition, the EL layer 616 is formed by a variety of methods such as an evaporation method using an evaporation mask, an inkjet method, and a spin coating method. The EL layer 616 has the structure described in Embodiment 1. Another material included in the EL layer 616 may be a low molecular compound or a high molecular compound (including an oligomer or a dendrimer).

Furthermore, as a material used for the second electrode 617, which is formed over the EL layer 616 and functions as a cathode, a material having a low work function (e.g., Al, Mg, Li, and Ca, or an alloy or a compound thereof (MgAg, MgIn, AlLi, and the like)) is preferably used. Note that in the case where light generated in the EL layer 616 is transmitted through the second electrode 617, a stack of a thin metal film with a reduced thickness and a transparent conductive film (e.g., ITO, indium oxide containing zinc oxide at 2 to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element is the light-emitting element described in Embodiment 1. Note that in the light-emitting device of this embodiment, the pixel portion, which includes a plurality of light-emitting elements, may include both the light-emitting element described in Embodiment 1 and a light-emitting element having a different structure.

Furthermore, the sealing substrate 604 is attached to the element substrate 610 with the sealing material 605, so that a light-emitting element 618 is provided in the space 607 surrounded by the element substrate 610, the sealing substrate 604, and the sealing material 605. Note that the space 607 is filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

Note that an epoxy-based resin or glass frit is preferably used for the sealing material 605. Furthermore, it is desirable that such a material not be permeable to moisture or oxygen as much as possible. As a material used as the sealing substrate 604, a glass substrate, a quartz substrate, or a plastic substrate formed of FRP (Fiber Reinforced Plastics), PVF (polyvinyl fluoride), polyester, acrylic, or the like can be used.

Although not illustrated in FIG. 2, a protective film may be provided over the second electrode. The protective film can be formed with an organic resin film or an inorganic insulating film. Furthermore, the protective film may be formed so as to cover an exposed portion of the sealing material 605. The protective film can be provided so as to cover surfaces and side surfaces of the pair of substrates and exposed side surfaces of a sealing layer, an insulating layer, and the like.

For the protective film, a material through which an impurity such as water does not permeate easily can be used. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, or the like, a material containing aluminum nitride, hafnium nitride, silicon nitride, tantalum nitride, titanium nitride, niobium nitride, molybdenum nitride, zirconium nitride, gallium nitride, or the like, or a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like can be used.

The protective film is preferably formed using a deposition method with favorable step coverage (step coverage). One such method is an atomic layer deposition (ALD: Atomic Layer Deposition) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on a surface with a complex uneven shape or upper, side, and rear surfaces of a touch panel, for example.

In the above manner, the light-emitting device manufactured using the light-emitting element described in Embodiment 1 can be obtained.

The light-emitting device in this embodiment uses the light-emitting element described in Embodiment 1 and thus the light-emitting device with favorable characteristics can be obtained. Specifically, since the light-emitting element described in Embodiment 1 has a long lifetime, the light-emitting device can have high reliability. Since the light-emitting device using the light-emitting element described in Embodiment 1 has high emission efficiency, the light-emitting device can have low power consumption.

FIG. 3 illustrates an example of a light-emitting device in which full color display is achieved by formation of a light-emitting element exhibiting white light emission and provision of coloring layers (color filters) and the like. In FIG. 3(A), a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealing material 1032, and the like are illustrated.

In FIG. 3(A), coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3(A), there are the light-emitting layer from which light is emitted to the outside without passing through the coloring layers and the light-emitting layer from which light is emitted through the coloring layers of the colors. Since light which does not pass through the coloring layers is white and light which passes through the coloring layer is red, green, or blue, an image can be displayed using pixels of the four colors.

FIG. 3(B) illustrates an example in which the coloring layers (the red coloring layer 1034R, the green coloring layer 1034G, and the blue coloring layer 1034B) are formed between the gate insulating film 1003 and the first interlayer insulating film 1020. As in this example, the coloring layers may be provided between the substrate 1001 and the sealing substrate 1031.

Figure 4:
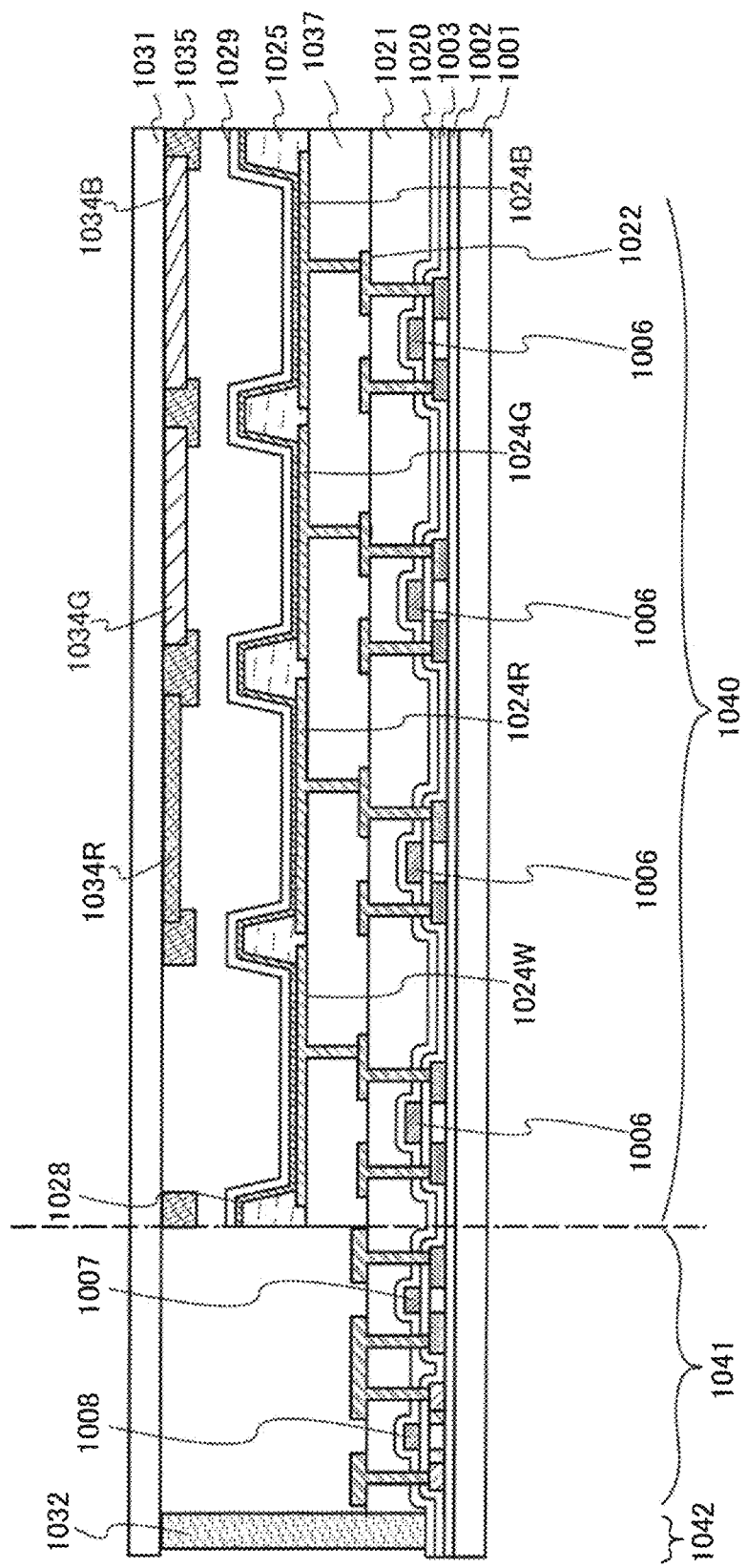
FIG. 4 is a conceptual diagram of an active matrix light-emitting device.

The above-described light-emitting device is a light-emitting device having a structure in which light is extracted from the substrate 1001 side where FETs are formed (bottom emission type), but may be a light-emitting device having a structure in which light is extracted from the sealing substrate 1031 side (top emission type). FIG. 4 shows a cross-sectional view of a top-emission light-emitting device. In this case, a substrate which does not transmit light can be used as the substrate 1001. Up to formation of a connection electrode which connects the FET and the anode of the light-emitting element, the top-emission light-emitting device is formed in a manner similar to that of the bottom-emission light-emitting device. Then, a third interlayer insulating film 1037 is formed to cover an electrode 1022. This insulating film may have a planarization function. The third interlayer insulating film 1037 can be formed using a material similar to that of the second interlayer insulating film or other known materials.

The first electrodes 1024W, 1024R, 1024G, and 1024B of the light-emitting elements are anodes here, but may be cathodes. Furthermore, in the case of a top-emission light-emitting device like that in FIG. 4, the first electrodes are preferably reflective electrodes. The structure of the EL layer 1028 is similar to the structure of the EL layer 103, which is described in Embodiment 1, and the element structure with which white light emission can be obtained is formed.

In the case of a top emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. An example in which full color display is performed using four colors of red, green, blue, and white is shown here; however, without particular limitation thereto, full color display using four colors of red, yellow, green, and blue or three colors of red, green, and blue may be performed.

In the top-emission light-emitting device, a microcavity structure can be suitably employed. A light-emitting element with a microcavity structure is obtained with the use of a reflective electrode as the first electrode and a semi-transmissive and semi-reflective electrode as the second electrode. The light-emitting element with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1 \times 10^{-2}$ Ωcm or lower. In addition, the semi-transmissive and semi-reflective electrode is a film having a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting element, by changing the thicknesses of the transparent conductive film, the above composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (note that n is a natural number of 1 or larger and $\lambda$ is the wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. For example, the structure may be combined with that of the tandem light-emitting element described above, and applied to a structure where one light-emitting element is provided with a plurality of EL layers between which a charge generation layer is provided and a single light-emitting layer or a plurality of light-emitting layers is formed in each EL layer.

With the microcavity structure, emission intensity with a specific wavelength in the front direction can be increased, whereby power consumption can be reduced. Note that in the case of a light-emitting device which displays images with subpixels of four colors, red, yellow, green, and blue, the light-emitting device can have favorable characteristics because the luminance can be increased owing to yellow light emission and each subpixel can employ a microcavity structure suitable for the wavelengths of the corresponding colors.

The light-emitting device in this embodiment uses the light-emitting element described in Embodiment 1 and thus the light-emitting device with favorable characteristics can be obtained. Specifically, since the light-emitting element described in Embodiment 1 has a long lifetime, the light-emitting device can have high reliability. Furthermore, since the light-emitting device using the light-emitting element described in Embodiment 1 has high emission efficiency, the light-emitting device can have low power consumption.

Figure 5A:
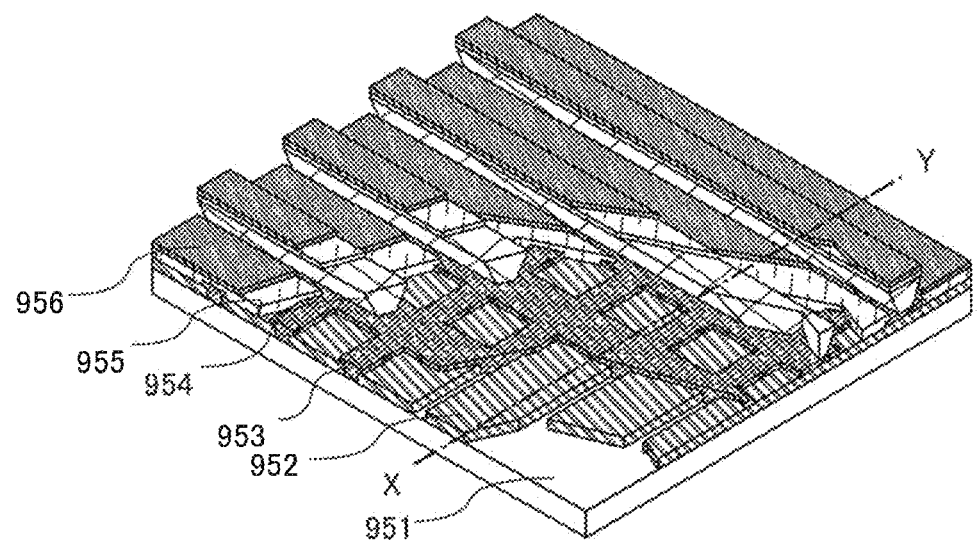
FIGS. 5A and 5B are conceptual diagrams of a passive matrix light-emitting device.
Figure 5B:
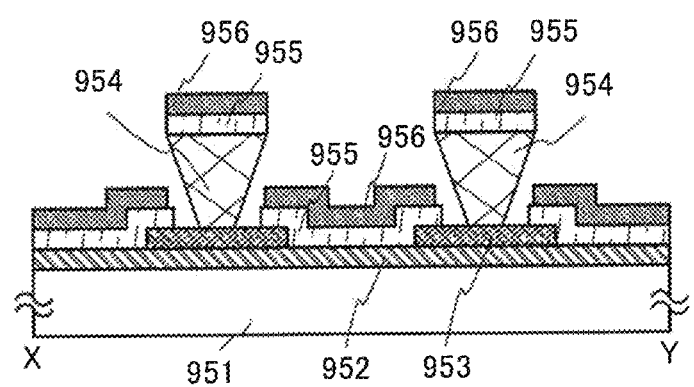

An active matrix light-emitting device is described above, whereas a passive matrix light-emitting device is described below. FIG. 5 illustrates a passive matrix light-emitting device manufactured using the present invention. Note that FIG. 5(A) is a perspective view illustrating the light-emitting device, and FIG. 5(B) is a cross-sectional view taken along X-Y in FIG. 5(A). In FIG. 5, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between one sidewall and the other sidewall is gradually narrowed toward the surface of the substrate. In other words, a cross section taken along the direction of the short side of the partition layer 954 is trapezoidal, and the bottom side (a side which is oriented in the same direction as that of the surface of the insulating layer 953 and is in contact with the insulating layer 953) is shorter than the top side (a side which is oriented in the same direction as that of the surface of the insulating layer 953 and is not in contact with the insulating layer 953). The partition layer 954 thus provided can prevent defects in the light-emitting element due to static electricity or others. The passive-matrix light-emitting device also includes the light-emitting element described in Embodiment 1; thus, the light-emitting device can have high reliability or low power consumption.

Since many minute light-emitting elements arranged in a matrix in the light-emitting device described above can each be controlled, the light-emitting device can be suitably used as a display device for expressing images.

This embodiment can be freely combined with the other embodiments.

EMBODIMENT 4

Figure 6A:
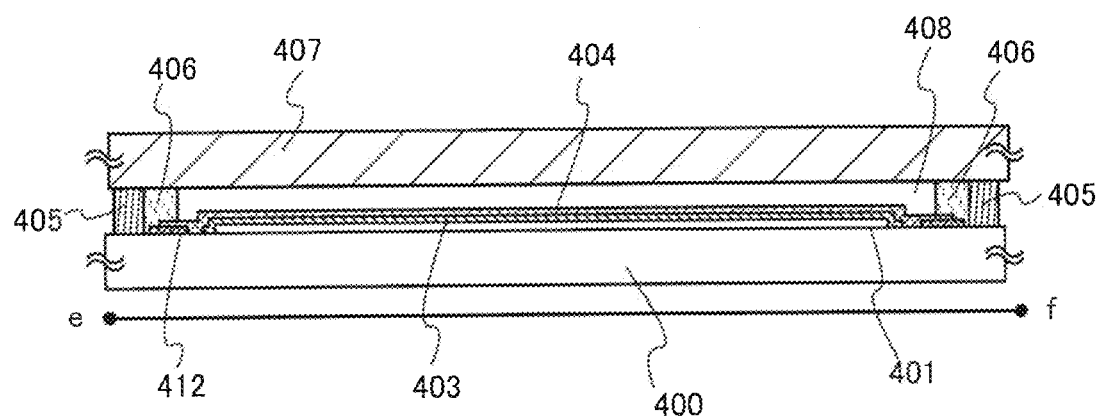
FIGS. 6A and 6B are diagrams illustrating a lighting device.
Figure 6B:
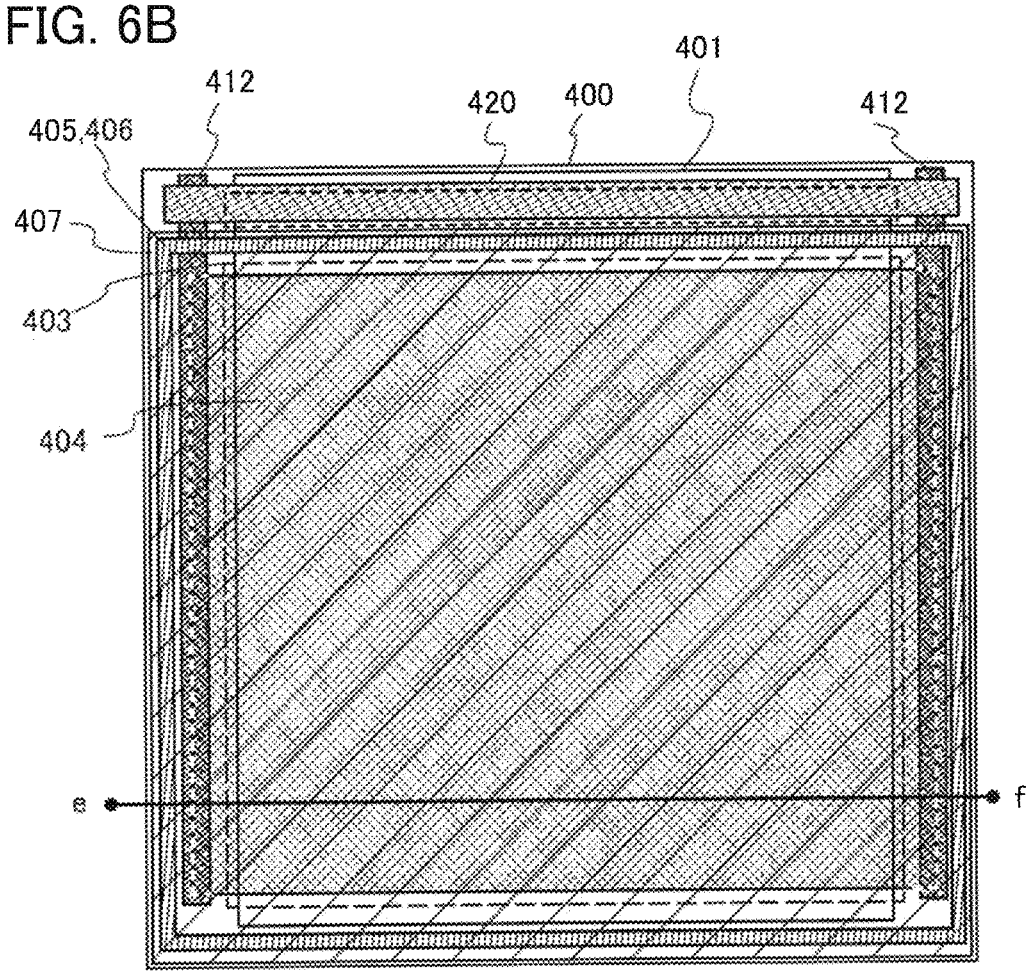

In this embodiment, an example in which the light-emitting element described in Embodiment 1 is used for a lighting device is described with reference to FIG. 6. FIG. 6(B) is a top view of the lighting device, and FIG. 6(A) is a cross-sectional view along e-f in FIG. 6(B).

In the lighting device in this embodiment, a first electrode 401 is formed over a substrate 400 which is a support and has a light-transmitting property. The first electrode 401 corresponds to the first electrode 101 in Embodiment 1. When light emission is extracted from the first electrode 401 side, the first electrode 401 is formed using a material having a light-transmitting property.

A pad 412 for applying voltage to a second electrode 404 is formed over the substrate 400.

An EL layer 403 is formed over the first electrode 401. The EL layer 403 corresponds to, for example, the structure of the EL layer 103 in Embodiment 1, or the structure in which the light-emitting units 511 and 512 and the charge generation layer 513 are combined. Refer to the descriptions for the structures.

The second electrode 404 is formed to cover the EL layer 403. The second electrode 404 corresponds to the second electrode 102 in Embodiment 1. The second electrode 404 is formed using a material having high reflectance when light emission is extracted from the first electrode 401 side. The second electrode 404 is connected to the pad 412, whereby voltage is applied.

As described above, the lighting device described in this embodiment includes a light-emitting element including the first electrode 401, the EL layer 403, and the second electrode 404. Since the light-emitting element is a light-emitting element with high emission efficiency, the lighting device in this embodiment can be a lighting device having low power consumption.

The substrate 400 provided with the light-emitting element having the above structure is fixed to a sealing substrate 407 with sealing materials 405 and 406 and sealing is performed, whereby the lighting device is completed. It is possible to use only either the sealing material 405 or 406. Furthermore, the inner sealing material 406 (not shown in FIG. 6(B)) can be mixed with a desiccant which enables moisture to be adsorbed, increasing reliability.

When parts of the pad 412 and the first electrode 401 are extended to the outside of the sealing materials 405 and 406, they can serve as external input terminals. An IC chip 420 mounted with a converter or the like may be provided over the external input terminals.

The lighting device described in this embodiment uses, as an EL element, the light-emitting element described in Embodiment 1; thus, the light-emitting device can have high reliability. In addition, the light-emitting device have low power consumption.

EMBODIMENT 5

In this embodiment, examples of electronic devices including the light-emitting element described in Embodiment 1 are described. The light-emitting element described in Embodiment 1 has a favorable lifetime and high reliability. As a result, the electronic devices described in this embodiment can include a light-emitting portion having high reliability.

Examples of the electronic devices to which the above light-emitting element is applied include television devices (also referred to as TV or television receivers), monitors for computers and the like, digital cameras, digital video cameras, digital photo frames, mobile phones (also referred to as cell phones or mobile phone devices), portable game machines, portable information terminals, audio playback devices, large game machines such as pachinko machines, and the like. Specific examples of these electronic devices are given below.

FIG. 7(A) illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements described in Embodiment 1 are arranged in a matrix.

Operation of the television device can be performed with an operation switch of the housing 7101 or a separate remote controller 7110. With operation keys 7109 of the remote controller 7110, channels and volume can be controlled and images displayed on the display portion 7103 can be controlled. In addition, the remote controller 7110 may be provided with a display portion 7107 for displaying information output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (e.g., between a sender and a receiver or between receivers) information communication can be performed.

FIG. 7(B1) illustrates a computer, which includes a main body 7201, a housing 7202, a display portion 7203, a keyboard 7204, an external connection port 7205, a pointing device 7206, and the like. Note that this computer is manufactured using the light-emitting elements described in Embodiment 1 which are arranged in a matrix in the display portion 7203. The computer in FIG. 7(B1) may have a form illustrated in FIG. 7(B2). The computer in FIG. 7(B2) is provided with a second display portion 7210 instead of the keyboard 7204 and the pointing device 7206. The second display portion 7210 is a touch screen-type, and input can be performed by operation of display for input, which is displayed on the second display portion 7210, with a finger or a dedicated pen. The second display portion 7210 can also display other images as well as display for input. The display portion 7203 may also be a touch screen. Connecting the two screens with a hinge can prevent troubles; for example, the screens can be prevented from being cracked or broken while the computer is being stored or carried.

FIG. 7(C) illustrates a portable game machine having two housings, a housing 7301 and a housing 7302, which are connected with a joint portion 7303 so that the portable game machine can be opened and closed. The housing 7301 incorporates a display portion 7304 in which the light-emitting elements described in Embodiment 1 are arranged in a matrix, and the housing 7302 incorporates a display portion 7305. In addition, the portable game machine illustrated in FIG. 7(C) further includes a speaker portion 7306, a recording medium insertion portion 7307, an LED lamp 7308, input means (an operation key 7309, a connection terminal 7310, a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion in which the light-emitting elements described in Embodiment 1 are arranged in a matrix is used as either the display portion 7304 or the display portion 7305, or both, and the structure can include other accessories as appropriate. The portable game machine illustrated in FIG. 7(C) has a function of reading out a program or data stored in a recoding medium to display it on the display portion, and a function of sharing information with another portable game machine by wireless communication. Note that functions of the portable game machine illustrated in FIG. 7(C) are not limited to them, and the portable game machine can have various functions.

FIG. 7(D) illustrates an example of a portable terminal. The mobile phone is provided with a display portion 7402 incorporated in a housing 7401, operation buttons 7403, an external connection port 7404, a speaker 7405, a microphone 7406, and the like. Note that the mobile phone 7400 has the display portion 7402 in which the light-emitting elements described in Embodiment 1 are arranged in a matrix.

When the display portion 7402 of the portable terminal illustrated in FIG. 7(D) is touched with a finger or the like, information can be input into the portable terminal. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode mainly for inputting characters is selected for the display portion 7402 so that characters displayed on a screen can be input. In this case, it is preferable to display a keyboard or number buttons on almost the entire screen of the display portion 7402.

In addition, when a detecting device including a sensor for detecting inclination such as a gyroscope or an acceleration sensor is provided inside the portable terminal, display on the screen of the display portion 7402 can be automatically changed in direction by determining the orientation of the portable terminal (horizontal orientation or vertical orientation).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is moving image data, the screen mode is switched to the display mode. When the signal is a signal of text data, the screen mode is switched to the input mode.

Moreover, in the input mode, if a signal detected by an optical sensor in the display portion 7402 is detected and the input by touch operation of the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Furthermore, by using a backlight which emits near-infrared light or a sensing light source which emits near-infrared light in the display portion, an image of a finger vein, or a palm vein can be taken.

Note that the structure described in this embodiment can be combined with any of the structures described in Embodiments 1 to 5 as appropriate.

As described above, the application range of the light-emitting device including the light-emitting element described in Embodiment 1 is wide, so that this light-emitting device can be applied to electronic devices in a variety of fields. By using the light-emitting element described in Embodiment 1, an electronic device having high reliability can be obtained.

Figure 8:
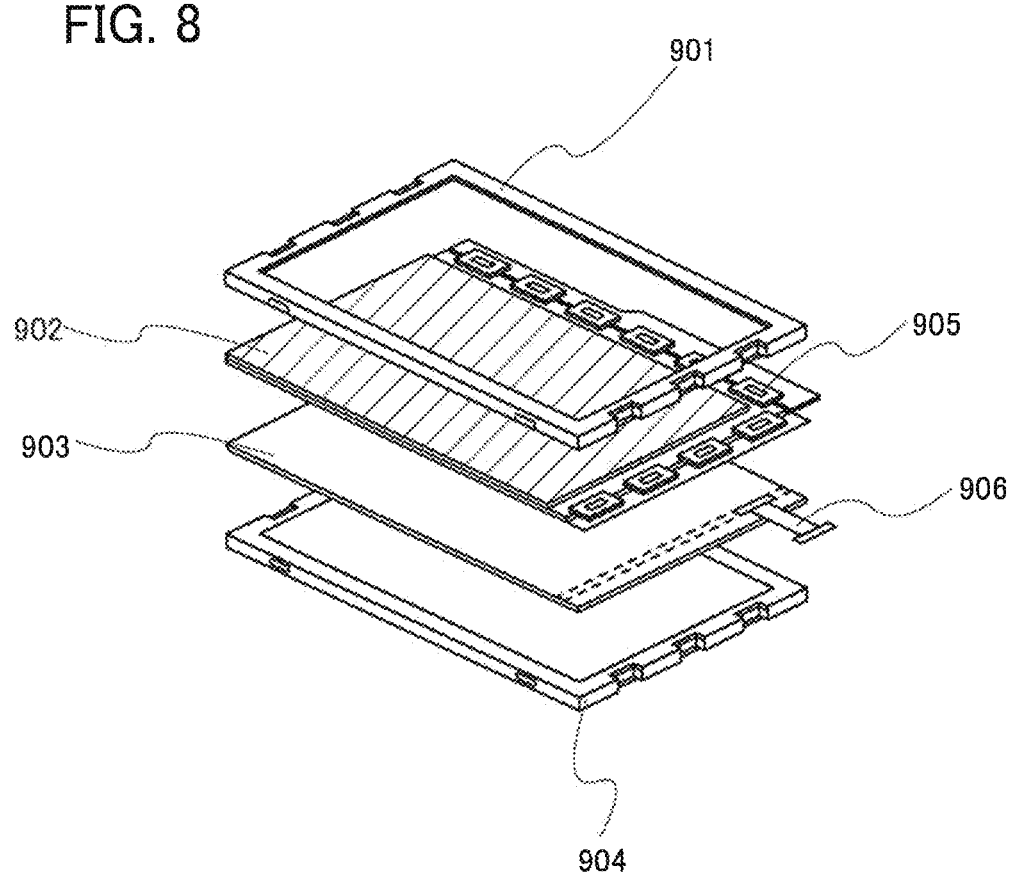
FIG. 8 is a diagram illustrating a light source device.

FIG. 8 illustrates an example of a liquid crystal display device using the light-emitting element described in Embodiment 1 for a backlight. The liquid crystal display device illustrated in FIG. 8 includes a housing 901, a liquid crystal layer 902, a backlight unit 903, and a housing 904. The liquid crystal layer 902 is connected to a driver IC 905. The light-emitting element described in Embodiment 1 is used for the backlight unit 903, to which current is supplied through a terminal 906.

The light-emitting element described in Embodiment 1 is used for the backlight of the liquid crystal display device; thus, the backlight with reduced power consumption can be obtained. In addition, the use of the light-emitting element described in Embodiment 1 enables manufacture of a planar-emission lighting device and further an increase in area. Therefore, the backlight can be a larger-area backlight, and the liquid crystal display device can also be a larger-area device. Furthermore, the light-emitting device using the light-emitting element described in Embodiment 1 can be thinner than a conventional one; accordingly, the display device can also be thinner.

Figure 9:
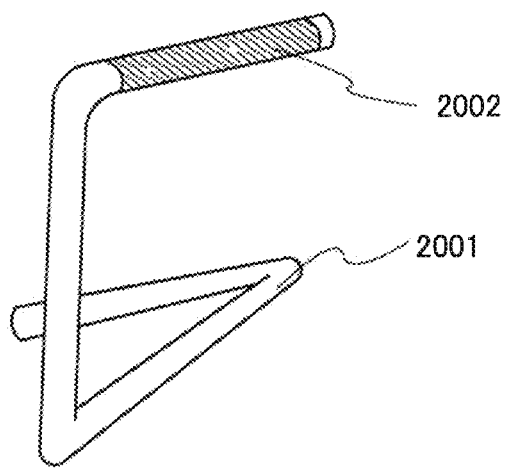
FIG. 9 is a diagram illustrating a lighting device.

FIG. 9 illustrates an example in which the light-emitting element described in Embodiment 1 is used for a table lamp which is a lighting device. The table lamp illustrated in FIG. 9 includes a housing 2001 and a light source 2002, and the lighting device described in Embodiment 4 may be used for the light source 2002.

Figure 10:
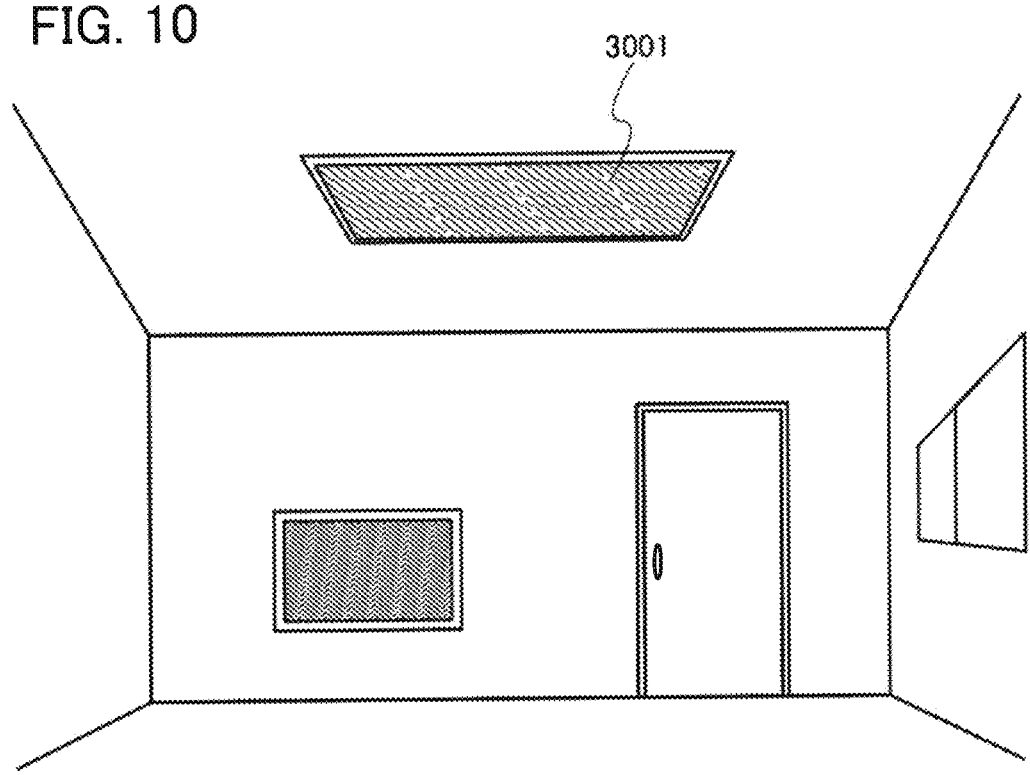
FIG. 10 is a diagram illustrating a lighting device.

FIG. 10 is an example in which the light-emitting element described in Embodiment 1 is used for an indoor lighting device 3001. Since the light-emitting element described in Embodiment 1 has high reliability, the lighting device can have high reliability. Furthermore, since the light-emitting element described in Embodiment 1 can have a large area, the light-emitting element can be used for a large-area lighting device. Furthermore, since the light-emitting element described in Embodiment 1 is thin, the light-emitting element can be used as a lighting device having a reduced thickness.

Figure 30:
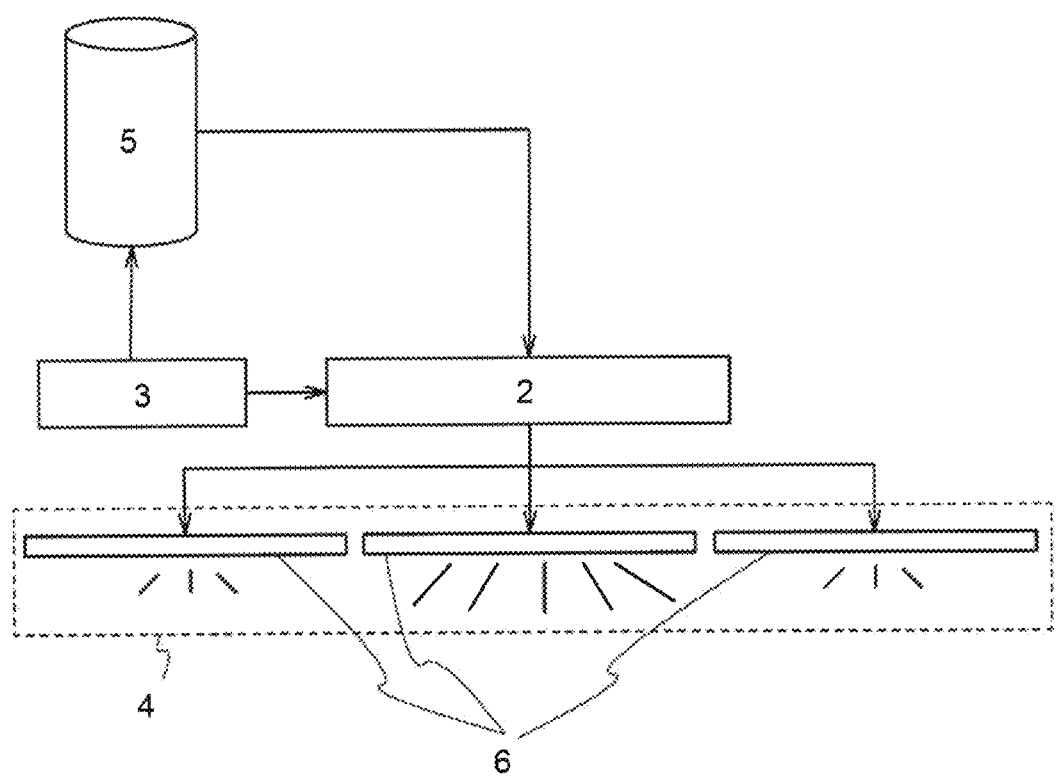
FIG. 30 is a block diagram of a lighting system.

A lighting system 1 of the present invention is specifically described using a drawing. FIG. 30 is a function block diagram of the lighting system 1 of the present invention.

The lighting system 1 is composed of at least a control portion 2, a sensor portion 3, and a lighting portion 4. The lighting portion 4 includes a plurality of light-emitting device portions 6. A database 5 may also be included. The database 5 may be a database via the Internet, such as cloud.

The control portion 2 sets the emission intensity of each of the light-emitting devices 6 on the basis of the detection result in the sensor portion 3, information in the database 5, and the like.

Here, the light-emitting devices 6 are divided into a plurality of groups. Thus, the control portion 2 sets the respective emission intensities for the groups to drive light-emitting elements included in the light-emitting device portions 6. The light-emitting elements are current driving elements; thus, the emission intensities can be set by controlling flowing current.

The sensor portion 3 detects the presence and position of a user and gives information to the control portion 2, whereby the light-emitting device portion 6 is driven at appropriate luminance. That is, when the sensor portion 3 detects the presence and position of a user, the lighting system 1 starts light emission or changes its emission intensity. The emission intensities of the plurality of light-emitting elements included in the light-emitting device portion 6 are changed as a user moves, power consumption can be reduced while appropriate brightness is maintained in a necessary portion. The detection of a user can be performed by a known method such as an infrared sensor.

The sensor portion 3 may detect ambient brightness to control the brightness of lighting in an area illuminated by the lighting system 1. When a user is not present, lighting is performed at minimum luminance, whereby the amount of power consumption can be minimized without making a user feel anxious or uncomfortable about darkness when entering the area. As for setting of the brightness, emission intensity corresponding to detected brightness may be set in advance for the control portion 2, or emission intensity corresponding to detected brightness may be determined with reference to the database 5. As a sensor for sensing the brightness, a known optical sensor can be used.

The detection portion 3 may detect a signal from an IC tag. With the IC tag, the attribute of a user is detected or determined, and the emission intensity of the light-emitting element can be changed as appropriate. The light-emitting device in the direction to which a user should travel emits bright light and the light-emitting device in the direction to which the user should not travel emits dim light, whereby the user can be guided. Guidance for a user can be performed with the use of a sensor that detects the position of the user and detection or determination by an IC tag or the like of the attribute of the user. The attribute of the user or determination is performed with the IC tag and the database 5 is referred to, whereby appropriate emission intensity can be set and guidance can be performed. The ease of perceiving the brightness of lighting for guidance varies depending on the ambient brightness or a user; thus, the IC tag is preferably used together with the above sensor that senses brightness.

Note that when the light-emitting elements included in the light-emitting device portion 6 are a set of light-emitting elements that exhibit a plurality of different colors, a plurality of people can be guided at the same time using not only brightness but also the emission colors. That is, the appropriate directions are shown with the emission colors after users are told to travel in the directions of colors announced in advance, for example, one is told to travel in the red direction and another is told to travel in the blue direction, whereby the plurality of users can be guided at the same time. Although the emission colors may be area colors, when three colors of RGB are arranged in a matrix with some degree of precise definition, guidance can be performed with white light emission that is natural for lighting in the case where there is no need to guide a plurality of people, or with a plurality of perceptible emission colors in the case where many people need to be guided.

The use of such a lighting system enables reliable guidance of the order for each person in an examination or a medical checkup in a hospital, for example. Furthermore, characters are not used; accordingly, it is possible to surely guide even a user with poor eyesight and a user who cannot read the characters of the country.

Figure 11:
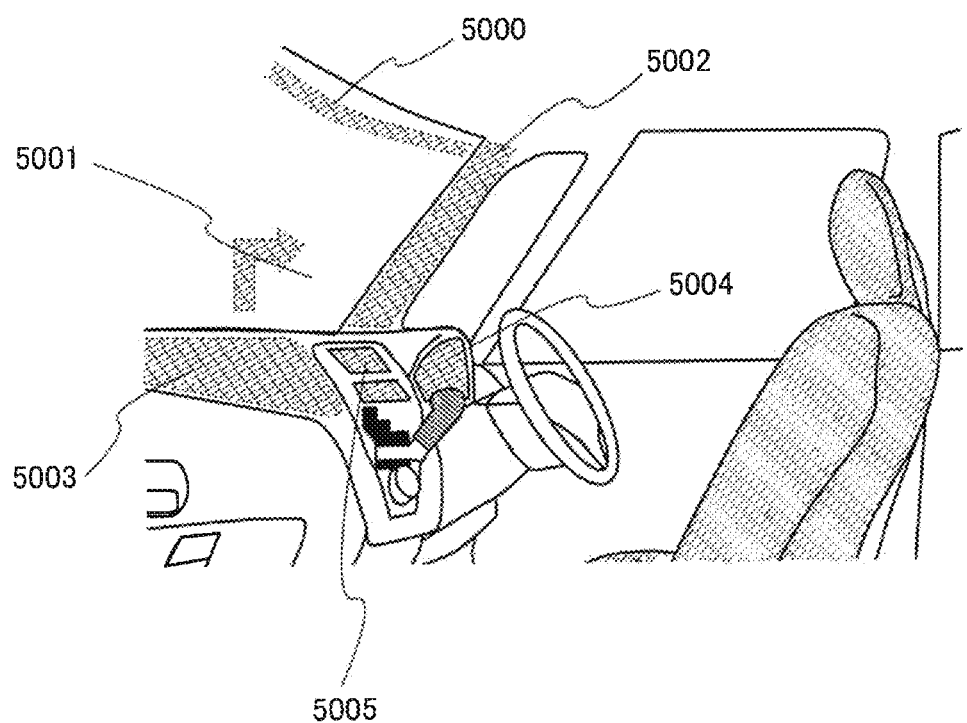
FIG. 11 is a diagram illustrating an in-vehicle display device and a lighting device.

The light-emitting element described in Embodiment 1 can also be mounted on an automobile windshield and an automobile dashboard. FIG. 11 illustrates one mode in which the light-emitting element described in Embodiment 1 is used for an automobile windshield and an automobile dashboard. Display regions 5000 to 5005 are displays provided using the light-emitting element described in Embodiment 1.

The display region 5000 and the display region 5001 are display devices provided in the automobile windshield in which the light-emitting elements described in Embodiment 1 are incorporated. The light-emitting elements described in Embodiment 1 can be formed into what is called a see-through display device, through which the opposite side can be seen, by including a first electrode and a second electrode formed of electrodes having a light-transmitting property. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device that is provided in a pillar portion and in which the light-emitting elements described in Embodiment 1 are incorporated. The display region 5002 can compensate for the view hindered by the pillar by showing an image taken by an imaging means provided in the car body. Similarly, the display region 5003 provided in the dashboard portion can compensate for the view hindered by the car body by showing an image taken by an imaging means provided in the outside of the car, which leads to compensation for blind areas and enhancement of safety. Showing an image so as to compensate for the area which a driver cannot see enables an easy and comfortable safety check.

The display region 5004 and the display region 5005 can provide a variety of kinds of information such as navigation information, a speedometer, a tachometer, a mileage, fuel, a gearshift state, and air-condition setting. The content or layout of the display can be changed according to the user's taste as appropriate. Note that such information can also be provided in the display regions 5000 to 5003. The display regions 5000 to 5005 can also be used as lighting devices.

Figure 12A:
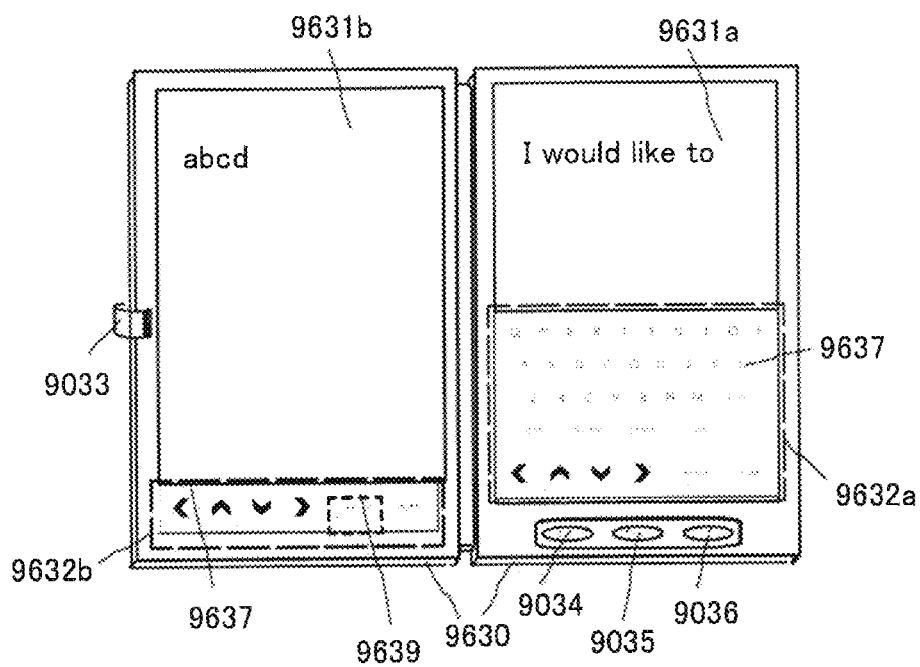
FIGS. 12A-12C are diagrams illustrating an electronic device.
Figure 12B:
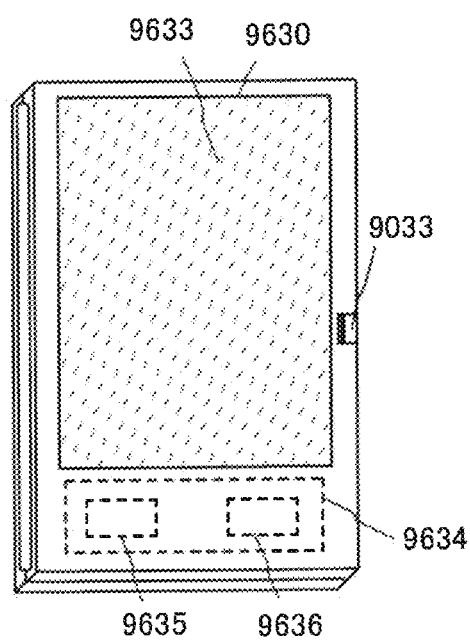

FIGS. 12(A) and 12(B) illustrate an example of a foldable tablet terminal. FIG. 12(A) illustrates the tablet terminal which is unfolded. The tablet terminal includes a housing 9630, a display portion 9631a, a display portion 9631b, a display mode changing switch 9034, a power switch 9035, a power-saving mode changing switch 9036, a clasp 9033, and an operation switch 9038. Note that the tablet terminal is formed using a light-emitting device which includes the light-emitting element described in Embodiment 1 for one or both of the display portion 9631a and the display portion 9631b.

Part of the display portion 9631a can be a touchscreen region 9632a and data can be input when a displayed operation key 9637 is touched. Note that although a half region of the display portion 9631a has only a display function and the other half region has a touchscreen function, the display portion 9631a is not limited to the structure. The whole region of the display portion 9631a may have a touchscreen function. For example, a keyboard can be displayed on the entire surface of the display portion 9631a so that the display portion 9631a is used as a touchscreen, and the display portion 9631b can be used as a display screen.

Like the display portion 9631a, part of the display portion 9631b can also be a touchscreen region 9632b. When a position where a keyboard display switching button 9639 is displayed on the touchscreen is touched with a finger, a stylus, or the like, the keyboard can be displayed on the display portion 9631b.

In addition, touch input can be performed in the touchscreen region 9632a and the touchscreen region 9632b at the same time.

In addition, the display mode changing switch 9034 can switch the display orientation of vertical display, horizontal display, and the like, and select switching between monochrome display and color display, for example. The power-saving mode changing switch 9036 can optimize display luminance in accordance with the amount of external light in use of the tablet terminal that is sensed by an optical sensor incorporated in the tablet terminal. Another detecting device such as a sensor for detecting inclination, e.g., a gyroscope and an acceleration sensor, may be incorporated in the tablet terminal, in addition to the optical sensor.

FIG. 12(A) illustrates an example in which the display portion 9631b and the display portion 9631a have the same display area; however, without particular limitation, the display portion 9631a and the display portion 9631b may have different sizes and different display qualities. For example, one display panel may perform higher definition display than the other.

FIG. 12(B) is a folded state and illustrates an example in which the tablet terminal in this embodiment includes the housing 9630, a solar cell 9633, a charge and discharge control circuit 9634, a battery 9635, and a DCDC converter 9636. Note that in FIG. 12(B), a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-term use.

In addition, the tablet terminal illustrated in FIGS. 12(A) and 12(B) can have other functions such as a function of displaying various kinds of information (e.g., a still image, a moving image, and a text image), a function of displaying a calendar, a date, the time, or the like on the display portion, a touch-input function of operating or editing the information displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that the solar cell 9633 is suitably provided on one or both surfaces of the housing 9630 because the battery 9635 can be charged efficiently.

Figure 12C:
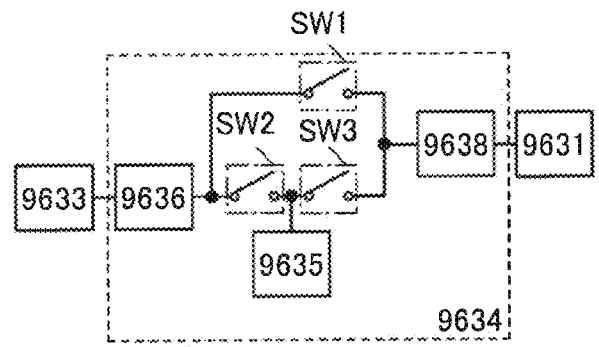

The structure and operation of the charge and discharge control circuit 9634 illustrated in FIG. 12(B) are described showing a block diagram in FIG. 12(C). FIG. 12(C) illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 are portions corresponding to the charge and discharge control circuit 9634 illustrated in FIG. 12(B).

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power obtained by charging in the solar cell 9633 is used for the operation of the display portion 9631, the switch SW1 is turned on and the voltage is raised or lowered by the converter 9638 so as to be voltage needed for the display portion 9631. Meanwhile, when display on the display portion 9631 is not performed, SW1 is turned off and SW2 is turned on so that the battery 9635 is charged.

Note that although the solar cell 9633 is described as an example of a power generation means, the power generation means is not particularly limited, and the battery 9635 may be charged by another power generation means such as a piezoelectric element (piezo element) or a thermoelectric conversion element (Peltier element). Charging may be performed using a non-contact power transmission module that performs charging by transmitting and receiving power wirelessly (without contact) or the other charge means in combination, and the power generation means is not necessarily provided.

The tablet terminal is not limited to that having the shape illustrated in FIG. 12 as long as the display portion 9631 is included.

Figure 13A:
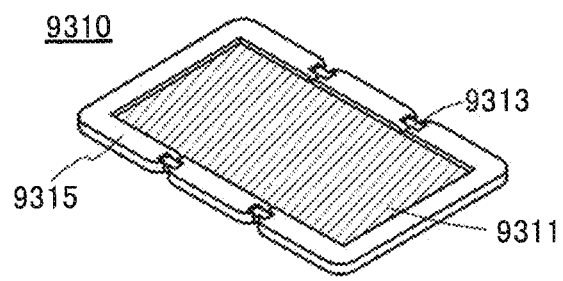
FIGS. 13A-13C are diagrams illustrating an electronic device.
Figure 13B:
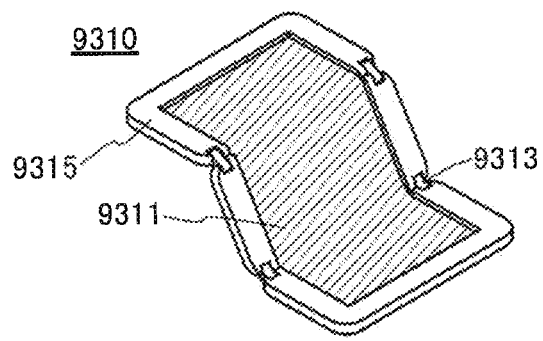
Figure 13C:
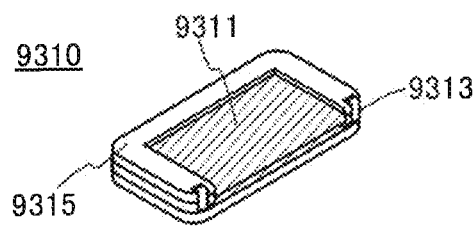

In addition, FIGS. 13(A) to 13(C) illustrate a foldable portable information terminal 9310. FIG. 13(A) illustrates the portable information terminal 9310 that is opened. FIG. 13(B) illustrates the portable information terminal 9310 that is being opened or being folded. FIG. 13(C) illustrates the portable information terminal 9310 that is folded. The portable information terminal 9310 is highly portable when folded. When the portable information terminal 9310 is opened, a seamless large display region allows highly browsable display.

A display panel 9311 is supported by three housings 9315 joined together by hinges 9313. Note that the display panel 9311 may be a touch panel (input/output device) including a touch sensor (input device). In addition, by bending the display panel 9311 between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 is a display region that is positioned at a side surface of the portable information terminal 9310 that is folded. On the display region 9312, information icons, frequently-used applications, shortcuts to programs, and the like can be displayed, and information can be checked and application can be started smoothly.

Note that the triarylamine compound of one embodiment of the present invention, which has a structure in which a dibenzofuran skeleton or a dibenzothiophene skeleton is bonded to nitrogen of an amine directly or through a divalent aromatic hydrocarbon group, can be used for an organic thin-film solar cell. More specifically, the triarylamine compound can be used in a carrier-transport layer or a carrier-injection layer because it has a carrier-transport property. In addition, a mixed film with an acceptor substance can be used as a charge generation layer. The triarylamine compound is photoexcited and hence can be used as a power generation layer.

Example 1

Synthesis Example 1

In this synthesis example, a method for synthesizing N-[3-(dibenzothiophen-4-yl)phenyl]-N-phenyl-4-biphenylamine (abbreviation: mThBA1BP-II) represented by Structural Formula (101) shown below is described.

[Chemical Formula 34]

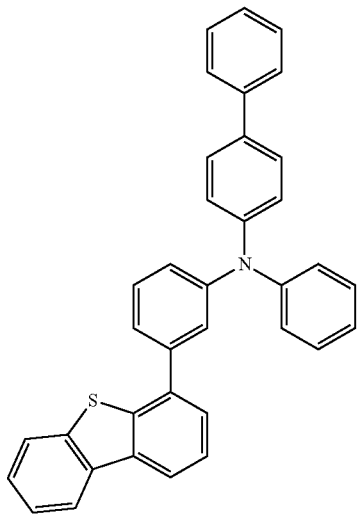

(101)

Into a 50-mL three-neck flask were put 1.7 g (5 mmol) of 4-(3-bromophenyl)-dibenzothiophene, 1.2 g (5 mmol) of N-phenyl-4-biphenylamine, 0.7 g (7 mmol) of sodium tert-butoxide, and 30 mg (50 μmol) of bis(dibenzylideneacetone)palladium(0), the atmosphere in the flask was replaced with nitrogen, and then, 20 mL of dehydrated xylene was added thereto. This mixture was degassed while being stirred under reduced pressure, and then, 0.3 mL (150 μmol) of tri(tert-butyl)phosphine (10 wt % hexane solution) was added thereto. This mixture was heated and stirred under a nitrogen atmosphere at 130° C. for 6.5 hours to be reacted.

After the reaction, 250 mL of toluene was added to this reaction mixture solution, and filtration was performed through Florisil and Celite. The obtained filtrate was concentrated, and purified by silica gel column chromatography (developing solvent, toluene:hexane=1:4). The obtained fraction was concentrated, acetone and methanol were added thereto, irradiation with ultrasonic waves was performed, and then, recrystallization was performed, so that 1.6 g of white powder was obtained with a yield of 64%. The above reaction scheme is shown below.

[Chemical Formula 35]

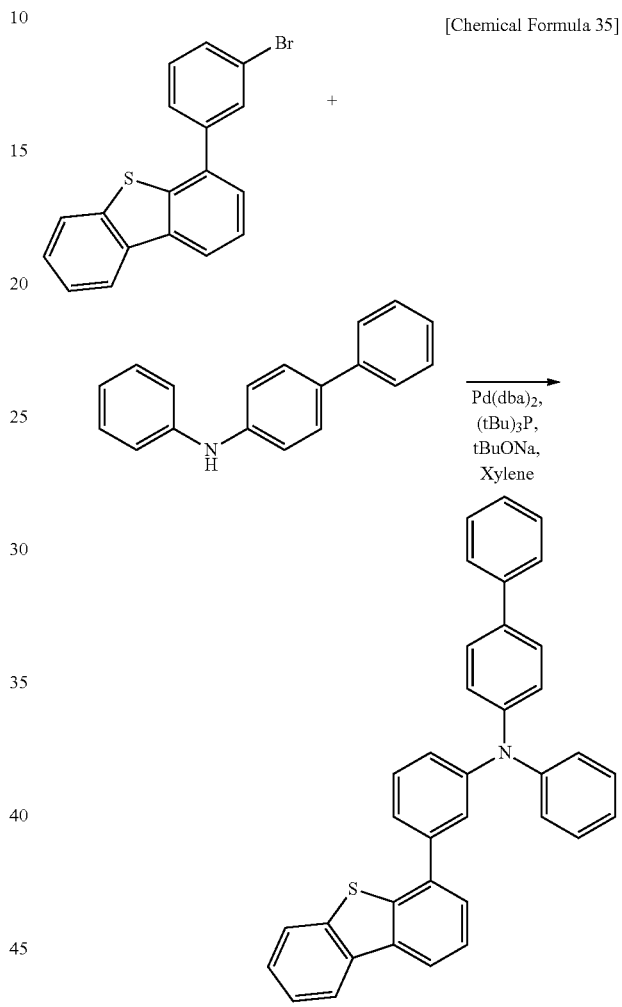

The Rf value by a silica gel thin layer chromatography (TLC) (developing solvent, ethyl acetate:hexane=1:10) was 0.48 for the objective, 0.50 for 4-(3-bromophenyl)-dibenzothiophene, and 0.30 for N-phenyl-4-biphenylamine.

The obtained compound was measured by a nuclear magnetic resonance method (NMR). The measurement data are shown below.

$^1$H NMR (CDCl$_3$, 300 MHz): δ (ppm)=7.09 (1H, t, J=7.5 Hz), 7.23-7.66 (21H, m), 7.83-7.86 (1H, m), 8.13 (1H, dd, J=1.5 Hz, 7.8 Hz), 8.17-8.20 (1H, m).

Figure 14A:
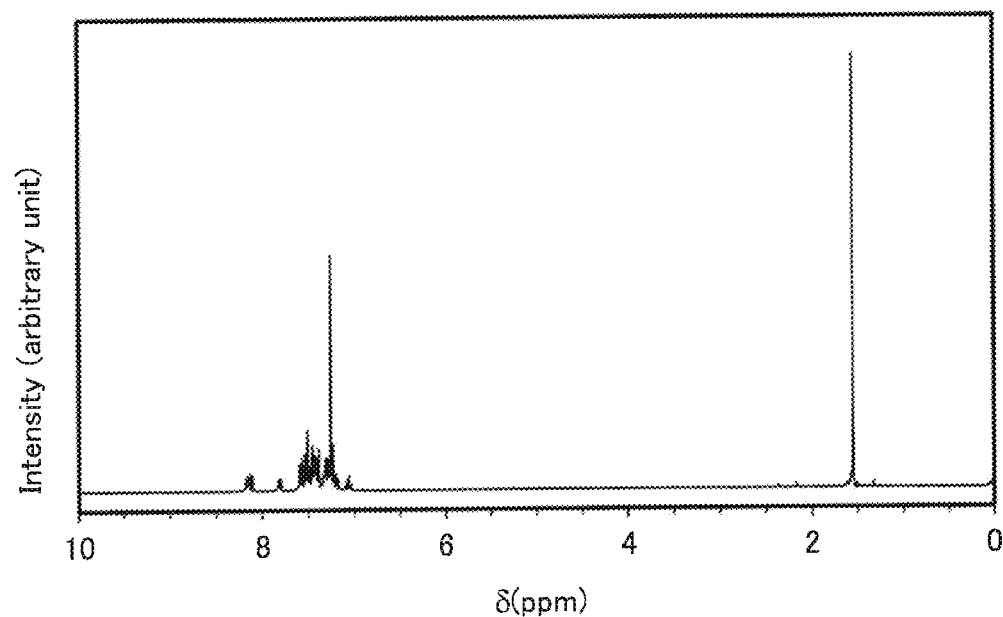
FIGS. 14A and 14B are 1H NMR charts of mThBA1BP-II.
Figure 14B:
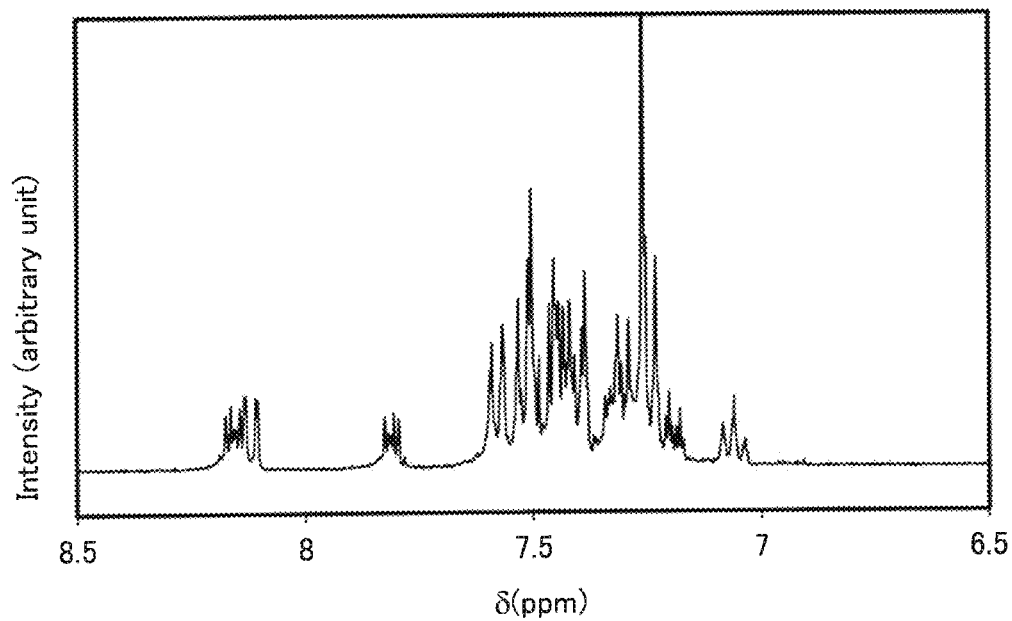

FIGS. 14(A) and (B) show $^1$H NMR charts. Note that FIG. 14(B) is an enlarged chart of FIG. 14(A). The measurement results show that the objective, mThBA1BP-II, was obtained.

In addition, the molecular weight of the obtained compound was measured with a GC/MS detector (ITQ1100 ion trap GCMS system, manufactured by Thermo Fisher).

Accordingly, a main peak with a mass number of 503 (mode is EI+) was detected, and it was confirmed that the objective was obtained.

Example 2

Synthesis Example 2

In this synthesis example, a method for synthesizing N-[4-(dibenzothiophen-4-yl)phenyl]-N-phenyl-4-biphenylamine (abbreviation: ThBA1BP-II) represented by Structural Formula (100) shown below is described.

[Chemical Formula 36]

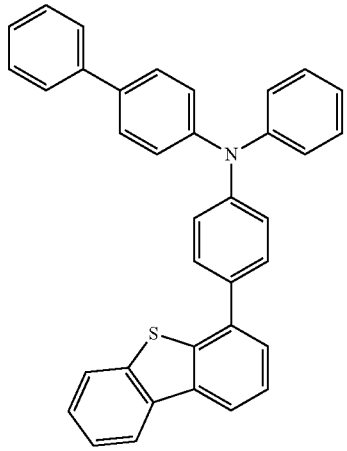

(100)

With 4-(4-bromophenyl)-dibenzothiophene substituted for 4-(3-bromophenyl)-dibenzothiophene used in Synthesis Example 1 of Example 1, synthesis was performed as in Synthesis Example 1, whereby 1.4 g of white powder which was the objective was obtained with a yield of 56%. A reaction scheme is shown below.

[Chemical Formula 37]

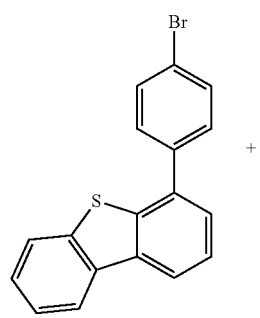

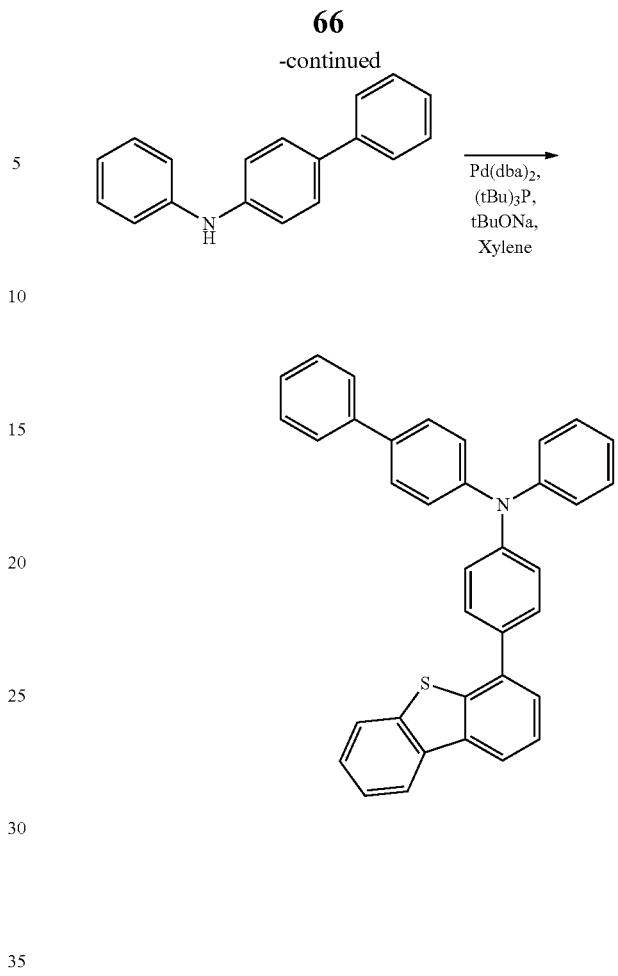

The Rf value by a silica gel thin layer chromatography (TLC) (developing solvent, ethyl acetate:hexane=1:10) was 0.37 for the objective, 0.51 for 4-(4-bromophenyl)-dibenzothiophene, and 0.26 for N-phenyl-4-biphenylamine.

The obtained compound was measured by a nuclear magnetic resonance method (NMR). The measurement data are shown below.

$^1$H NMR (CDCl$_3$, 300 MHz): δ (ppm)=7.06 (1H, t, J=7.2 Hz), 7.17 (21H, m), 7.80-7.83 (1H, m), 8.10-8.17 (2H, m).

Figure 15A:
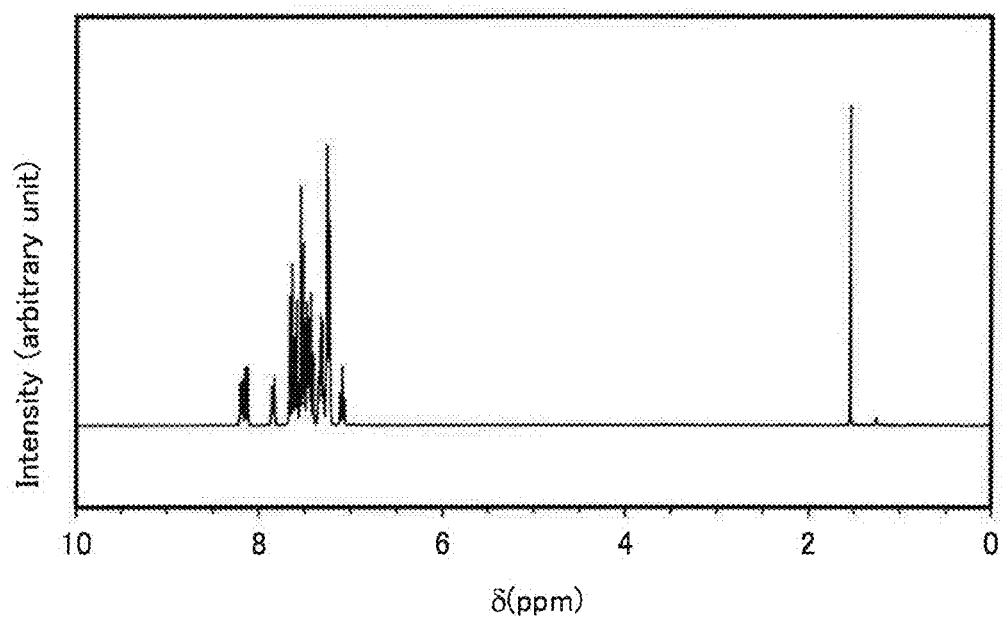
FIGS. 15A and 15B are 1H NMR charts of ThBA1BP-II.
Figure 15B:
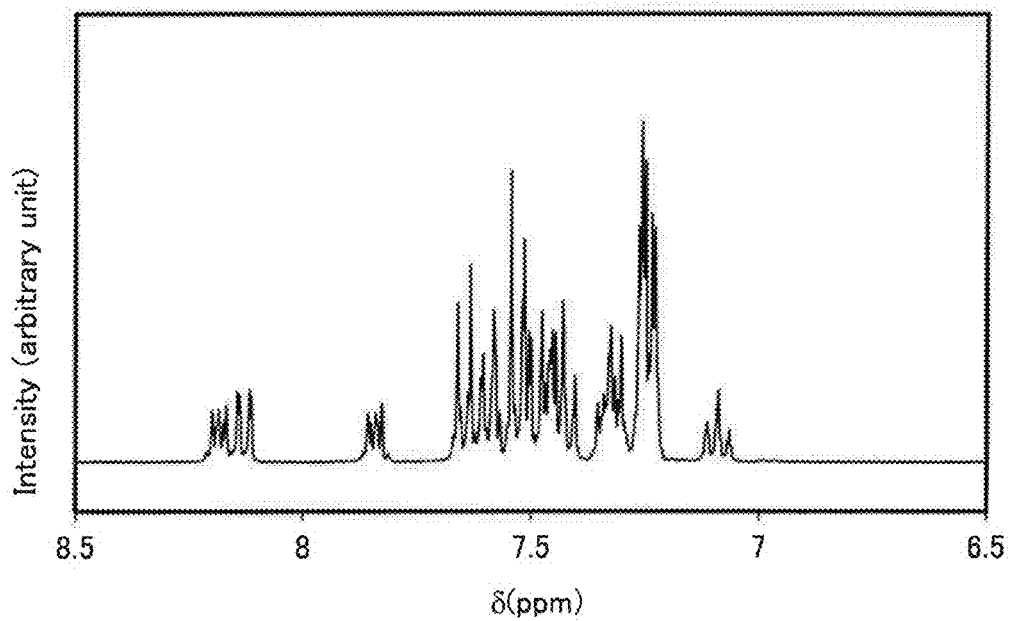

FIGS. 15(A) and (B) show $^1$H NMR charts. Note that FIG. 15(B) is an enlarged chart of FIG. 15(A). The measurement results show that the objective, ThBA1BP-II, was obtained.

The molecular weight of the above compound was measured with a GC/MS detector (ITQ1100 ion trap GCMS system, manufactured by Thermo Fisher). Accordingly, a main peak with a mass number of 503 (mode is EI+) was detected, and it was confirmed that the objective was obtained.

Example 3

Synthesis Example 3

In this synthesis example, a method for synthesizing N,N'-bis[4-(dibenzothiophen-4-yl)phenyl]-4-biphenylamine (abbreviation: ThBB1BP-II) represented by the structural formula shown below is described.

[Chemical Formula 38]

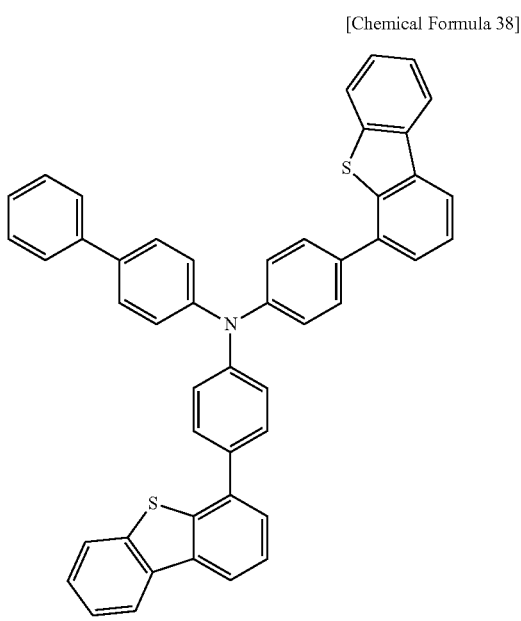 [SMILES: c1ccc(-c2ccc(N(c3ccc(-c4cccc5c4sc4ccccc45)cc3)c3ccc(-c4cccc5c4sc4ccccc45)cc3)cc2)cc1]

In a 100-mL three-neck flask were mixed 1.5 g (3 mmmol) of N,N'-bis(4-bromophenyl)-4-biphenylamine, 1.3 g (6 mmol) of dibenzothiophene-4-boronic acid, 13 mg (60 µmol) of palladium(II) acetate, 37 mg (120 µmol) of tri(o-tolyl)phosphine, 30 mL of toluene, 5 mL of ethanol, and 5 mL of a 2 mol/L aqueous potassium carbonate solution. This mixture was degassed while being stirred under reduced pressure, and then heated and stirred at 90° C. for 5 hours in a nitrogen atmosphere to be reacted.

After the reaction, 250 mL of toluene was added to this reaction mixture solution, and filtration was performed through Florisil and Celite. The obtained filtrate was concentrated, and purified by silica gel column chromatography (developing solvent toluene:hexane=1:4), so that 1.8 g of white powder which was the objective was obtained with a yield of 90%. A reaction scheme is shown below.

[Chemical Formula 39]

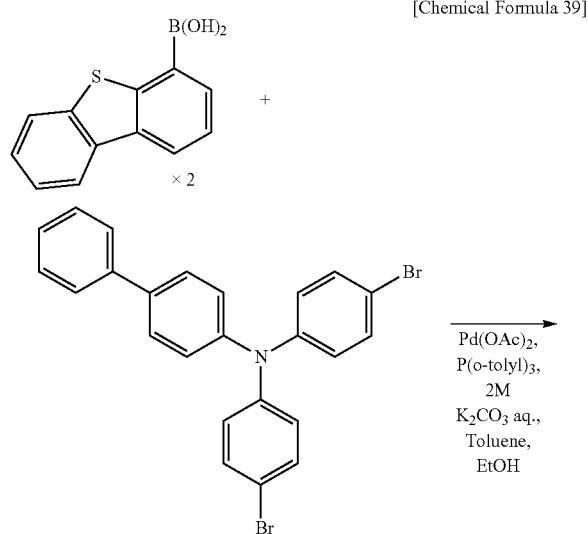

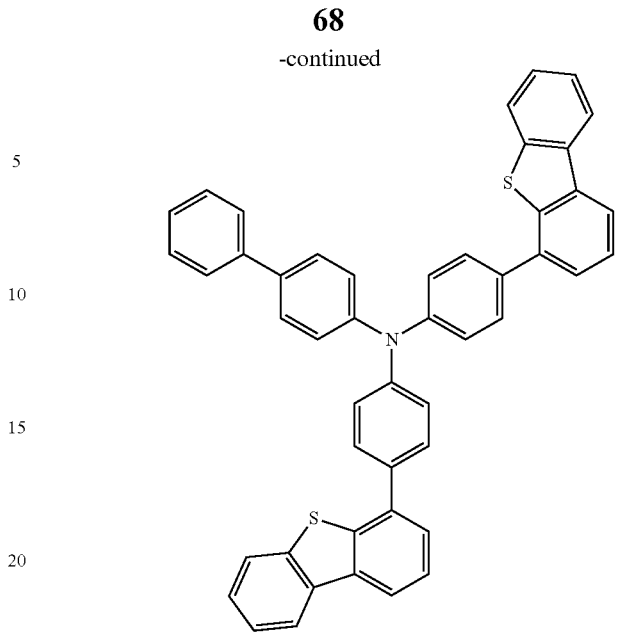

The Rf value by a silica gel thin layer chromatography (TLC) (developing solvent, ethyl acetate:hexane=1:10) was 0.39 for the objective, and 0.72 for N,N-bis(4-bromophenyl)-4-biphenylamine.

The obtained compound was measured by a nuclear magnetic resonance method (NMR). The measurement data are shown below.

$^1$H NMR (CDCl$_3$, 300 MHz): δ (ppm)=7.33-7.64 (21H, m), 7.71 (4H, d, J=6.3 Hz), 7.84-7.87 (2H, m), 8.14 (2H, dd, J=2.1 Hz, 7.8 Hz), 8.17-8.20 (2H, m).

Figure 16A:
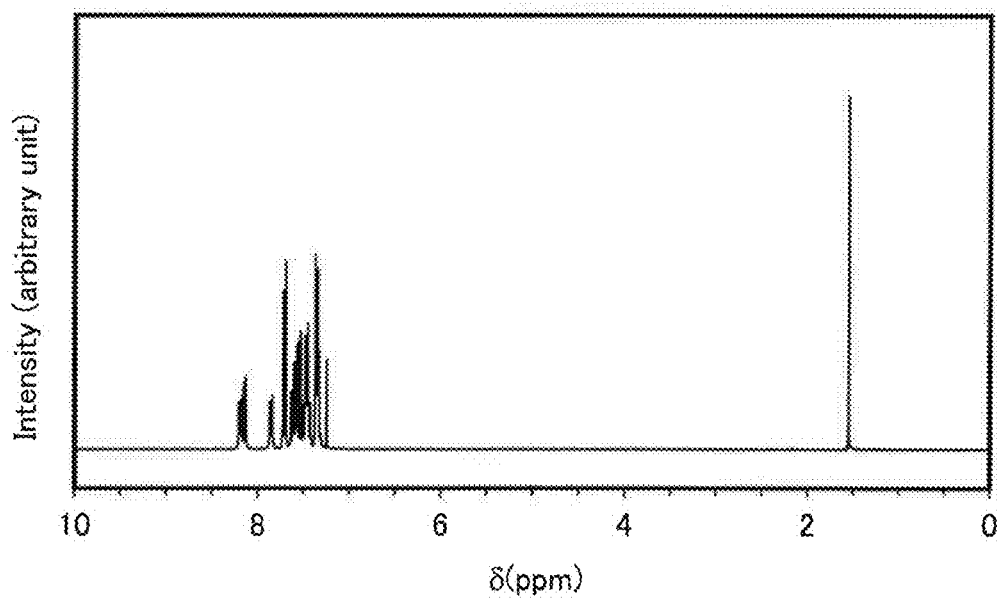
FIGS. 16A and 16B are 1H NMR charts of ThBB1BP-II.
Figure 16B:
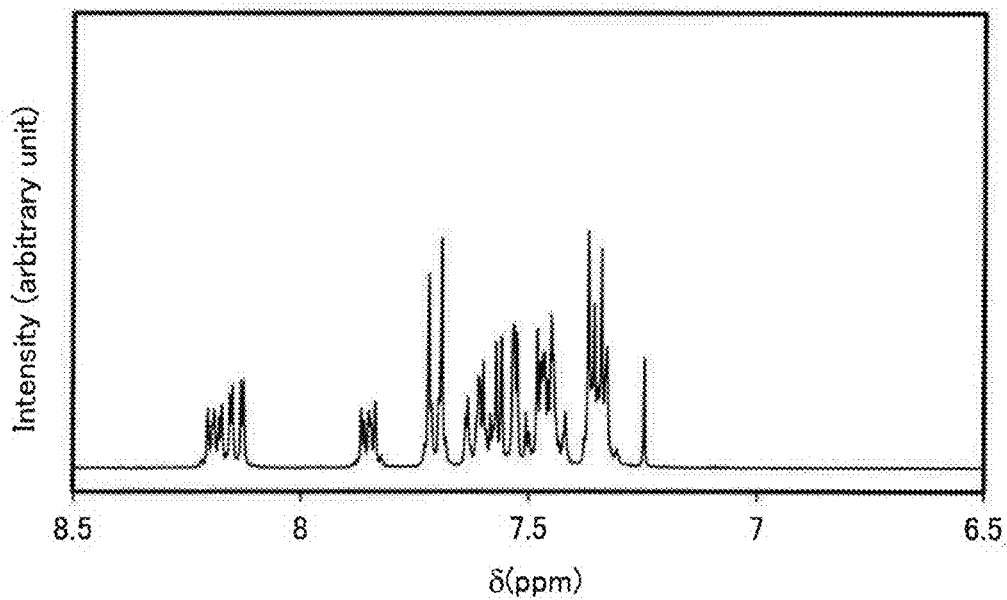

FIGS. 16(A) and (B) show $^1$H NMR charts. Note that FIG. 16(B) is an enlarged chart of FIG. 16(A). The measurement results show that the objective, ThBB1BP-II, was obtained.

The molecular weight of the above compound was measured with a GC/MS detector (ITQ1100 ion trap GCMS system, manufactured by Thermo Fisher). Accordingly, a main peak with a mass number of 685 (mode is EI+) was detected, and it was confirmed that the objective was obtained.

The glass transition temperature was measured using a differential scanning calorimeter (DSC, Pyris 1 DSC, manufactured by PerkinElmer, Inc.). According to the measurement results, the glass transition temperature was 130° C. Thus, it was found that ThBB1BP-II had a high glass transition temperature and good heat resistance.

Example 4

In this example, characteristics relating to the levels of mThBA1BP-II, ThBA1BP-II, and ThBB1BP-II synthesized in the above synthesis examples are described.

The oxidation-reduction reaction characteristics of mThBA1BP-II, ThBA1BP-II, and ThBB1BP-II were examined by cyclic voltammetry (CV) measurement. An electrochemical analyzer (model: ALS model 600A or 600C, manufactured by BAS Inc.) was used for the measurement. A measurement solution was prepared by dissolving a supporting electrolyte of tetra-n-butylammonium perchlorate (n-Bu$_4$NClO$_4$) in a solvent of dehydrated dimethylformamide (DMF) such that the concentration became 100 mmol/L, and by further dissolving the measurement object such that the concentration became 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag+ electrode (RE7 nonaqueous solvents reference electrode, manufactured by BAS Inc.) was used as a reference electrode. The scan rate was uniformly set to 0.1 V/sec.

Table 1 shows the HOMO levels obtained from oxidation potentials as a result of the measurement. It was found that the organic compound of one embodiment of the present invention had a HOMO level of approximately −5.5 to −5.6 eV. Therefore, it was found that the organic compound is preferable for hole injection from a material having a HOMO level close to the value, preferably within ±0.3 eV of the value, and hole injection into a material having a HOMO level within ±0.3 eV of the value. These HOMO levels are suitable because when the organic compound is used for a fluorescent element using a host material having an anthracene skeleton or a carbazole skeleton, a light-emitting element with particularly favorable characteristics can be obtained. Further, it was found that the organic compound of one embodiment of the present invention is also suitable as a hole-transport layer and a hole-transport host in a light-emitting layer.

TABLE 1

| Abbreviation | HOMO[eV] |
|---|---|
| mThBA1BP-II | −5.55 |
| ThBA1BP-II | −5.53 |
| ThBB1BP-II | −5.54 |

It was found that the HOMO level of mThBA1BP-II is slightly deeper than that of ThBA1BP-II, and dibenzothiophene is preferably bonded to a phenylamine by meta substitution, for hole transportation between layers with deeper HOMO levels.

It was found that the HOMO level of ThBA1BP-II is shallower than that of ThBB1BP-II, and multiple dibenzothiophenes are preferably bonded to a phenylamine, for hole transfer between layers with shallower HOMO levels.

Next, the absorption spectra and emission spectra of solutions and thin films of mThBA1BP-II, ThBA1BP-II and ThBB1BP-II were measured. An ultraviolet-visible light spectrophotometer (V550 type, manufactured by JASCO Corporation) was used for the measurements of the absorption spectra. A fluorescence spectrophotometer (FS920, manufactured by Hamamatsu Photonics K.K.) was used for the measurements of the emission spectra. The spectra of the solutions were measured using quartz cells. The thin film samples were formed by vacuum evaporation of the above compounds on quartz substrates. Note that the absorption spectrum was shown by subtracting the absorption spectrum of quartz from the measured spectrum of the sample.

Figure 17:
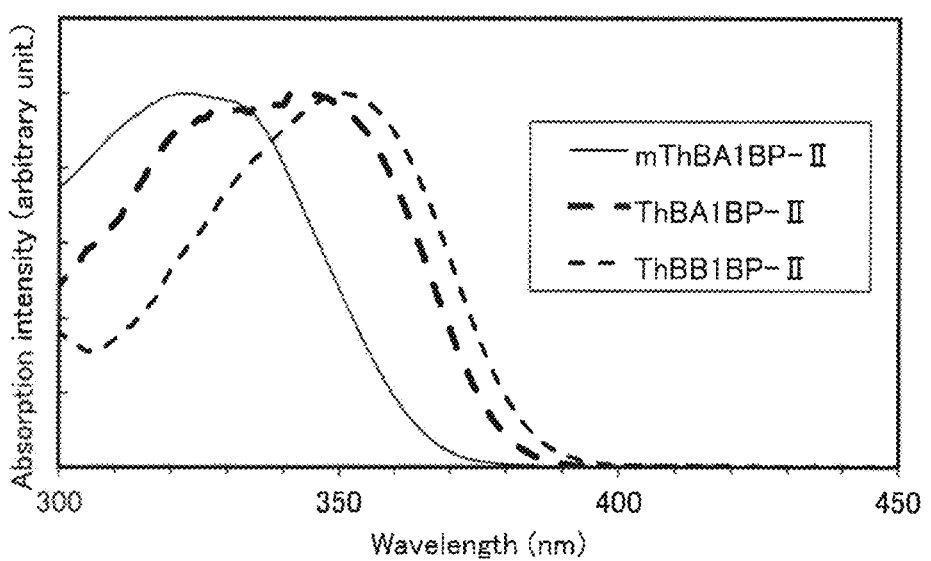
FIG. 17 illustrates absorption spectra of mThBA1BP-II, ThBA1BP-II, and ThBB1BP-II in toluene solutions.
Figure 18:
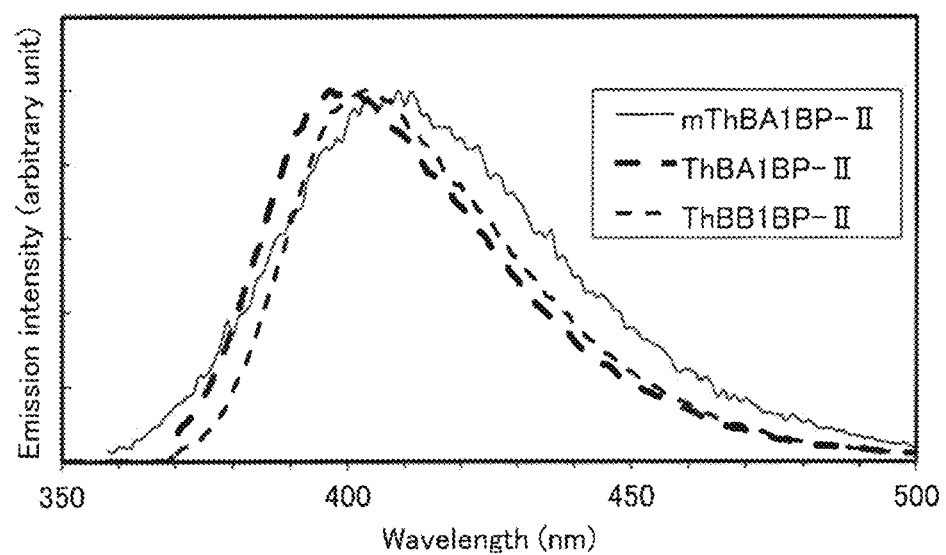
FIG. 18 illustrates emission spectra of mThBA1BP-II, ThBA1BP-II, and ThBB1BP-II in toluene solutions.
Figure 19:
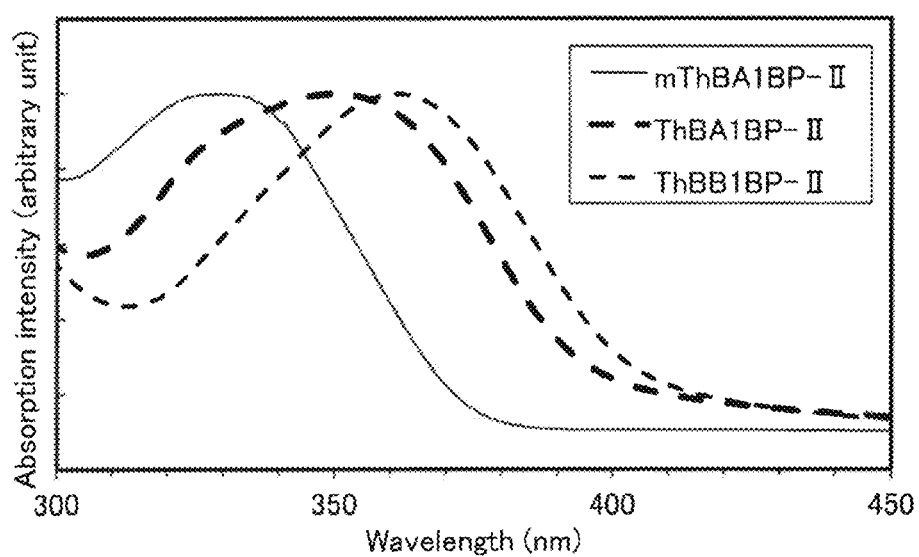
FIG. 19 illustrates absorption spectra of thin films of mThBA1BP-II, ThBA1BP-II, and ThBB1BP-II.
Figure 20:
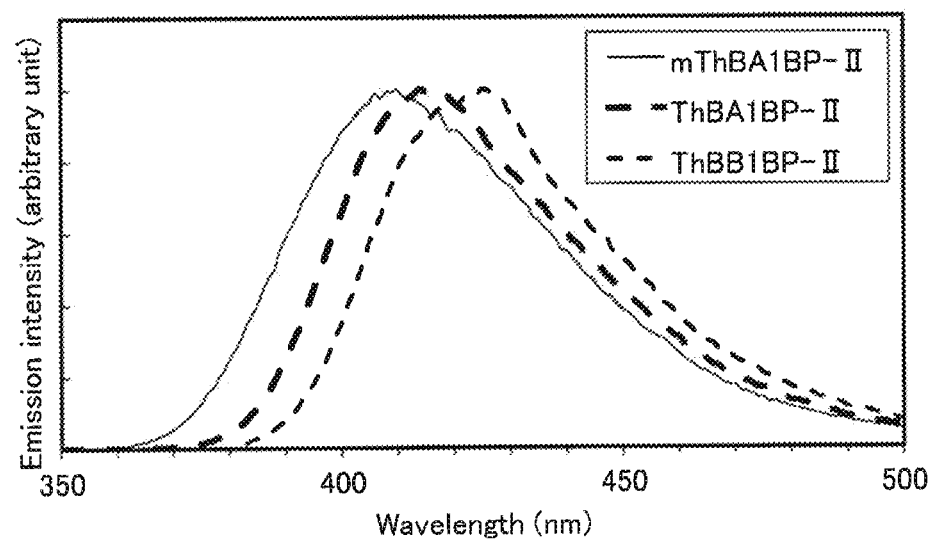
FIG. 20 illustrates thin films and emission spectra of mThBA1BP-II, ThBA1BP-II, and ThBB1BP-II.

As measurement results, the absorption spectra of toluene solutions are shown in FIG. 17, and the emission spectra thereof are shown in FIG. 18. The absorption spectra of the thin films are shown in FIG. 19, and the emission spectra thereof are shown in FIG. 20.

It was found from the graphs that the absorption edges of mThBA1BP-II, ThBA1BP-II, and ThBB1BP-II exist in an extremely short wavelength region of 400 nm or less and the optical gaps thereof are wide. It was found that the absorption edge of mThBA1BP-II exists on the significantly short wavelength side compared with the other two substances, and the band gap of mThBA1BP-II is particularly wide.

These indicate that when these materials are used in a light-emitting layer and a layer adjacent to the light-emitting layer, these materials are unlikely to absorb the singlet energy of a dopant and the like and thus a light-emitting element that has favorable emission efficiency can be provided.

It was also found that the organic compounds emit bluish violet light and thus can be used as bluish violet dopants. In addition, it was found that the organic compounds are suitable as host materials of dopants that emit light having a longer wavelength than bluish violet.

In this example, the HOMO levels, the LUMO levels, and the T1 levels of various structures of mThBA1BP-II, ThBA1BP-II, and ThBB1BP-II were simulated by quantum chemistry calculation.

The most stable structures in the singlet and in the triplet were obtained by calculation using the density functional theory. In this case, vibration analysis was conducted on each of the most stable structures. As a basis function, 6-311G was applied to all the atoms. Furthermore, to improve calculation accuracy, the p function and the d function, respectively, were added as polarization basis sets to hydrogen atoms and atoms other than hydrogen atoms. As a functional, B3LYP was used. Each of the HOMO level and the LUMO level of the singlet structure was calculated. Then, the T1 level was calculated from a zero-point corrected energy difference obtained from the most stable structures in the singlet ground state and in the lowest excited triplet state. Gaussian 09 was used as the quantum chemistry calculation program. In addition, the lowest singlet excitation energy (S1) was calculated by a time-dependent (TD) calculation method using the most stable structure in the singlet ground state.

Table 2 shows values obtained by the calculations.

TABLE 2

| Abbreviation | HOMO | LUMO | S1 | T1 |
|---|---|---|---|---|
| mThBA1BP-II | −5.21 | −1.31 | 3.43 | 2.69 |
| ThBA1BP-II | −5.19 | −1.32 | 3.42 | 2.53 |
| ThBB1BP-II | −5.20 | −1.36 | 3.38 | 2.55 |

Unit: [eV]

It was found from the calculated S1 levels (excitation energies from S0 to S1) that the S1 levels of these organic compounds are high, and when they are used in a light-emitting layer and a layer in contact with the light-emitting layer, they can suitably be used for a variety of elements of visible regions, for example, a short-wavelength fluorescent element of blue and the like to a long-wavelength fluorescent element of red and the like. Furthermore, the S1 level of ThBA1BP-II is next highest to that of mThBA1BP-II, and it was found that there is a correlation with actually measured energy values of the absorption edges of the solutions and the thin films.

The calculated T1 levels (a difference in most stable energy between the S0 and T1 states) show that the T1 level of the amine material of one embodiment of the present invention is high, indicating that when it is used in a light-emitting layer and a layer in contact with the light-emitting layer, it can suitably be used for elements of visible regions, for example, a short-wavelength phosphorescent element of blue and the like to a long-wavelength phosphorescent element of red and the like. Furthermore, the T1 levels of mThBA1BP-II and ThBA1BP-II are high in this order, and the T1 level is suitably higher for an element that emits light with a shorter wavelength.

Although the calculated HOMO levels tended to be shallower (have larger values) than the actually measured HOMO levels, it was found that the order of the calculated 3 materials has a correlation with that of actual measurement. It is presumed that the values of the LUMO levels are shallower than these, indicating that these organic compounds have high LUMO levels. Thus, it was found that when these organic compounds are used for a hole-transport layer, they also serve as an electron-block layer, and a light-emitting element can have high efficiency.

Example 5

In this example, Light-emitting Element 1 that is one embodiment of the present invention described in Embodiment 1 and Comparative Light-emitting Element 1 are described. The structural formulae of organic compounds used in Light-emitting Element 1 and the Comparative Light-emitting Element 1 are shown below.

[Chemical Formulae 40]

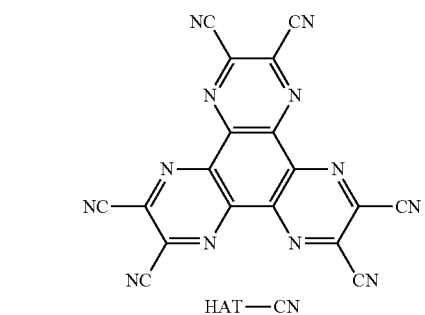

HAT—CN (i)

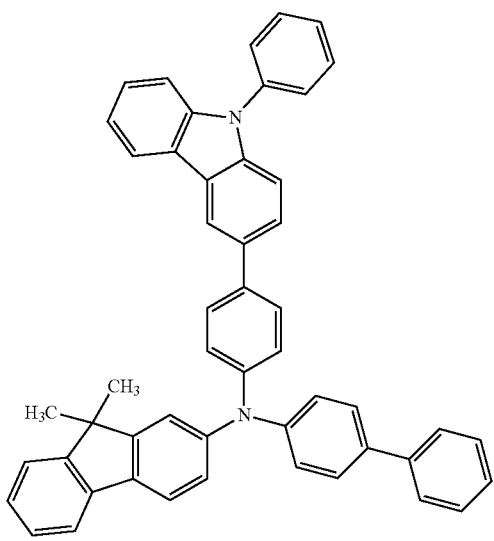

PCBBiF (ii)

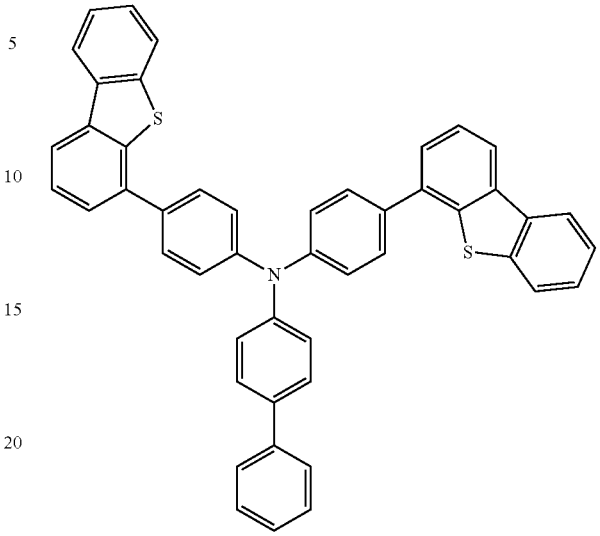

ThBBIBP—II (iii)

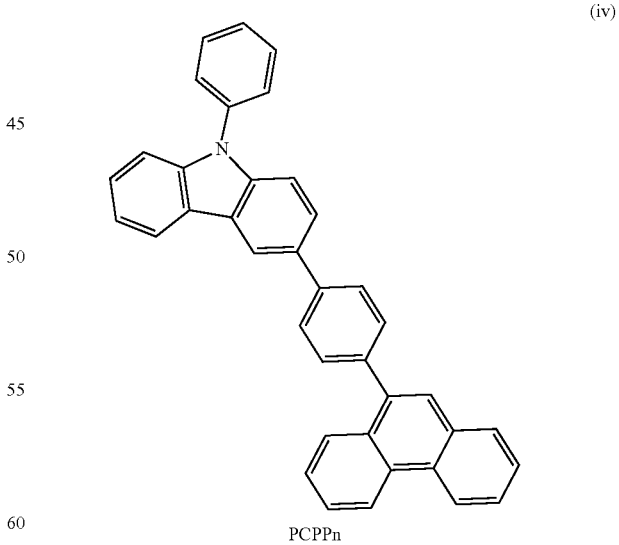

PCPPn (iv)

-continued (v)
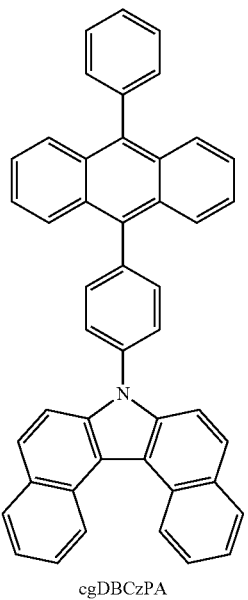
cgDBCzPA

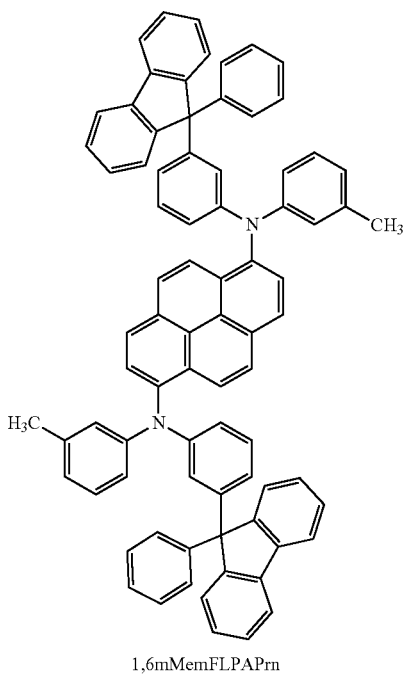
1,6mMemFLPAPrn (vii)
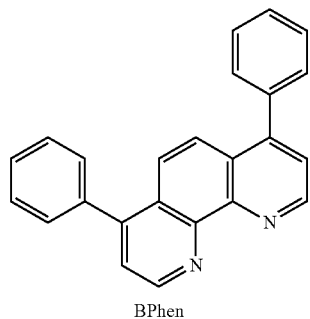
BPhen (Method for Fabricating Light-Emitting Element 1)

First, indium tin oxide containing silicon oxide (ITSO) was deposited on a glass substrate by a sputtering method to form the first electrode 101. Note that the film thickness of the first electrode 101 was 110 nm and the area of the electrode was 2 mm×2 mm.

Next, in pretreatment for forming the light-emitting element on the substrate, a surface of the substrate was washed with water and baked at 200° C. for 1 hour, and then UV ozone treatment was performed for 370 seconds.

After that, the substrate was introduced into a vacuum evaporation apparatus in which the pressure was reduced to about $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation device such that the side on which the first electrode 101 was formed faced downward. Then, 2,3,6,7,10,11-hexacyano-1,4,5,8,9,12-hexaazatriphenylene (abbreviation: HAT-CN) represented by the above structural formula (i) was deposited to a thickness of 5 nm on the first electrode 101 by an evaporation method using resistance heating, whereby the hole-injection layer 111 was formed.

(vi) Next, N-(1,1'-biphenyl-4-yl)-9,9-dimethyl-N-[4-(9-phenyl-9H-carbazol-3-yl)phenyl]-9H-fluor en-2-amine (abbreviation: PCBBiF) represented by the above structural formula (ii) was deposited to a thickness of 20 nm on the hole-injection layer 111 by evaporation, whereby the first hole-transport layer 112-1 was formed; N,N-bis[4-(dibenzothiophen-4-yl)phenyl]-4-biphenylamine (abbreviation: ThBB1BP-II) represented by the above structural formula (iii) was deposited to a thickness of 5 nm on the first hole-transport layer 112-1 by evaporation, whereby the second hole-transport layer 112-2 was formed; and 3-[4-(9-phenanthryl)-phenyl]-9-phenyl-9H-carbazole (abbreviation: PCPPn) represented by the above structural formula (iv) was deposited to a thickness of 5 nm on the second hole-transport layer 112-2 by evaporation, whereby the third hole-transport layer 112-3 was formed.

Subsequently, the light-emitting layer 113 was formed by co-evaporation of 7-[4-(10-phenyl-9-anthryl)phenyl]-7H-dibenzo[c,g]carbazole (abbreviation: cgDBCzPA) represented by the above structural formula (v) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (vi) in a weight ratio of 1:0.03 (=cgDBCzPA:1,6mMemFLPAPrn) to a thickness of 25 nm.

Then, on the light-emitting layer 113, cgDBCzPA was deposited to a thickness of 10 nm by evaporation, and bathophenanthroline (abbreviation: BPhen) represented by the above structural formula (vii) was deposited to a thickness of 15 nm by evaporation to form the electron-transport layer 114.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the second electrode 102. Thus, Light-emitting Element 1 of this example was fabricated.

(Method for Fabricating Comparative Light-Emitting Element 1)

Comparative Light-emitting Element 1 was fabricated in a manner similar to that of Light-emitting Element 1 except that the first hole-transport layer 112-1 in Light-emitting Element 1 was formed to a thickness of 25 nm and the second hole-transport layer 112-2 was not formed. That is, Comparative Light-emitting Element 1 can be said to be a light-emitting element in which the second hole-transport layer 112-2 was not formed and the thickness of the first hole-transport layer 112-1 was increased by the thickness of the second hole-transport layer 112-2.

(Method for Fabricating Comparative Light-Emitting Element 2)

Comparative Light-emitting Element 2 was fabricated in a manner similar to that of Light-emitting Element 1 except that the first hole-transport layer 112-1 in Light-emitting Element 1 was formed to a thickness of 30 nm and neither the second hole-transport layer 112-2 nor the third hole-transport layer 112-3 was formed. That is, Comparative Light-emitting Element 2 can be said to be a light-emitting element in which neither the second hole-transport layer 112-2 nor the third hole-transport layer 112-3 was formed and the thickness of the first hole-transport layer 112-1 was increased by the thicknesses of the second hole-transport layer 112-2 and the third hole-transport layer 112-3.

Light-emitting Element 1 and Comparative Light-emitting Elements 1 to 3 were sealed using a glass substrate in a glove box containing a nitrogen atmosphere so as not to be exposed to the air (a sealing material was applied to surround the elements and UV treatment and heat treatment at 80° C. for 1 hour were performed at the time of sealing). Then, the initial characteristics and reliability of these light-emitting elements were measured. Note that the measurements were performed at room temperature (in an atmosphere kept at 25° C.).

Figure 21:
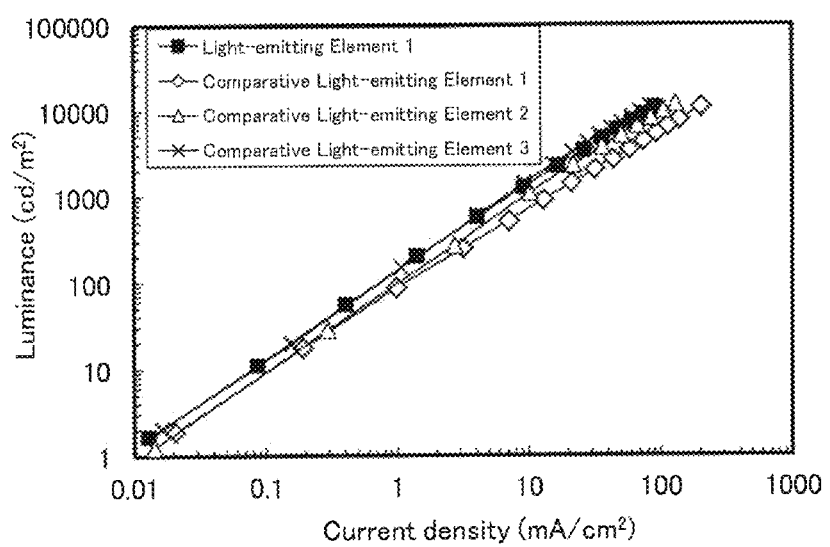
FIG. 21 illustrates luminance-current density characteristics of Light-emitting Element 1.
Figure 22:
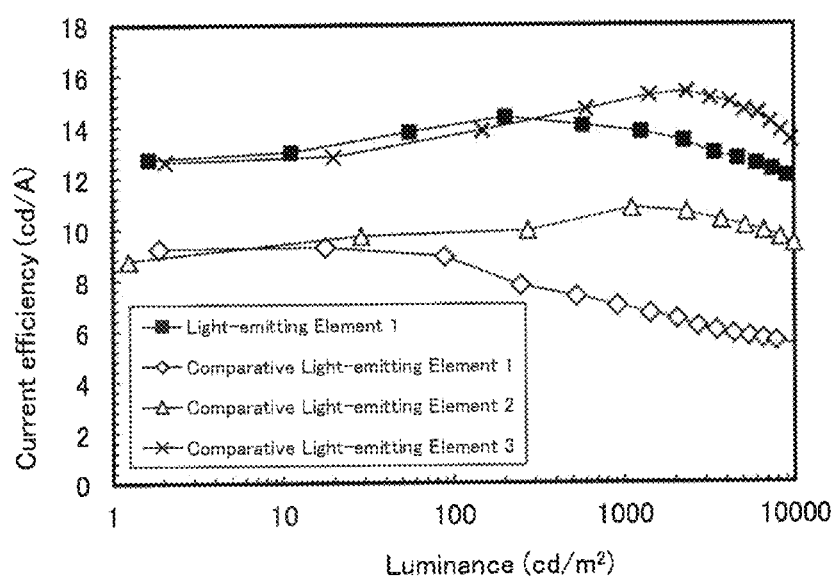
FIG. 22 illustrates the current efficiency-luminance characteristics of Light-emitting Element 1.
Figure 23:
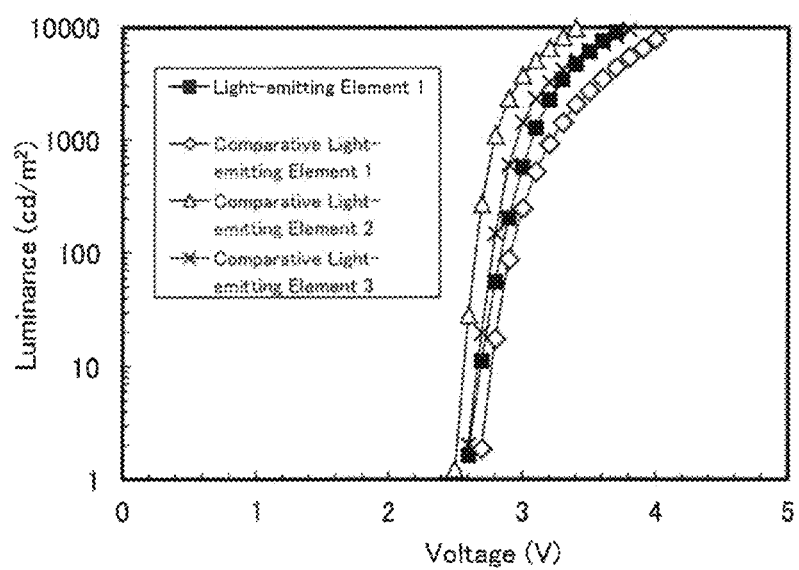
FIG. 23 illustrates the luminance-voltage characteristics of Light-emitting Element 1.
Figure 24:
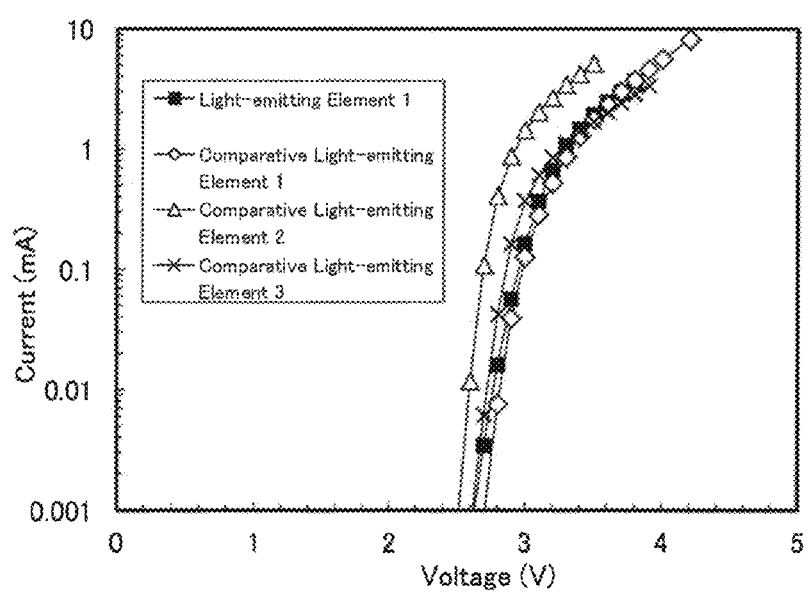
FIG. 24 illustrates the current-voltage characteristics of Light-emitting Element 1.
Figure 25:
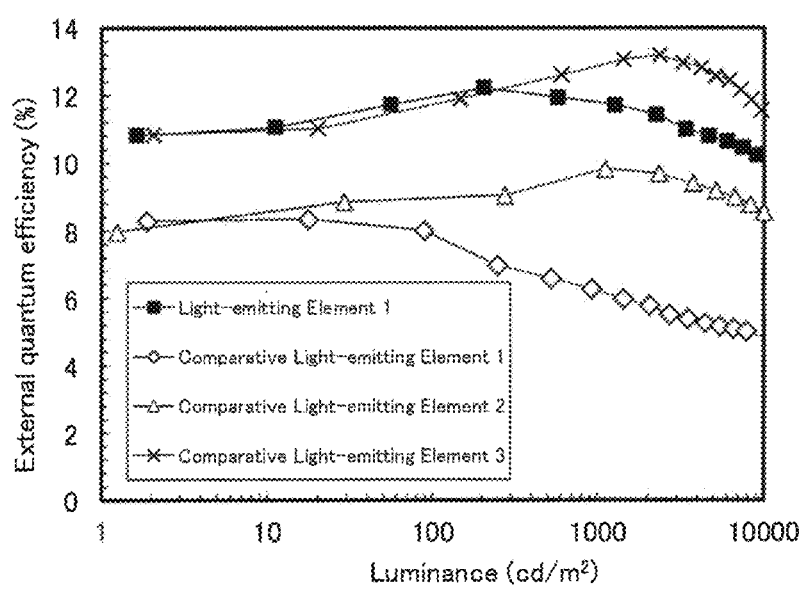
FIG. 25 illustrates the external quantum efficiency-luminance characteristics of Light-emitting Element 1.
Figure 26:
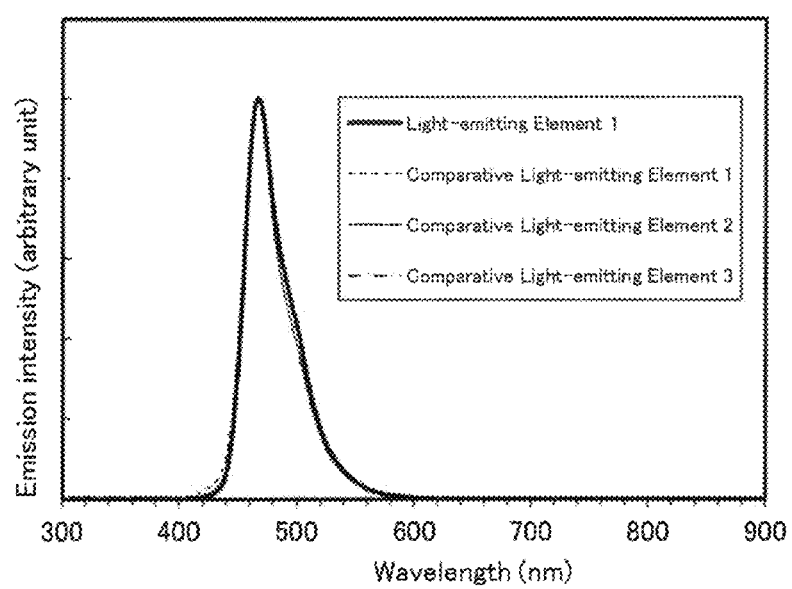
FIG. 26 illustrates an emission spectrum of Light-emitting Element 1.

FIG. 21 shows the luminance-current density characteristics of Light-emitting Element 1 and Comparative Light-emitting Elements 1 to 3. FIG. 22 shows the current efficiency-luminance characteristics thereof. FIG. 23 shows the luminance-voltage characteristics thereof. FIG. 24 shows the current-voltage characteristics thereof. FIG. 25 shows the external quantum efficiency-luminance characteristics thereof. FIG. 26 shows the emission spectra thereof. Table 4 shows the main characteristics of the light-emitting elements at approximately 1000 cd/m$^2$.

TABLE 4

|  | Voltage (V) | Current (mA) | Current density (mA/cm$^2$) | Chromaticity x | Chromaticity y | Current efficiency (cd/A) | External quantum efficiency (%) |
| --- | --- | --- | --- | --- | --- | --- | --- |
| Light-emitting Element 1 | 3.0 | 0.20 | 5 | 0.14 | 0.18 | 13.7 | 11.8 |
| Comparative Light-emitting Element 1 | 3.2 | 0.52 | 13 | 0.14 | 0.17 | 7.0 | 6.3 |
| Comparative Light-emitting Element 2 | 2.8 | 0.41 | 10 | 0.14 | 0.16 | 10.8 | 9.8 |
| Comparative Light-emitting Element 3 | 2.9 | 0.16 | 4 | 0.14 | 0.17 | 14.7 | 12.6 |

(Method for Fabricating Comparative Light-Emitting Element 3)

Comparative Light-emitting Element 3 was fabricated in a manner similar to that of Light-emitting Element 1 except that the first hole-transport layer 112-1 in Light-emitting Element 1 was formed to a thickness of 25 nm and the third hole-transport layer 112-3 was not formed. That is, Comparative Light-emitting Element 3 can be said to be a light-emitting element in which the third hole-transport layer 112-3 was not formed and the thickness of the first hole-transport layer 112-1 was increased by the thickness of the third hole-transport layer 112-3.

Note that the thickness of the whole hole-transport layers 112 is uniform in order to remove an influence due to a difference in the thickness of the organic layer.

The following table lists the element structures of Light-emitting Element 1 and Comparative Light-emitting Elements 1 to 3.

It was found from FIG. 21 to FIG. 26 and Table 2 that Light-emitting Element 1, one embodiment of the present invention, has more favorable driving voltage than Comparative Light-emitting Element 1 without the second hole-transport layer 112-2, has higher efficiency than Comparative Light-emitting Elements 1 and 2, and is a blue light-emitting element having favorable characteristics like Comparative Light-emitting Element 3.

Figure 27:
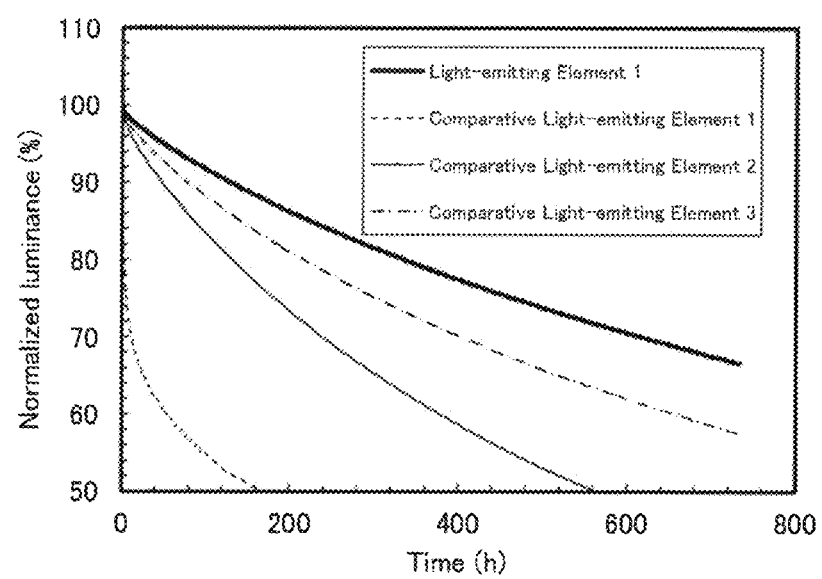
FIG. 27 illustrates the normalized luminance-temporal change characteristics of Light-emitting Element 1.

FIG. 27 shows a change in luminance with driving time under the conditions where the initial luminance is 5000 cd/m$^2$ and the current density is constant. As shown in FIG. 27, a decrease in luminance with accumulation of driving time of Light-emitting Element 1, one embodiment of the present invention, is smaller than those of Comparative Light-emitting Element 1 without the second hole-transport layer 112-2, Comparative Light-emitting Element 2 in which only the first hole-transport layer 112-1 is formed, and Comparative Light-emitting Element 3 without the third hole-transport layer 112-3, showing that Light-emitting Element 1 has a favorable lifetime.

TABLE 3

| Hole-injection layer | Hole-transport layer | | | Light-emitting layer | Electron-transport layer | | Electron-injection layer |
| --- | --- | --- | --- | --- | --- | --- | --- |
|  | 1 | 2 | 3 |  |  |  |  |
| 5 nm | *1 | *2 | *3 | 25 nm | 10 nm | 15 nm | 1 nm |
| HAT-CN | PCBBiF | ThBB1BP-II | PCPPn | cgDBCzPA:1,6mMemFLPAPrn (1:0.03) | cgDBCzPA | BPhen | LiF |

*1 Light-emitting Element 1: 20 nm, Comparative Light-emitting Element 1: 25 nm, Comparative Light-emitting Element 2: 30 nm, Comparative Light-emitting Element 3: 25 nm
*2 Light-emitting Element 1: 5 nm, Comparative Light-emitting Element 1: 0 nm, Comparative Light-emitting Element 2: 0 nm, Comparative Light-emitting Element 3: 5 nm
*3 Light-emitting Element 1: 5 nm, Comparative Light-emitting Element 1: 5 nm, Comparative Light-emitting Element 2: 0 nm, Comparative Light-emitting Element 3: 0 nm The HOMO levels of the first to third hole-transport materials, the host material, and the light-emitting material of the light-emitting elements of this example are shown in the following table. Note that the HOMO level and the LUMO level were calculated through cyclic voltammetry (CV) measurement. A calculation method was the same as that of Example 4.

TABLE 5

| | First hole-transport layer | Second hole-transport layer | Third hole-transport layer | Light-emitting layer | |
|---|---|---|---|---|---|
| | | | | Host material | Light-emitting material |
| Material | PCBBiF | ThBB1BP-II | PCPPn | cgDBCzPA | 1,6mMemFLPAPm |
| HOMO level (eV) | −5.36 | −5.54 | −5.80 | −5.69 | −5.40 |

As shown in the table, as for the materials used in Light-emitting Element 1, the HOMO level of the second hole-transport material is deeper than the HOMO level of the first hole-transport material, the HOMO level of the host material is deeper than the HOMO level of the second hole-transport material, and the HOMO level of the third hole-transport material is deeper than the HOMO level of the host material. Furthermore, the HOMO level of the light-emitting material is shallower than the HOMO level of the host material.

The HOMO level of PCBBiF that is the first hole-transport material is as shallow as −5.36 eV and can easily cause charge separation by interacting with the LUMO level of −4.41 eV of HAT-CN. However, the HOMO level of cgDBCzPA that is the host material is −5.69 eV and its difference from the HOMO level of PCBBiF is as large as 0.33 eV; thus, it is difficult to directly inject holes from the first hole-transport layer 112-1 into the host material of the light-emitting layer. Since the HOMO level of 1,6mMemFL-PAPrn that is the light-emitting material is −5.40 eV and the difference in HOMO level between the light-emitting material and the first hole-transport material is small, holes are injected into the light-emitting material in some cases. However, when holes are directly injected into the light-emitting material, holes are trapped at the interface between the first hole-transport layer 112-1 and the light-emitting layer, and a light-emitting region is concentrated to promote deterioration. Furthermore, in this case, holes of the hole-transport material of the first hole-transport layer 112-1 do not easily enter the host material of the light-emitting layer. Therefore, holes and electrons are accumulated in the hole-transport material and the host material, respectively. Accordingly, an exciplex having lower energy than the light-emitting material might be formed between the hole-transport material and the host material; thus, disadvantages such as reduction in emission efficiency are likely to occur. This is a cause of poorer characteristics of Comparative Light-emitting Element 2 than those of Light-emitting Element 1.

In Light-emitting Element 1, the second hole-transport material whose HOMO level is shallower than the HOMO level of the host material but deeper than the HOMO level of the first hole-transport material is used as the second hole-transport layer 112-2, whereby holes are first injected from the first hole-transport layer 112-1 into the second hole-transport layer 112-2. The HOMO level of ThBB1BP-II that is the second hole-transport material is −5.54 eV and its difference from the HOMO level of PCBBiF that is the first hole-transport material is as small as 0.18 eV. Accordingly, holes are smoothly injected from the first hole-transport layer 112-1 into the second hole-transport layer 112-2.

Here, if holes are injected from the second hole-transport layer 112-2 into the light-emitting layer 113, a barrier of approximately 0.15 eV exists between the second hole-transport material and the host material. Even with such a difference, holes are usually injected without problems. Meanwhile, the HOMO level of the light-emitting material included in the light-emitting layer 113 is −5.40 eV, and thus a barrier does not exist. Therefore, holes are preferentially injected into the light-emitting material over into the host material eventually. As described above, direct injection of holes into the light-emitting material is likely to cause disadvantages such as acceleration of deterioration and reduction in emission efficiency. This is a cause of lower reliability of Comparative Light-emitting Element 3 than that of Light-emitting Element 1.

Thus, in Light-emitting Element 1 that is the light-emitting element of one embodiment of the present invention, the third hole-transport layer 112-3 was further provided between the second hole-transport layer 112-2 and the light-emitting layer 113. The HOMO level of PCPPn that is the third hole-transport material included in the third hole-transport layer 112-3 is −5.80 eV, which is deeper than the HOMO level of the host material. Thus, holes are preferentially injected into the host material because there is no barrier to hole injection into the host material and also because of the mixing ratio between the host material and the light-emitting material. Although the holes injected into the host material are partly trapped in the light-emitting material, they can be moved toward the second electrode while being trapped moderately, and the host material is an anthracene compound, which also has an electron-transport property; accordingly, the driving voltage does not increase. In addition, the light-emitting region extends over the light-emitting layer 113 without being localized, and deterioration is not promoted. Therefore, the light-emitting elements had favorable emission efficiency.

Note that in Comparative Light-emitting Element 1, which is not provided with the second hole-transport layer 112-2, holes are injected from the first hole-transport layer 112-1 into the third hole-transport layer 112-3. The difference in HOMO level between the first hole-transport material and the third hole-transport material is as large as 0.44 eV; consequently, it is found that both efficiency and reliability are significantly reduced.

REFERENCE NUMERALS

1 lighting system
2 control portion
3 sensor portion
4 lighting portion
5 database
6 light-emitting device portion 101 first electrode
102 second electrode
103 EL layer
111 hole-injection layer
112-1 first hole-transport layer
112-2 second hole-transport layer
112-3 third hole-transport layer
113 light-emitting layer
114 electron-transport layer
115 electron-injection layer
116 charge generation layer
117 P-type layer
118 electron-relay layer
119 electron-injection buffer layer
400 substrate
401 first electrode
403 EL layer
404 second electrode
405 sealant
406 sealant
407 sealing substrate
412 pad
420 IC chip
501 first electrode
502 second electrode
511 first light-emitting unit
512 second light-emitting unit
513 charge generation layer
601 driver circuit portion (source line driver circuit)
602 pixel portion
603 driver circuit portion (gate line driver circuit)
604 sealing substrate
605 sealant
607 space
608 wiring
609 FPC (flexible printed circuit)
610 element substrate
611 switching FET
612 current controlling FET
613 first electrode
614 insulator
616 EL layer
617 second electrode
618 light-emitting element
730 insulating film
770 planarization insulating film
772 conductive film
782 light-emitting element
783 droplet discharge apparatus
784 droplet
785 layer
786 EL layer
788 conductive film
901 housing
902 liquid crystal layer
903 backlight unit
904 housing
905 driver IC
906 terminal
951 substrate
952 electrode
953 insulating layer
954 partition layer
955 EL layer
956 electrode
1001 substrate
1002 base insulating film
1003 gate insulating film
1006 gate electrode
1007 gate electrode
1008 gate electrode
1020 first interlayer insulating film
1021 second interlayer insulating film
1022 electrode
1024W first electrode
1024R first electrode
1024G first electrode
1024B first electrode
1025 partition
1028 EL layer
1029 second electrode
1031 sealing substrate
1032 sealant
1033 transparent base material
1034R red coloring layer
1034G green coloring layer
1034B blue coloring layer
1035 black matrix
1036 overcoat layer
1037 third interlayer insulating film
1040 pixel portion
1041 driver circuit portion
1042 peripheral portion
1400 droplet discharge apparatus
1402 substrate
1403 droplet discharge means
1404 imaging means
1405 head
1406 dotted line
1407 control means
1408 storage medium
1409 image processing means
1410 computer
1411 marker
1412 head
1413 material supply source
1414 material supply source
1415 material supply source
1416 head
2001 housing
2002 light source
3001 lighting device
5000 display region
5001 display region
5002 display region
5003 display region
5004 display region
5005 display region
7101 housing
7103 display portion
7105 stand
7107 display portion
7109 operation key
7110 remote controller
7201 main body
7202 housing
7203 display portion
7204 keyboard
7205 external connection port
7206 pointing device
7210 second display portion
7301 housing
7302 housing
7303 joint portion 7304 display portion
7305 display portion
7306 speaker portion
7307 recording medium insertion portion
7308 LED lamp
7309 operation key
7310 connection terminal
7311 sensor
7401 housing
7402 display portion
7403 operation button
7404 external connection port
7405 speaker
7406 microphone
7400 mobile phone
9033 clasp
9034 switch
9035 power supply switch
9036 switch
9038 operation switch
9310 portable information terminal
9311 display panel
9312 display region
9313 hinge
9315 housing
9630 housing
9631 display portion
9631a display portion
9631b display portion
9632a touch panel region
9632b touch panel region
9633 solar cell
9634 charge and discharge control circuit
9635 battery
9636 DCDC converter
9637 operation key
9638 converter
9639 button

The invention claimed is:

1. A light-emitting element comprising:
an anode;
a first layer over the anode;
a second layer over the first layer;
a third layer over the second layer;
a light-emitting layer over the third layer; and
a cathode over the light-emitting layer,
wherein the first layer comprises an organic compound having at least one electron withdrawing group, wherein the organic compound is optionally a condensed heteroaromatic ring,
wherein the second layer comprises a triarylamine having a fluorenylamine skeleton,
wherein the third layer comprises an organic compound represented by Structural Formula (100) shown below:

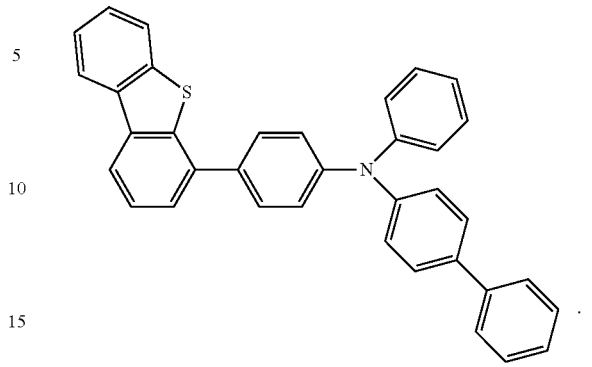

(100)

2. A light-emitting device comprising:
the light-emitting element according to claim 1; and
a transistor or a substrate.

3. An electronic device comprising:
the light-emitting device according to claim 2; and
a sensor, an operation button, a speaker, or a microphone.

4. A lighting device comprising:
the light-emitting device according to claim 2; and
a housing.

5. A lighting system comprising:
a control portion;
a sensor portion; and
a lighting portion,
wherein the lighting portion includes a plurality of light-emitting device portions,
wherein each light-emitting device portion of the plurality of light-emitting device portions includes one or more light-emitting elements, and
wherein each light-emitting element of the one or more light-emitting elements is the light-emitting element according to claim 1.

6. The lighting system according to claim 5, wherein the sensor portion senses presence information or positional information of a user and transmits the information to the control portion, whereby the control portion makes the light-emitting device portion emit light with appropriate emission intensity.

7. The lighting system according to claim 5, wherein the emission intensity of the light-emitting device portion is sequentially changed with a change in the positional information of the user.

8. A guidance system using the lighting system according to claim 5.

9. The guidance system according to claim 8,
wherein the sensor portion has a function of detecting attribute information of the user, and
wherein the guidance system guides the user in the appropriate direction by changing the emission intensity of the light-emitting device portion on the basis of the attribute information and the positional information of the user.

10. The light-emitting element according to claim 1, further comprising:
a fourth layer over the third layer,
wherein the fourth layer comprises an organic compound having a carbazole skeleton, a carbazole skeleton and a triphenylene skeleton, a carbazole skeleton and a phenanthrene skeleton, or a carbazole skeleton and a naphthalene skeleton.

11. The light-emitting element according to claim 1, wherein the organic compound in the first layer is 7,7,8,8-tetracyano-2,3,5,6-tetrafluoroquinodimethane, 3,6-difluoro-2,5,7,7,8,8-hexacyanoquinodimethane, chloranil, or 2,3,6,7,10,11-hexacyano-1,4,5,8,9,12-hexaazatriphenylene.

* * * * *